US012741927B2

(12) United States Patent
Manfredi et al.

(10) Patent No.: US 12,741,927 B2
(45) Date of Patent: Sep. 22, 2026

(54) METHODS FOR SYNTHESIZING ENANTIOPURE (S)-METHADONE, (R)-METHADONE, RACEMIC (R,S)-METHADONE AND RELATED ANALOGUE SUBSTANCES

(71) Applicants: Paolo L. Manfredi, Miami Beach, FL (US); Charles E. Inturrisi, New York, NY (US)

(72) Inventors: Paolo L. Manfredi, Miami Beach, FL (US); Charles E. Inturrisi, New York, NY (US); Andrea Mattarei, Perarolo di Vigonza (IT); Marco Banzato, Galzignano Terme (IT); Alberto Furlan, Padua (IT); Alberto Ongaro, Campolongo Maggiore (IT); Brian H. Heasley, Wake Forest, NC (US); Zachary D. Tucker, Cary, NC (US)

(73) Assignees: Paolo L. Manfredi, Miami Beach, FL (US); Charles E. Inturrisi, New York, NY (US)

( * ) Notice: Subject to any disclaimer, the term of this patent is extended or adjusted under 35 U.S.C. 154(b) by 413 days.

(21) Appl. No.: 18/554,025

(22) PCT Filed: Apr. 8, 2022

(86) PCT No.: PCT/US2022/023950

§ 371 (c)(1),
(2) Date: Oct. 5, 2023

(87) PCT Pub. No.: WO2022/217013

PCT Pub. Date: Oct. 13, 2022

(65) Prior Publication Data

US 2024/0217919 A1 Jul. 4, 2024

Related U.S. Application Data

(60) Provisional application No. 63/172,901, filed on Apr. 9, 2021.

(51) Int. Cl.
*C07C 221/00* (2006.01)
*C07C 225/16* (2006.01)

(52) U.S. Cl.
CPC .......... *C07C 221/00* (2013.01); *C07C 225/16* (2013.01)

(58) Field of Classification Search
CPC ................ C07C 221/00; C07D 203/16; C07D 203/18; C07D 203/20; C07D 291/04
See application file for complete search history.

(56) References Cited

U.S. PATENT DOCUMENTS

| | | | | |
|---|---|---|---|---|
| 4,048,211 | A * | 9/1977 | Barnett | C07C 255/00 558/369 |
| 4,596,807 | A | 6/1986 | Crosby | |
| 5,189,054 | A | 2/1993 | Salituro et al. | |
| 5,593,876 | A | 1/1997 | Stamler et al. | |
| 5,883,115 | A | 3/1999 | Santus et al. | |
| 6,008,258 | A | 12/1999 | Inturrisi | |
| 6,143,933 | A * | 11/2000 | Scheinmann | C12P 41/004 564/317 |
| 6,242,456 | B1 | 6/2001 | Shuster et al. | |
| 9,212,128 | B2 | 12/2015 | Ismail et al. | |
| 9,468,611 | B2 | 10/2016 | Manfredi et al. | |
| 9,855,226 | B2 | 1/2018 | Manfredi et al. | |
| 10,040,752 | B2 | 8/2018 | Mkrtchyan et al. | |
| 2006/0167032 | A1 | 7/2006 | Galer et al. | |
| 2008/0200370 | A1 | 8/2008 | Tseng | |
| 2008/0234352 | A1 | 9/2008 | Fischer et al. | |
| 2009/0156817 | A1 | 6/2009 | Wang et al. | |
| 2009/0185998 | A1 | 7/2009 | Veronese et al. | |
| 2010/0261906 | A1 | 10/2010 | Haar, Jr. et al. | |
| 2010/0292239 | A1* | 11/2010 | Stierli | C07D 207/34 544/242 |
| 2012/0128683 | A1 | 5/2012 | Shantha | |
| 2012/0208747 | A1 | 8/2012 | Kim et al. | |
| 2014/0037721 | A1 | 2/2014 | Liang et al. | |
| 2014/0088155 | A1 | 3/2014 | Manfredi et al. | |
| 2014/0350302 | A1 | 11/2014 | Ismail et al. | |
| 2015/0152081 | A1 | 6/2015 | Kandula | |

(Continued)

FOREIGN PATENT DOCUMENTS

| | | |
|---|---|---|
| CN | 105473135 A | 4/2016 |
| EP | 0914464 A1 | 5/1999 |

(Continued)

OTHER PUBLICATIONS

T Moss et al., 19 Chemistry a European Journal, 3071-3018 (2013) (Year: 2013).*
T. Greene, Greene's Protective Groups in Organic Synthesis, 1-15, 696-771 (4th ed., 2007) (Year: 2007).*
C. Barnett et al., 41 Journal of Organic Chemistry, 710-711 (1976) (Year: 1976).*
Castro et al., 34 Tetrahedron Letters, 4705-4708 (1993) (Year: 1993).*
CAS/CASReact Abstract of J. Castro et al., 34 Tetrahedron Letters, 4705-4708 (1993) (Year: 1993).*
Traynor, K. FDA approves edaravone for amyotrophic lateral sclerosis. Am J Health Syst Pharm. Jun. 15, 2017; 74(12):868.
Trenkwalder, C, Hening WA, Montagna P, Oertel WH, Allen RP, Walters AS, Costa J, Stiasny-Kolster K, Sampaio C. Treatment of restless legs syndrome: an evidence-based review and implications for clinical practice. Mov Disord. Dec. 15, 2008; 23(16):2267-302.

(Continued)

*Primary Examiner* — Alexander R Pagano
(74) *Attorney, Agent, or Firm* — Wood Herron & Evans LLP

(57) ABSTRACT

Methods for the synthesis of enantiopure (S)-methadone, (R)-methadone, (R,S)-methadone and related analogues starting from optically active or racemic N-substituted cyclic sulfamidates, or N-substituted aziridines with retention of stereochemical configuration. The methods avoid the formation of isomethadone-nitrile by-products observed under the previously reported conditions, namely the ring-opening reaction of the corresponding 1,1,2-trimethylaziridin-1-ium salt and the 2,2-diphenylacetonitrile anion, resulting in improved yields and facile purification operations.

9 Claims, 39 Drawing Sheets

(56) References Cited

U.S. PATENT DOCUMENTS

| | | | |
|---|---|---|---|
| 2015/0374684 | A1 | 12/2015 | Javitt |
| 2016/0235691 | A1 | 8/2016 | Mironer |
| 2017/0029432 | A1 | 2/2017 | Trawick et al. |
| 2017/0057909 | A1 * | 3/2017 | Mkrtchyan ........... C07C 221/00 |
| 2018/0214395 | A1 | 8/2018 | Manfredi et al. |
| 2018/0221396 | A1 | 8/2018 | Chadeayne |
| 2020/0277250 | A1 | 9/2020 | Safaei-Ghomi et al. |

FOREIGN PATENT DOCUMENTS

| | | | | |
|---|---|---|---|---|
| WO | 9715294 | A1 | 5/1997 | |
| WO | 199745551 | A1 | 12/1997 | |
| WO | WO-9745551 | A1 * | 12/1997 | ........... C12P 13/001 |
| WO | 9831358 | A1 | 7/1998 | |
| WO | 9849970 | A1 | 11/1998 | |
| WO | 2005072705 | A1 | 8/2005 | |
| WO | 2009092324 | A1 | 7/2009 | |
| WO | 2012014109 | A1 | 2/2012 | |
| WO | 2013077720 | A1 | 5/2013 | |
| WO | 2013168000 | A1 | 11/2013 | |
| WO | 2014052427 | A1 | 4/2014 | |
| WO | 2015192772 | A1 | 12/2015 | |
| WO | 2016103274 | A1 | 6/2016 | |
| WO | 2016118741 | A1 | 7/2016 | |
| WO | 2016191763 | A2 | 12/2016 | |
| WO | 2017035225 | A1 | 3/2017 | |
| WO | 2017035524 | A1 | 3/2017 | |
| WO | WO-2017035224 | A1 * | 3/2017 | ............. A61P 25/04 |
| WO | 2018144551 | A2 | 8/2018 | |
| WO | 2018216018 | A1 | 11/2018 | |
| WO | 201952545 | A1 | 3/2019 | |
| WO | 2020159587 | A1 | 8/2020 | |
| WO | 2020181194 | A1 | 9/2020 | |

OTHER PUBLICATIONS

Trujillo KA, Akil H. Inhibition of morphine tolerance and dependence by the NMDA receptor antagonist MK-801. Science. 1991;251(4989):85-87.

Trujillo KA. Are NMDA receptors involved in opiate-induced neural and behavioral plasticity? A review of preclinical studies. Psychopharmacology (Berl). 2000;151(2-3):121-141.

Trullas, R. et al., "Functional antagonists at the NMDA receptor complex exhibit antidepressant actions," Eur J Pharmacol 1990;185:1-10.

Tsai, MC, Huang TL. Brain-derived neurotrophic factor (BDNF) and oxidative stress in heroin-dependent male patients undergoing methadone maintenance treatment. Psychiatry Res. Dec. 27, 2016; 249:46-50.

Tung, KH et al. Contrasting cardiovascular properties of the μ-opioid agonists morphine and methadone in the rat. Eur J Pharmacol Sep. 5, 2015; 762:372-81.

Turana, Y, Ranakusuma TA, Purba JS, Amir N, Ahmad SA, Machfoed MH, Handayani YS, Asmarinah, Waspadji S. Enhancing Diagnostic Accuracy of aMCI in the Elderly: Combination of Olfactory Test, Pupillary Response Test, BDNF Plasma Level, and APOE Genotype. Int J Alzheimers Dis. 2014; 2014:912586.

Tyler, MP, Hongjie Y, Eric DM et al. GRIN2A mutation and early-onset epileptic encephalopathy: personalized therapy with memantine. Annals of Clinical and Translational Neurology 2014; 1(3):190-198.

Uranagase, A, Katsunuma S, Doi K, Nibu K. BDNF expression in olfactory bulb and epithelium during regeneration of olfactory epithelium. Neurosci Lett. May 10, 2012; 516(1):45-9.

Vaupel, D. Bruce et al., "I-a-Acetylmethadol, I-a-Acetyl-N-normethadol, and I-a-Acetyl-N,N-dinormethadol: Comparisons with Morphone and Methadone in Suppression of the Opioid Withdrawal Syundrome in the Dog," The Journal of Pharmacology and Experimental Therapeutics (1997) 283(2):833-842.

Vink, R. Magnesium in the CNS: recent advances and developments. Magnes Res. Mar. 1, 2016; 29(3):95-101.

Vuong, C et al., The effects of opioids and opioid analogs on animal and human endocrine systems. Endocr Rev. Feb. 2010; 31(1):98-132.

Vogelin, E, Baker JM, Gates J, Dixit V, Constantinescu MA, Jones NF. Effects of local continuous release of brain derived neurotrophic factor (BDNF) on peripheral nerve regeneration in a rat model. Exp Neurol. Jun. 2006; 199(2):348-53.

Wang J, Hajizadeh N, Moore EE, et al. Tissue Plasminogen Activator ((PA) Treatment for Covid-19 Associated Acute Respiratory Distress Syndrome (ARDS): A Case Series [published online ahead of print, Apr. 8, 2020]. J Thromb Haemost. 2020;10.1111/jth.14828.

Wang, GY, Kydd R, Russell BR. Auditory event-related potentials in methadone substituted opiate users. J Psychopharmacol. Sep. 2015; 29(9):983-95.

Wang, GY, Wouldes TA, Kydd R, Jensen M, Russell BR. Neuropsychological performance of methadone-maintained opiate users. J Psychopharmacol. Aug. 2014; 28(8):789-99.

Wang, GY, Wouldes TA, Russell BR. Methadone maintenance treatment and cognitive function: a systematic review. Curr Drug Abuse Rev. Sep. 2013; 6(3):220-30.

Wang, Y et al. Associations between cognitive impairment and motor dysfunction in Parkinson's disease. Brain and Behavior. 2017; 7(6).

Wang, Yiwei, Hailong Liu, Yongzhong Lin, Guangming Liu, Hongwei Chu, Pengyao Zhao, Xiaohan Yang, Tiezheng Zheng, Ming Fan, Xuezhong Zhou, Jun Meng & Changkai Sun. Network-Based Approach to Identify Potential Targets and Drugs that Promote Neuroprotection and Neurorepair in Acute Ischemic Stroke, Nature Scientific Reports, Jan. 2017.

Watanabe, M. et al. (1992) Developmental changes in distribution of NMDA receptor channel subunit mRNAs. Neuroreport 3, 1138-1140.

Welters A, Lammert E, Mayatepek E, Meissner T. Need for Better Diabetes Treatment: The Therapeutic Potential of NMDA Receptor Antagonists. Bessere Diabetesmedikamente sind erforderlich: therapeutisches Potenzial von NMDAR Antagonisten. Klin Padiatr. 2017;229(1):14-20.

White, HD et al., Treatment of pain in fibromyalgia patients with testosterone gel: Pharmacokinetics and clinical response. Int Immunopharmacol. Aug. 2015; 27(2):249-56.

Wickramatilake, CM et al., Association of serum testosterone with lipid abnormalities in patients with angiographically proven coronary artery disease. Indian J Endocrinol Metab. Nov.-Dec. 2013; 17(6):1061-1065.

Willi, TS, Honer WG, Thornton AE, Gicas K, Procyshyn RM, Vila-Rodriguez F, Panenka WJ, Aleksic A, Leonova O1, Jones AA1, MacEwan GW, Barr AM. Factors affecting severity of positive and negative symptoms of psychosis in a polysubstance using population with psychostimulant dependence. Psychiatry Res. Jun. 30, 2016; 240:336-42.

Williams NR, Heifets BD, Blasey C, et al. Attenuation of Antidepressant Effects of Ketamine by Opioid Receptor Antagonism. Am J Psychiatry. 2018;175(12):1205-1215.

Winter CA, Flataker L. Antitussive Action of d-Isomethadone and d-Methadone in Dogs. Proc Soc Exp Biol Med. 1952;81(2):463-465.

Wissel PS, Denke M, Inturrisi CE. A comparison of the effects of a macrobiotic diet and a Western diet on drug metabolism and plasma lipids in man. Eur J Clin Pharmacol. 1987;33(4):403-407.

Wolfensberger, TJ. Macular Edema—Rationale for Therapy. Dev Ophthalmol. 2017; 58:74-86.

Written Opinion in International Patent Application No. PCT/US2018/016159, mailed Jul. 20, 2018, 23 pgs.

Wu et al. "dextro-Morphine attenuates the morphine-produced conditioned place preference via the sigma1 receptor activation in the rat" HHS Public Access. May 21, 2008 (May 21, 2008) <<https://www.nclatnim.nih.govipmc/articles/PMC1936970/?report=classic>> p. 1-11.

Wulff, H et al., Voltage-gated potassium channels as therapeutic drug targets. Nat Rev Drug Discov. Dec. 2009; 8(12):982-1001.

(56) References Cited

OTHER PUBLICATIONS

Wulff, H, Castle NA, Pardo LA. Voltage-gated potassium channels as therapeutic targets. Nat Rev Drug Discov Dec. 2009;8(12):982-1001.
Xiao, Y. et al., "Blockade of Rat a3b4 Nicotinic Receptor Function by Methadone, Its Metabolites, and Structural Analogs," Journal of Pharmacology and Experimental Therapeutics, American Society for Pharmacology and Experimental Therapeutics, US (Oct. 1, 2001) 299(1)366-371.
Yamakura T, Mori H, Masaki H, Shimoji K, Mishina M. Different sensitivities of NMDA receptor channel subtypes to non-competitive antagonists. Neuroreport. 1993;4(6):687-690.
Yang, JC, Rodriguez A, Royston A, Niu YQ, Merve Avar, Ryan Brill, Christa Simon, Jim Grigsby, Randi J. Hagerman, and Olichney JM. Memantine Improves Attentional Processes in Fragile X-Associated Tremor/Ataxia Syndrome: Electrophysiological Evidence from a Randomized Controlled Trial. Sci Rep. 2016; 6:217-19.
Yanik, M et al., Reduced serum brain-derived neurotrophic factor in patients with first onset vitiligo. Neuropsychiatr Dis Treat. Dec. 12, 2014; 10:2361-7.
Yeap, BB. Hormonal changes and their impact on cognition and mental health of ageing men. Maturitas. Oct. 2014; 79(2):227-35.
Yeung, A.W., W. Wu, M. Freewan, R. Stocker, N.J. King, and S.R. Thomas. 2012. Flavivirus infection induces indoleamine 2,3-dioxygenase in human monocyte-derived macrophages via tumor necrosis factor and NF-KB. Journal of Leukocyte Biology 91: 657-666.
Yilmaz, A. et al., "Prolonged effect of an anesthetic dose of ketamine on behavioral despair," Pharmacol Biochem Behav 2002;71:341-344.
Zagon, IS et al., Naltrexone, an opioid antagonist, facilitates reepithelialization of the cornea in diabetic rat. Invest Ophthalmol Vis Sci. Jan. 2000; 41(1):73-81.
Zajecka JM, Stanford AD, Memisoglu A, Martin WF, Pathak S. Buprenorphine/samidorphan combination for the adjunctive treatment of major depressive disorder: results of a phase III clinical trial (Forward-3). Neuropsychiatr Dis Treat. 2019;15:795-808. Published Apr. 4, 2019.
Zanos, P, Moaddel R, Morris PJ, Riggs LM, Highland JN, Georgiou P, Pereira EFR, Albuquerque EX, Thomas CJ, Zarate CA Jr, Gould TD. Ketamine and Ketamine Metabolite Pharmacology: Insights into Therapeutic Mechanisms. Pharmacol Rev. Jul. 2018;70(3):621-660.
Zarate, C. A., Jr. et al., "A Randomized Trial of an N-methyl-D-aspartate Antagonist in Treatment-Resistant Major Depression," Arch Gen Psy 2006;63:856-864.
Zgliczynski, S et al., Effect of testosterone replacement therapy on lipids and lipoproteins in hypogonadal and elderly men. Atherosclerosis. Mar. 1996; 121(1):35-43.
Zhang H, Largent-Milnes TM, Vanderah TW. Glial neuroimmune signaling in opioid reward. Brain Res Bull. 2020;155:102-111.
Zhang, G and Stackman RS Jr. The role of serotonin 5-HT2A receptors in memory and cognition. Front. Pharmacol., Oct. 2015 vol. 6, article 225.
Zhang, N et al., The relationship between endogenous testosterone and lipid profile in middle-aged and elderly Chinese men. European Journal of Endocrinology. (2014) 170:487-494.
Zhou, SF. Polymorphism of human cytochrome P450 2D6 and its clinical significance: Part II. Clin Pharmacokinet. 48:761-804, 2009.
Zhu X, Ye G, Wang Z, Luo J, Hao X. Sub-anesthetic doses of ketamine exert antidepressant-like effects and upregulate the expression of glutamate transporters in the hippocampus of rats. Neurosci Lett. 2017;639:132-137.
https://pubchem.ncbi.nlm.nih.gov/compound/62408.
https://pubchem.ncbi.nlm.nih.gov/compound/9648.
https://pubchem.ncbi.nlm.nih.gov/compound/Dextromethadone.
Huang, L, Bocek M, Jordan JK, Sheehan AH. Memantine for the prevention of primary headache disorders. Ann Pharmacother. Nov. 2014; 48(11):1507-11.
Huang, Y, Dreyfus CF. The role of growth factors as a therapeutic approach to demyelinating disease. Exp Neurol. Sep. 2016; 283(Pt B):531-40.
Hurvich CM, Simonoff JS, and Tsai CL. Smoothing parameter selection in nonparametric regression using an improved Akaike Information Criterion. J R Stat Soc Series B Stat Methodol. 1998;60(2):271-293.
Hutchinson MR, Somogyi AA. (S)-(+)-methadone is more immunosuppressive than the potent analgesic (R)-(−)-methadone. Int Immunopharmacol. 2004;4(12):1525-1530.
Iijima, I. et al., "Studies in the (+)-morphinan series. 4. A markedly improved synthesis of (+)-morphine" Journal of Organic Chemistry. Mar. 1, 1978 (Mar. 1, 1978) vol. 43, p. 1462-1463; p. 1462, col. 1.
Iijima, I. et al., Studies in the (+)-morphinan series. 5. Synthesis and biological properties of (+)-naloxone, J Med Chem. Apr. 1978;21(4):398-400.
Iizuka, A, Nakamura K, Hirai H. Long-term oral administration of the NMDA receptor antagonist memantine extends life span in spinocerebellar ataxia type 1 knock-in mice. Neurosci Lett. Apr. 10, 2015; 592:37-41.
Imam, L, Hannan SA. Noise-induced hearing loss: a modern epidemic? Br J Hosp Med (Lond). May 2, 2017; 78(5):286-290.
International Search Report and Written Opinion in International Patent Application No. PCT/US2013/061639, mailed Nov. 26, 2013, 12 pgs.
International Search Report and Written Opinion in International Patent Application No. PCT/US2019/055590, dated Mar. 13, 2020, 11 pgs.
International Search Report and Written Opinion in International Patent Application No. PCT/US2020/067498, dated Mar. 30, 2021, 14 pgs.
International Search Report and Written Opinion in International Patent Application No. PCT/US2021/023882, mailed Jul. 28, 2021, 9 pgs.
International Search Report and Written Opinion in International Patent Application No. PCT/US2022/023950, dated Jul. 13, 2022, 11 pgs.
International Search Report and Written Opinion in International Patent Application No. PCT/US2022/028559, mailed Jul. 25, 2022, 9 pgs.
International Search Report and Written Opinion in International Patent Application No. PCT/US2022/035255, dated Sep. 26, 2022, 10 pgs.
International Search Report in International Patent Application No. PCT/US2018/016159, mailed Jul. 20, 2018, 12 pgs.
Inturrisi, C.E. et al., Pharmacokinetics and pharmacodynamics of methadone in patients with chronic pain. Clin. Pharm Therap. 41:392-401, 1987.
Inturrisi, C.E., "Opioid Analgesic Therapy in Cancer Pain," Advances in Pain Research and Therapy (Foley, K.M. et al., Eds.) 1990;16:133-154.
Inturrisi, C.E., "Pharmacology of methadone and its isomers," Minerva Anestesiologica 2005;71:435-437.
Inturrisi, C.E., Portenoy, R.K., Max, M.B., Colburn, W.A. and Foley, K.M. Pharmacokinetic pharmacodynamic relationships of methadone infusions in patients with cancer pain. Clin. Pharmacol. Ther. 47:565 577, 1990.
Inturrisi, C.E., Verebely K. The levels of methadone in the plasma in methadone maintenance. Clin Pharmacol Ther. 1972;13(5):633-637.
Inturrisi, CE. NMDA receptors, nitric oxide and opioid tolerance. Regulatory Peptides, 1994, vol. 54, Issue 1.
Isbell H, Eisenman AJ: The addiction liability of some drugs of the methadone series. J Pharmacol Exp Ther. 1948; 93:305-313.
Iseri, PK et al., The effect of memantine in harmaline-induced tremor and neurodegeneration. Neuropharmacology. Sep. 2011; 61(4):715-23.
Ishibashi, H et al. Tool-use learning induces BDNF expression in a selective portion of monkey anterior parietal cortex. Brain Res Mol Brain Res. 2002; 102:110-112.

(56) References Cited

OTHER PUBLICATIONS

Ishikawa, I, Shinno H, Ando N, Mori T, Nakamura Y. The effect of memantine on sleep architecture and psychiatric symptoms in patients with Alzheimer's disease. Acta Neuropsychiatr. Jun. 2016; 28(3):157-64.
Isidori, AM, Balercia G, Calogero AE, Corona G, Ferlin A, Francavilla S, Santi D, Maggi M.Outcomes of androgen replacement therapy in adult male hypogonadism: recommendations from the Italian society of endocrinology. J Endocrinol Invest. Jan. 2015; 38(1):103-12.
Ito, Y, Shimazawa M, Inokuchi Y, Fukumitsu H, Furukawa S, Araie M, Hara H. Degenerative alterations in the visual pathway after NMDA-induced retinal damage in mice. Brain Res. May 30, 2008; 1212:89-101.
Iwaszkiewicz, KS et al., Targeting peripheral opioid receptors to promote analgesic and anti-inflammatory actions. Front Pharmacol 2013; 4:132-137.
Johnson MW, Griffiths RR, Hendricks PS, Henningfield JE. The abuse potential of medical psilocybin according to the 8 factors of the Controlled Substances Act. Neuropharmacology. Nov. 2018;142:143-166.
Jolliet-Riant P, Boukef MF, Duché JC, Simon N, Tillement JP. The genetic variant A of human alpha 1-acid glycoprotein limits the blood to brain transfer of drugs it binds. Life Sci. 1998;62(14):PL219-PL226.
Judd, LL, Janowsky DS, Segal DS, Parker DC, Huey LY. Behavioral effects of methadone in schizophrenic patients. Am J Psychiatry. Feb. 1981; 138(2):243-5.
Kalemenev, SV, Zubareva OE, Sizov VV, Lavrent'eva VV, Lukomskaya NY, Kim KK, Zaitsev AV, Magazanik LG. Memantine attenuates cognitive impairments after status epilepticus induced in a lithium-pilocarpine model. Dokl Biol Sci. Sep. 2016; 470(1):224-227.
Kalev-Zylinska ML, Green TN, Morel-Kopp MC, et al. N-methyl-D-aspartate receptors amplify activation and aggregation of human platelets. Thromb Res. 2014;133(5):837-847.
Kandel, ER (Editor), James H. Schwartz (Editor), Thomas M. Jessell (Editor), Steven A. Siegelbaum (Editor), A. J. Hudspeth (Editor). Principles of Neural Science, Fifth Edition, 2013.
Kang J, Jiang L, Goldman SA, Nedergaard M. Astrocyte-mediated potentiation of inhibitory synaptic transmission. Nat Neurosci. 1998;1(8):683-692.
Kargbo, Psilocybin Therapeutic Research: The Present and Future Paradigm, ACS Medicinal Chemistry Letters, Mar. 2, 2020, vol. 11, pp. 399-402.
Karlsen et al., The EASL-Lancet Liver Commission: protecting the next generation of Europeans against liver disease complications and premature mortality. Lancet 2022; 399: 61-116.
Karolewicz B, Stockmeier CA, Ordway GA. Elevated levels of the NR2C subunit of the NMDA receptor in the locus coeruleus in depression. Neuropsychopharmacology. 2005;30(8):1557-1567.
Katchman, AN et al., Influence of opioid agonists on cardiac human ether-a-go-go-related gene K(+) currents. J Pharmacol Exp Ther. Nov. 2002; 303(2):688-94.
Kempton MJ, Salvador Z, Munafo MR, Geddes JR, Simmons A, Frangou S, Williams SC (2011), "Structural neuroimaging studies in major depressive disorder. Meta-analysis and comparison with bipolar disorder", Archives of General Psychiatry, 68(7):675-690.
Kenakin T, Strachan RT. PAM-Antagonists: A Better Way to Block Pathological Receptor Signaling? Trends Pharmacol Sci. 2018;39(8):748-765.
Kenakin TP, Biased signalling and allosteric machines: new vistas and challenges for drug discovery, Br. J. Pharmacol. 165: 1659-1669, 2012.
Kenakin TP, Overview of receptor interaction of agonists and antagonists, Curr. Protoc. Pharmacol. Chapter 4: Unit 4.1, 2008.
Kernan WN, Viscoli CM, Makuch RW, Brass LM, Horwitz RI. Stratified randomization for clinical trials. J Clin Epidemiol. 1999;52(1):19-26.
Khazaie, H, Najafi F, Ghadami MR, Azami A, Nasouri M, Tahmasian M, Khaledi-Paveh B. Addict Health. Sleep Disorders in Methadone Maintenance Treatment Volunteers and Opium-dependent Patients. Apr. 2016; 8(2):84-89.
Khogali, SE et al., Is glutamine beneficial in ischemic heart disease? Nutrition. Feb. 2002; 18(2):123-6.
Kiang, C-H. et al., "Determination of Acetylmethadol and Metabolites by Use of High-Performance Liquid Chromatography," Journal of Chromatography (1981) 222:81-93.
Kim, HK, Isaacs-Trepanier C, Elmi N, Rapoport SI, Andreazza AC. Mitochondrial dysfunction and lipid peroxidation in rat frontal cortex by chronic NMDA administration can be partially prevented by lithium treatment. J Psychiatr Res. May 2016; 76:59-65.
Kishi T, Matsunaga S, Iwata N. A Meta-Analysis of Memantine for Depression. J Alzheimers Dis. 2017;57(1):113-121. doi:10.3233/JAD-161251.
Kishi T, Matsunaga S, Oya K, Nomura I, Ikuta T, Iwata N. Memantine for Alzheimer's Disease: An Updated Systematic Review and Meta-analysis. J Alzheimers Dis. 2017;60(2):401-425. doi: 10.3233/JAD-170424. PMID: 28922160.
Koch A, Bonus M, Gohlke H, Klöcker N. Isoform-specific Inhibition of N-methyl-D-aspartate Receptors by Bile Salts. Sci Rep. Jul. 11, 2019;9(1):10068.
Konitsiotis, S, Tsironis C, Kiortsis DN, Evangelou A. Effects of N-methyl-D-aspartate receptor antagonism on neuroleptic-induced orofacial dyskinesias. Psychopharmacology (Berl) 2006; 185(3):369-77.
Korde, AS, Maragos WF. Direct exposure to N-methyl-D-aspartate alters mitochondrial function. Neurosci Lett. Jun. 3, 2016; 623:47-51.
Korgaonkar MS, Goldstein-Piekarski AN, Fornito A, Williams LM. Intrinsic connectomes are a predictive biomarker of remission in major depressive disorder, Mol Psychiatry, Nov. 6, 2019.
Kornick, CA et al., QTc interval prolongation associated with intravenous methadone. Pain. Oct. 2003; 105(3):499-506.
Kotermanski SE, Johnson JW. Mg2+ imparts NMDA receptor subtype selectivity to the Alzheimer's drug memantine. J Neurosci. 2009;29(9):2774-2779.
Kovac, JR et al., Testosterone supplementation therapy in the treatment of patients with metabolic syndrome. Postgrad Med. Nov. 2014; 126(7):149-56.
Kraus, C., Kadriu, B., Lanzenberger, R. et al. Prognosis and improved outcomes in major depression: a review. Transl Psychiatry 9, 127 (2019).
Kristensen K, Christensen CB, Christrup LL. The mu1, mu2, delta, kappa opioid receptor binding profiles of methadone stereoisomers and morphine. Life Sci. 1995;56(2):PL45-PL50.
Kritis, AA, Stamoula EG, Paniskaki KA, Vavilis TD. Researching glutamate-induced cytotoxicity in different cell lines: a comparative/collective analysis/study. Front Cell Neurosci. Mar. 17, 2015; 9:91.
Krystal, J.H. et al., "NMDA Agonists and Antagonists as Probes of Glutamatergic Dysfunction and Pharmacotherapies in Neuropsychiatric Disorders," Harv Rev Psych 1999;7(3):125-143.
Ksiazek-Winiarek, DJ, Szpakowski P, Glabinski A. Neural Plasticity in Multiple Sclerosis: The Functional and Molecular Background. Neural Plast. 2015; 2015:307175.
Kubryak OV, Umriukhin AE, Emeljanova IN, et al. Increased ß-endorphin level in blood plasma as an indicator of positive response to depression treatment. Bull Exp Biol Med. 2012;153(5):758-760.
Kuczewski, N et al., Activity-dependent dendritic secretion of brain-derived neurotrophic factor modulates synaptic plasticity. Eur J Neurosci 32:1239-1244.
Kuner T, Schoepfer R. Multiple structural elements determine subunit specificity of Mg2+ block in NMDA receptor channels. J Neurosci. 1996;16(11):3549-3558.
Kussius CL et al., Agonist-specific Gating of NMDA Receptors, Channels (Austin). Author manuscript; available in PMC Aug. 5, 2011.
Kvam TM, Stewart LH, Andreassen OA. Psychedelic drugs in the treatment of anxiety, depression and addiction. Tidsskr Nor Laegeforen. Nov. 12, 2018;138(18).

(56) References Cited

OTHER PUBLICATIONS

Lake, NJ et al., Leigh syndrome: neuropathology and pathogenesis. J Neuropathol Exp Neurol. Jun. 2015; 74(6):482-92.
Lattanzi, Robert et al., "Synthesis and Biological Evaluation of 14-Alkoxymorphinans. 22. Influence of the 14-Alkoxy Group and the Substitution in Position 5 in 14-Alkoxymorphinan-6-ones on in Vitro and in Vivo Activities" J. Med. Chem. 2005, 48, 3372-3378.
Leach K, Sexton PM and Christopoulos A, Allosteric GPCR modulators: taking advantage of permissive receptor pharmacology, Trends Pharmacol. Sci. 28: 382-389, 2007.
Lee, Chia-Hsueh et al., NMDA receptor structures reveal subunit arrangement and pore architecture, Nature. Jul. 10, 2014, 511(7508):191-197.
Lee, Ming-Chak et al., Characterisation of the Expression of NMDA Receptors in Human Astrocytes. PLoS One, Nov. 2010, vol. 5, Issue 11, e14123, 11 pgs.
Leung JC, Marphis T, Craver RD, Silverstein DM. Altered NMDA receptor expression in renal toxicity: Protection with a receptor antagonist. Kidney Int. 2004;66(1):167-176.
Levinson, I, Galynker II, Rosenthal RN. Methadone withdrawal psychosis. J Clin Psychiatry. Feb. 1995; 56(2):73-6.
Li N, Lee B, Liu RJ, et al. mTOR-dependent synapse formation underlies the rapid antidepressant effects of NMDA antagonists. Science. 2010;329(5994):959-964.
Li, W. and Pozzo-Miller L. BDNF deregulation in Rett syndrome. Neuropharmacology 2014:76.
Limapichat, W. et al., Key Binding Interactions for Memantine in the NMDA Receptor, ACS Chemical Neuroscience, 2013, 4, 255-260.
Lindelof, K, Bendtsen L. Memantine for prophylaxis of chronic tension-type headache—a double-blind, randomized, crossover clinical trial. Cephalalgia. Mar. 2009; 29(3):314-21.
Liu, Miao et al., Inhibition of NMDAR Reduces Bladder Hypertrophy and Improves Bladder Function in Cyclophosphamide Induced Cystitis J Urol. May 2015; 193(5): 1676-1683.
Liu, S, Cui J, Niu Z, Yi M, Zhang X, Che F, Ma X. Do obsessive-compulsive disorder and Tourette syndrome share a common susceptibility gene? An association study of the BDNF Val66Met polymorphism in the Chinese Han population. World J Biol Psychiatry. 2015; 16(8):602-9.
Liu, Z. et al., Glutamate release predicts ongoing myocardial ischemia of rat hearts. Scand J Clin Lab Invest. Apr. 19, 2010; 70(3):217-24.
Liu. J. et al. Signaling Defects in iPSC-Derived Fragile X Premutation Neurons. Hum Mol Genet 21, 3795-3805 (2012).
Loix S, De Kock M, and Henin P (2011) The anti-inflammatory effects of ketamine: state of the art. Acta Anaesthesiol Belg 62:47-58.
Lomize, M. et al., OPM database and PPM web server: resources for positioning of proteins in membranes, Nucleic Acids Research, 2012, 40, D370-D376.
Loureiro CM, Shuhama R, Fachim HA, Menezes PR, Del-Ben CM, Louzada-Junior P. Low plasma concentrations of N-methyl-D-aspartate receptor subunits as a possible biomarker for psychosis. Schizophr Res. 2018;202:55-63.
Lovelace MD, Varney B, Sundaram G, et al. Recent evidence for an expanded role of the kynurenine pathway of tryptophan metabolism in neurological diseases. Neuropharmacology. 2017;112(Pt B):373-388.
Low, Chian-Ming et al., New Insights into the Not-So-New NR3 Subunits of N-Methyl-D-aspartate Receptor: Localization, Structure, and Function. Mol Pharmacol 78:1-11, 2010.
Lowe, Stephen L; Wong, Conrad J; Witcher, Jennifer. Safety, tolerability, and pharmacokinetic evaluation of single? and multiple? ascending doses of a novel kappa opioid receptor antagonist. The Journal of Clinical Pharmacology, Sep. 2014, vol. 54, Issue 9.
Lugo-Huitron R, Ugalde Muniz P, Pineda B, Pedraza-Chaverri J, Rios C, Perez-de la Cruz V. Quinolinic acid: an endogenous neurotoxin with multiple targets. Oxid Med Cell Longev. 2013;2013:104024.
Lutz PE, Kieffer BL. Opioid receptors: distinct roles in mood disorders. Trends Neurosci. 2013;36(3):195-206.
Ly C et al., Psychedelics Promote Structural and Functional Neural Plasticity, Cell Rep. Jun. 12, 2018; 23(11):3170-3182.
López-Valdés, HE, Andrew N. Clarkson, Yan Ao, Andrew C. Charles, S. Thomas Carmichael, Michael V. Sofroniew, and K.C. Brennan. Memantine enhances recovery from stroke. Stroke. Jul. 2014; 45(7):2093-2100.
Ma et al., Excessive activation of NMDA receptors in the pathogenesis of multiple peripheral organs via mitochondrial dysfunction, oxidative stress, and inflammation. SN Comprehensive Clinical Medicine (2020) 2:551-569.
Mackay JP, Nassrallah WB, Raymond LA. Cause or compensation?—Altered neuronal Ca2+ handling in Huntington's disease. CNS Neurosci Ther. 2018;24(4):301-310.
Maderuelo. Cristina, Aranzazu Zarzuelo, Jose M Lanao. Critical factors in the release of drugs from sustained release hydrophilic matrices. J. Control. Release, 154 (1) (2011), pp. 2-19.
Maes M, et al. Depressive and anxiety symptoms in the early puerperium are related to increased degradation of tryptophan into kynurenine, a phenomenon which is related to immune activation. Life Sci. 2002; 71:1837-1848.
Moryl, N; Cristina Tamasdan; Dana Tarcatu; Howard T. Thaler; Denise Correa; Richard Steingart; Richard Payne; Eugenie Obbens. A phase I study of d-methadone in patients with chronic pain. Journal of Opioid Management 2016: 12(1):47-55.
Moser T, Starr A. Auditory neuropathy-neural and synaptic mechanisms. Nat Rev Neurol. 2016;12(3):135-149.
Muehlmann, AM, Devine DP. Glutamate-mediated neuroplasticity in an animal model of self-injurious behaviour. Behav Brain Res. May 16, 2008; 189(1):32-40.
Naidu, PSI, Kulkarni SK. Excitatory mechanisms in neuroleptic-induced vacuous chewing movements (VCMs): possible involvement of calcium and nitric oxide. Behav Pharmacol. Jun. 2001; 12(3):209-16.
Nakamura, T. et al., Protein S-Nitrosylation as a Therapeutic Target for Neurodegenerative Diseases. Trends in Pharmacological Sciences, Jan. 2016, vol. 37, No. 1, pp. 73-84.
Nam et al., Activation of Astrocytic μ-Opioid Receptor Causes Conditioned Place Preference, 2019; Cell Reports 28, 1154-1166.
Nam MH, Han KS, Lee J, et al. Expression of μ-Opioid Receptor in CA1 Hippocampal Astrocytes. Exp Neurobiol. 2018;27(2):120-128.
Napoli, I. et al., The fragile X syndrome protein represses activity-dependent translation through CYFIP1, a new 4E-BP. Cell, 2008, 134(6):1042-1054.
Nardelli P, Powers R, Cope TC, Rich MM. Increasing motor neuron excitability to treat weakness in sepsis. Ann Neurol. 2017;82(6):961-971.
Narita M, Hashimoto K, Amano T, et al. Post-synaptic action of morphine on glutamatergic neuronal transmission related to the descending antinociceptive pathway in the rat thalamus. J Neurochem. 2008;104(2):469-478.
Navarrete M, Cuartero MI, Palenzuela R, et al. Astrocytic p38alpha MAPK drives NMDA receptor-dependent long-term depression and modulates long-term memory. Nat Commun. 2019;10(1):2968.
Nelson, Jr., Shawn Daniel. "Synthesis and rapid biological annotation of single-enantiomer small molecules", Doctoral dissertation, 2018, Harvard University, Graduate School of Arts & Sciences. pg <http://Sciences.pg>. 44 para 1 to p. 45, para 1.
Nicholls, DG, Budd SL. Neuronal excitotoxicity: the role of mitochondria. Biofactors. 1998; 8(3-4):287-99.
Nichols, DE et al., "Improvements to the Synthesis of Psilocybin and a Facile Method for Preparing the O-Acetyl Prodrug of Psilocin" Chemistry 1999(6):935-938, 10.1055/s-1999-3490.
Nicoll RA. A Brief History of Long-Term Potentiation. Neuron. 2017;93(2):281-290.
Nicolodi, M, Del Bianco PL, Sicuteri F. Modulation of excitatory amino acids pathway: a possible therapeutic approach to chronic daily headache associated with analgesic drugs abuse. Int J Clin Pharmacol Res. 1997; 17(2-3):97-100.
Nicolodi, M, Sicuteri F. Exploration of NMDA receptors in migraine: therapeutic and theoretic implications. Int J Clin Pharmacol Res. 1995; 15(5-6):181-9.

(56) References Cited

OTHER PUBLICATIONS

Noel, Peter R et General Practitioner Research Panel. "The sulphone analogue of d-methadone: Assessment of antitussive activity in general practice", British Journal of Diseases of the Chest. 1963, vol. 57 No. 1. p. 48-52.
Noruzzadeh, R, Modabbernia A, Aghamollaii V, Ghaffarpour M, Harirchian MH, Salahi S, Nikbakht N, Noruzi N, Tafakhori A. Memantine for Prophylactic Treatment of Migraine Without Aura: A Randomized Double-Blind Placebo-Controlled Study. Headache. Jan. 2016; 56(1):95-103.
Office Action in Australian Patent Application No. 2013323645, dated Jul. 19, 2017, 4 pgs.
Office Action in Australian Patent Application No. 2018215056, dated Feb. 20, 2023, 9 pgs.
Office Action in Canadian Patent Application No. 2,893,238, dated Dec. 5, 2019, 5 pgs.
Office Action in Canadian Patent Application No. 2,893,238, dated Oct. 11, 2018, 6 pgs.
Office Action in Chinese Patent Application No. 201880020508.4, dated Apr. 6, 2022, 9 pgs.
Office Action in Chinese Patent Application No. 201880020508.4, dated May 18, 2023 (English translation included), 13 pgs.
Office Action in Chinese Patent Application No. 201880020508.4, dated Nov. 2, 2022 (English translation Included), 6 pgs.
Office Action in Indian Patent Application No. 201917033638, dated Mar. 24, 2021, 10 pgs.
Office Action in Indian Patent Application No. 202117034376, dated Jan. 6, 2023, 9 pgs.
Office Action in Indian Patent Application No. 3481/DELNP/2015, dated Apr. 25, 2023, 3 pgs.
Office Action in Japanese Patent Application No. 2019-562230, dated Dec. 12, 2022, 6 pgs. (English language translation).
Office Action in Japanese Patent Application No. 2019-562230, dated Jan. 31, 2022, 5 pgs. (English language translation).
Office Action in Japanese Patent Application No. 2019-562230, mailed Sep. 11, 2023, 6 pgs. (English language translation).
Office Action in Korean Patent Application No. 2019-7025398, dated Dec. 23, 2022 (English language translation), 10 pgs.
Office Action in Mexican Patent Application No. MX/a/2019/009038, dated Feb. 14, 2023, 5 pgs.
Office Action in Mexican Patent Application No. MX/a/2019/009038, dated Jul. 14, 2022, 6 pgs.
Office Action in Mexican Patent Application No. MX/a/2019/009038, dated Mar. 2, 2022, 5 pgs. (English language translation).
Office Action in Mexican Patent Application No. MX/a/2019/009038, dated Sep. 5, 2023, 7 pgs (no English language version available).
Office Action in U.S. Appl. No. 13/803,375, dated Apr. 9, 2015, 16 pgs.
Office Action in U.S. Appl. No. 13/803,375, dated Feb. 11, 2016, 12 pgs.
Office Action in U.S. Appl. No. 13/803,375, dated Jun. 2, 2016, 6 pgs.
Office Action in U.S. Appl. No. 15/204,052, dated May 3, 2017, 9 pgs.
Office Action in U.S. Appl. No. 15/884,915, dated Aug. 6, 2019, 11 pgs.
Office Action in U.S. Appl. No. 15/884,915, dated Feb. 7, 2022, 13 pgs.
Office Action in U.S. Appl. No. 15/884,915, dated Jun. 24, 2021, 11 pgs.
Office Action in U.S. Appl. No. 15/884,915, dated Mar. 14, 2019, 11 pgs.
Office Action in U.S. Appl. No. 15/884,915, dated Mar. 19, 2020, 12 pgs.
Office Action in U.S. Appl. No. 15/884,915, dated May 31, 2023, 18 pgs.
Office Action in U.S. Appl. No. 15/884,915, dated Nov. 8, 2022, 17 pgs.
Office Action in U.S. Appl. No. 15/884,915, dated Oct. 22, 2020, 14 pgs.
Office Action in U.S. Appl. No. 17/426,187, dated Aug. 25, 2023, 14 pgs.
Gorman AL et al., The d- and I-isomers of methadone bind to the non-competitive site on the N-methyl-D-aspartate (NMDA) receptor in rat forebrain and spinal cord, Neuroscience Letters 223 (1997) 5-8.
Gorman, A.L. Elliott KJ, Inturrisi CE. The d- and I-isomers of methadone bind to the non-competitive site on the N-methyl-D-aspartate (NMDA) receptor in rat forebrain and spinal cord, Nerurosci Lett 1997. 223:5-8.
Gorman, A.L. et al., The d- and I-isomers of methadone bind to the non-competitive site on the N-methyl-D-aspartate (NMDA) receptor in rat forebrain and spinal cord, Nerurosc iLett, 1997;223:5-8.
Grados, M et al., A selective review of glutamate pharmacological therapy in obsessive-compulsive and related disorders. Psychol Res Behav Manag. 2015; 8:115-131.
Grand T, Abi Gerges S, David M, Diana MA, Paoletti P. Unmasking GluN1/GluN3A excitatory glycine NMDA receptors. Nat Commun. 2018;9(1):4769.
Gregory, CW and Bowen RL. Novel therapeutic strategies for Alzheimer's disease based on the forgotten reproductive hormones. Cell Mol Life Sci. Feb. 2005; 62(3):313-9.
Grevert, P, Masover B, Goldstein A. Failure of Methadone and Levomethadyl Acetate (Levo-Alpha-Acetylmethadol, LAAM) Maintenance to Affect Memory. Arch Gen Psychiatry. Jul. 1977; 34 (7):849-53.
Grilo LS, Carrupt PA, Abriel H. Stereoselective Inhibition of the hERG1 Potassium Channel. Front Pharmacol. Nov. 22, 2010;1:137.
Gross, ER et al., Acute methadone treatment reduces myocardial infarct size via the delta-opioid receptor in rats during reperfusion. Anesth Analg. Nov. 2009; 109(5):1395-402.
Gruber, S. A. et al., "Methadone maintenance Improves Cognitive Performance After Two Months of Treatment," Experimental and Clinical Psychopharmacology (May 2006) 14(2):157-164.
Gudin, JA, Laitman A, Nalamachu S. Opioid Related Endocrinopathy. Pain Med. Oct. 2015; 16 Suppl 1:S9-15.
Guillemin GJ, Quinolinic acid: neurotoxicity, FEBS J. 2012;279(8):1355.
Gutwinski S, Schoofs N, Stuke H, Riemer TG, Wiers CE, Bermpohl F. Opioid tolerance in methadone maintenance treatment: comparison of methadone and levomethadone in long-term treatment. Harm Reduct J. Feb. 16, 2016;13:7.
Gören, MZ et al., F. Cardiovascular responses to NMDA injected into nuclei of hypothalamus or amygdala in conscious rats. Pharmacology. Nov. 2000; 61(4):257-62.
Hackos DH, Hanson JE, Diverse models of NMDA receptor positive allosteric modulation: Mechanisms and consequences, Neuropharmacology, 2017, 112 (Pt A), 34-45.
Haddadi, NS et al., Peripheral NMDA Receptor/NO System Blockage Inhibits Itch Responses Induced by Chloroquine in Mice. Acta Derm Venereol. May 8, 2017; 97(5):571-577.
Halberstadt AL, Geyer MA. Multiple receptors contribute to the behavioral effects of indoleamine hallucinogens. Neuropharmacology. 2011;61(3): 364-381.
Hall, J, Thomas KL, Everitt BJ. Rapid and selective induction of BDNF expression in the hippocampus during contextual learning. Nat Neurosci. 2000; 3:533-535.
Halperin JJ, Heyes MP. Neuroactive kynurenines in Lyme borreliosis, Neurology. 1992;42(1):43-50.
Hama R, Bennett CL. The mechanisms of sudden-onset type adverse reactions to oseltamivir. Acta Neurol Scand. 2017;135(2):148-160.
Han, Da Hee, Low-Dose Naltrexone Decreases Anxiety, Pain, in Patients with Fibromyalgia, ACR/ARHP Annual Meeting 2013.
Han, JC. Rare Syndromes and Common Variants of the Brain-Derived Neurotrophic Factor Gene in Human Obesity. Prog Mol Biol Transl Sci. 2016.
Hanania T, Manfredi P, Inturrisi C, Vitolo OV. The N-methyl-D-aspartate receptor antagonist d-methadone acutely improves depressive-like behavior in the forced swim test performance of rats Exp Clin Psychopharmacol. 2019;10.1037.

(56) References Cited

OTHER PUBLICATIONS

Hani, AJ, Mikati HM, Mikati MA. Genetics of pediatric epilepsy. Pediatr Clin North Am. Jun. 2015; 62(3):703-22.
Hansen K et al., Structure, function, and allosteric modulation of NMDA receptors, Rockefeller University Press, J. Gen. Physiol. 2018 vol. 150 No. 8, 1081-1105.
Hansen, KB, Yi F, Perszyk RE, Furukawa H, Wollmuth LP, Gibb AJ, Traynelis SF. Structure, function, and allosteric modulation of NMDA receptors. J Gen Physiol. Aug. 6, 2018;150(8):1081-1105.
Hanson E. et al., Tonic Activation of GluN2C/GluN2D-Containing NMDA Receptors by Ambient Glutamate Facilitates Cortical Interneuron Maturation, The Journal of Neuroscience, May 8, 2019 39(19):3611-3626.
Hashimoto, K, Koizumi H, Nakazato M, Shimizu E, Iyo M. Role of brain-derived neurotrophic factor in eating disorders: recent findings and its pathophysiological implications. Prog Neuropsychopharmacol Biol Psychiatry. May 2005; 29(4):499-504.
Hashimoto, K; Tomitaka, S; Narita, N; Minabe, Y; Iyo, M; Fukui, S (1996) "Induction of heat shock protein HSP-70 in rat retrosplenial cortex following administration of dextromethorphan". Environmental Toxicology and Pharmacology. 1(4):235-239.
He L, Kim J, Ou C, McFadden W, van Rijn RM, Whistler JL. Methadone antinociception is dependent on peripheral opioid receptors. J Pain. 2009;10(4):369-379.
Heberlein, A. et al. Association of testosterone and BDNF serum levels with craving during alcohol withdrawal. Alcohol 54 (2016) 67-72.
Heinrich, H, Grunitz J, Stonawski V, Frey S, Wahl S,, Albrecht B, Goecke TW, Beckmann MW, Kornhuber J, Fasching PA, Moll GH, Eichler A. Attention, cognitive control and motivation in ADHD: Linking event-related brain potentials and DNA methylation patterns in boys at early school age. Scientific Reports 7, Article No. 3823 (2017).
Henningfield J, Apseloff G, Gorodestsky C, et al. No meaningful opioid abuse liability of REL-1017 (esmethadone; d-methadone), a rapid-acting antidepressant in clinical development: A human abuse potential study. Neuropsychopharmacology. 2021;46(Suppl 1):P315.
Henriques, A, Pitzer C and Schneider A. Neurotrophic growth factors for the treatment of amyotrophic lateral sclerosis: where do we stand? Frontiers in Neuroscience, Jun. 2010 vol. 4 Art 32.
Henssler J, Heinz A, Brandt L, Bschor T. Antidepressant Withdrawal and Rebound Phenomena. Dtsch Arztebl Int. 2019;116(20):355-361.
Hermanussen, M, Tresguerres JA. A new anti-obesity drug treatment: first clinical evidence that, antagonising glutamate-gated Ca2+ ion channels with memantine normalises binge-eating disorders. Econ Hum Biol. Jul. 2005; 3(2):329-37.
Hermes, G, Nagy D, Waterson M, Zsarnovszky A, Varela L, Hajos M, Horvath TL. Role of mitochondrial uncoupling protein-2 (UCP2) in higher brain functions, neuronal plasticity and network oscillation. Mol Metab. Apr. 9, 2016; 5(6):415-21.
Hervé F, Duché JC, d'Athis P, Marché C, Barré J, Tillement JP, Binding of disopyramide, methadone, dipyridamole, chlorpromazine, lignocaine and progesterone to the two main genetic variants of human alpha1-acid glycoprotein: evidence for drug-binding differences between the variants and for the presence of two separate drug-binding sites on alpha1-acid glycoprotein. Pharmacogenetics. 1996;6(5):403-415.
Herzog, AG. Psychoneuroendocrine aspects of temporolimbic epilepsy. Part II: Epilepsy and reproductive steroids. Psychosomatics. Mar.-Apr. 1999; 40(2):102-8.
Hiratsuka M, Takekuma Y, Endo N, Narahara K, Hamdy SI, Kishikawa Y, Matsuura M, Agatsuma Y, Inoue T, Mizugaki M. Allele and genotype frequencies of CYP2B6 and CYP3A5 in the Japanese population. Eur J Clin Pharmacol. Sep. 2002;58(6):417-21.
Ho PS, Yen CH, Chen CY, Huang SY, Liang CS. Changes in cytokine and chemokine expression distinguish dysthymic disorder from major depression and healthy controls. Psychiatry Res. Feb. 2017;248:20-27.
Horrigan, FT and Gilly WF: Methadone block of K+ current in squid giant fiber lobe neurons. J Gen Physiol. Feb. 1, 1996; 107(2):243-260.
Horrigan, FT, et al., Methadone block of K+ current in squid giant fiber lobe neurons. J Gen Physiol. Feb. 1996;107(2):243-60.
Hough C, Morford A, Epel E, Lindqvist D, Saverio Bersani F, Jain F, Mahan L, Ross R, Burke H, Mellon S, Wolkowitz O, Victor Reus V. Pre-Treatment Allostatic Load and Metabolic Dysregulation Predict Antidepressant Response in Major Depressive Disorder. Biological Psychiatry vol. 81, Issue 10, Supplement, May 15, 2017, pp. S405-S406.
Houston, M. The role of magnesium in hypertension and cardiovascular disease. J Clin Hypertens (Greenwich). Nov. 2011; 13(11):843-7.
Howard DM, Adams MJ, Clarke TK, Hafferty JD, Gibson J, Shirali M, et al. (Mar. 2019), "Genome-wide meta-analysis of depression identifies 102 independent variants and highlights the importance of the prefrontal brain regions", Nature Neuroscience, 22 (3): 343-352.
Howell, N. Leber hereditary optic neuropathy: respiratory chain dysfunction and degeneration of the optic nerve. 1988 Vis Res 38:1495-1504.
https://pubchem.ncbi.nlm.nih.gov/compound/10072.
https://pubchem.ncbi.nlm.nih.gov/compound/426183.
https://pubchem.ncbi.nlm.nih.gov/compound/44795.
Extended European Search Report in European Patent Application No. 22785500.4, dated Apr. 2, 2025, 12 pgs.
Sanchack, KE, Thomas CA. Autism Spectrum Disorder: Primary Care Principles. Am Fam Physician. Dec. 15, 2016; 94(12):972-979.
Santiago-Palma, J, Khojainova N, Kornick C, Fischberg DJ, Primavera LH, Payne R and Manfredi P. Intravenous methadone in the management of chronic cancer pain: safe and effective starting doses when substituting methadone for fentanyl. Cancer 2001; 92(7):1919-1925.
Sava A, Formaggio E, Carignani C, Andreetta F, Bettini E, Griffante C. NMDA-induced ERK signalling is mediated by NR2B subunit in rat cortical neurons and switches from positive to negative depending on stage of development. Neuropharmacology. 2012;62(2):925-932.
Schmidt, KG, Bergert H, Funk RH. Neurodegenerative diseases of the retina and potential for protection and recovery. Curr Neuropharmacol. Jun. 2008; 6(2):164-78.
Schuster, R. et al., Elevated methylation and decreased serum concentrations of BDNF in patients in levomethadone compared to diamorphine maintenance treatment. Eur Arch Psychiatry Clin Neurosci 2017; 267:33-40.
Schwarcz R, Bruno JP, Muchowski PJ, Wu HQ. Kynurenines in the mammalian brain: when physiology meets pathology. Nat Rev Neurosci. 2012;13(7):465-477.
Schwarcz R, Stone TW. The kynurenine pathway and the brain: challenges, controversies and promises. Neuropharmacology. 2017;112(Pt B):237-247.
Scirica, BM et al., Effect of ranolazine, an antianginal agent with novel electrophysiological properties, on the incidence of arrhythmias in patients with non-ST-segment elevation acute coronary syndrome: results from the Metabolic Efficiency with Ranolazine for Less Ischemia in Non-ST-Elevation Acute Coronary Syndrome-Thrombolysis in Myocardial Infarction 36 (Merlin-TIMI 36) randomized controlled trial. Circulation. 2007; 116:1647-1652.
Scott CC, Robbins EB, Chen KK: Pharmacologic comparison of the optical isomers of methadone. J Pharm Exp Ther. 1948; 93:282-286.
Seltzman, H. H. et al., "The Preparation of Tritium Labeled Methadone and Its Metabolites," Journal of Labeled Compounds and Radiopharmaceuticals (1981) 18(9):1365-1377.
Shafti, SS et al., Amelioration of deficit syndrome of schizophrenia by norepinephrine reuptake inhibitor. Ther Adv Psychopharmacol 2015, vol. 5(5):263-270.
Shaiova, L, Berger, A., Blinderman, C.D., Bruera, E., Davis, M. P., Derby, S., Inturrisi, C., Kalman, J., Mehta, D., Pappagallo, M., Perlov, E.: Consensus guideline on parenteral methadone use in pain and palliative care. Palliat. Support Care, 6:165-176, 2008.

(56) References Cited

OTHER PUBLICATIONS

Sheets L. Excessive activation of ionotropic glutamate receptors induces apoptotic hair-cell death independent of afferent and efferent innervation. Sci Rep. 2017;7:41102. Published Jan. 23, 2017.
Shim, J. et al., "Consensus 3D Model of u-Opioid Receptor Ligand Efficacy Based on a Quantitative Conformationally Sampled Pharmacophore." Journal of Physical Chemistry B, 2011, 115(22), 7487-7496.
Shimoyama, N. et al., "d-Methadone Is Antinociceptive in the Rat Formalin Test," J Pharma and Exper Therap 1997;283:648-652.
Silver, N. et al., "A 10-year, longitudinal assessment of dopamine agonists and methadone in the treatment of restless legs syndrome," Sleep Medicine, Elsevier, Amsterdam, NI (Nov. 5, 2010) 12(5):440-444.
Skolnick, P. et al., "Adaptation of N-Methyl-D-Aspartate (NMDA) Receptors following Antidepressant Treatment: Implications for the Pharmacotherapy of Depression," Pharmacopsychiatry 1996;29(1):23-26.
Skowronska K, Obara-Michlewska M, Zielinska M, Albrecht J. NMDA Receptors in Astrocytes: In Search for Roles in Neurotransmission and Astrocytic Homeostasis. Int J Mol Sci. 2019;20(2):309.
Slominski, AT. On the Role of the Endogenous Opioid System in Regulating Epidermal Homeostasis. Journal of Investigative Dermatology. 2015; 135:333-334.
Smith, DE et al., Rapamycin and Interleukin-1b Impair Brain-derived Neurotrophic Factor-dependent Neuron Survival by Modulating Autophagy. Jul. 25, 2014 the Journal of Biological Chemistry 289, 20615-20629.
Snyder, F.R., "Methadone and Acetylmethadol: Systematic Versus Differential Effects on Affective States," Pharmacology Biochemistry and Behavior 1986;25(1):310 (Abstract).
Soyka M, Zingg C. Feasability and safety of transfer from racemic methadone to (R)-methadone in primary care: clinical results from an open study. World J Biol Psychiatry. 2009;10(3):217-24.
Soyka, M, Limmer C, Lehnert R, Koller G, Martin G, Küfner H, Kagerer S, Haberthür A. A comparison of cognitive function in patients under maintenance treatment with heroin, methadone, or buprenorphine and healthy controls: an open pilot study. Am J Drug Alcohol Abuse. Nov. 2011; 37(6):497-508.
Sprenger, T, Seifert CL, Miederer M, Valet M, Tölle TR. Successful prophylactic treatment of chronic cluster headache with low-dose levomethadone. J Neurol. Nov. 2008; 255(11):1832-3.
Stanley, BG et al., Lateral hypothalamic NMDA receptors and glutamate as physiological mediators of eating and weight control. Am J Physiol. Feb. 1996; 270(2 Pt 2):R443-9.
Stanne, TM, Åberg ND, Nilsson S, Jood K, Blomstrand C, Andreasson U, Blennow K, Zetterberg H, Isgaard J, Svensson J, Jern C.Low Circulating Acute Brain-Derived Neurotrophic Factor Levels Are Associated With Poor Long-Term Functional Outcome After Ischemic Stroke. Stroke. Jul. 2016; 47(7):1943-5.
Stern P, Behe P, Schoepfer R, Colquhoun D. Single-channel conductances of NMDA receptors expressed from cloned cDNAs: comparison with native receptors. Proc Biol Sci. 1992;250(1329):271-277.
Steuer H, Jaworski A, Elger B, et al. Functional characterization and comparison of the outer blood-retina barrier and the blood-brain barrier. Invest Ophthalmol Vis Sci. 2005;46(3):1047-1053.
Stillman, MJ. Testosterone replacement therapy for treatment refractory cluster headache. Headache. Jun. 2006; 46(6):925-33.
Stringer M, Makina MK, Milesa J, Morleya LS, d-Morphine, but not I-morphine, has low micromolar affinity for the non-competitive N-methyl-D-aspartate site in rat forebrain: Possible clinical implications for the management of neuropathic bain, Neuroscience Letters 295 (2000) 21-24.
Strupp, M, Kremmyda O, Brandt T. Pharmacotherapy of vestibular disorders and nystagmus. Semin Neurol. Jul. 2013; 33(3):286-96.
Studerus E, Kometer M, Hasler F, Vollenweider FX. Acute, subacute and long-term subjective effects of psilocybin in healthy humans: a pooled analysis of experimental studies. J Psychopharmacol. Nov. 2011;25(11):1434-52.
Sullivan, DA et al., Androgen deficiency, Meibomian gland dysfunction, and evaporative dry eye. Ann N Y Acad Sci. Jun. 2002; 966:211-22.
Sun, HM et al. Methadone maintenance treatment program reduces criminal activity and improves social well-being of drug users in China: a systematic review and meta-analysis. BMJ Open. Jan. 8, 2015;5(1).
Sun, X et al., Increasing glutamate promotes ischemia-reperfusion-induced ventricular arrhythmias in rats in vivo. Pharmacology. 2014; 93(1-2):4-9.
Sutter, M, Walter M, Dürsteler KM, Strasser J, Vogel M. Psychosis after Switch in Opioid Maintenance Agonist and Risperidone-Induced Pisa Syndrome: Two Critical Incidents in the Treatment of a Patient with Dual Diagnosis. J Dual Diagn. Dec. 9, 2016:0.
Swanger SA and Traynelis SF. Synaptic Receptor Diversity Revealed Across Space and Time. Trends in Neurosciences, Aug. 2018, vol. 41, No. 8:763-765.
Taiwanese Office Action in Taiwanese Patent Application No. 107108987, dated Dec. 29, 2022, 6 pgs. (English language translation).
Taiwanese Office Action in Taiwanese Patent Application No. 107108987, dated Feb. 11, 2022, 8 pgs. (English translation included).
Takagi Y, Aruga E.New Opioid Options in Japan—Methadone, Tapentadol and Hydromorphone]. Gan To Kagaku Ryoho. Feb. 2018;45(2):205-211.
Takei, N et al., Brain-Derived Neurotrophic Factor Induces Mammalian Target of Rapamycin-Dependent Local Activation of Translation Machinery and Protein Synthesis in Neuronal Dendrites. The Journal of Neuroscience, Nov. 3, 2004 24(44):9760-9769.
Talka, R. et al. Methadone is a Non-Competitive Antagonist at the alpha462 and alpha3 Nicotinic Acetylcholine Receptors and an Agonist at the alpha7 Nicotinic Acetylcholine Receptor, Basic & Clinical Pharmacology & Toxicology, 2015, 116, 321-328.
Tapia-Arancibia, L, Aliaga E, Silhol M, Arancibia S. New insights into brain BDNF function in normal aging and Alzheimer disease. Brain Research Reviews 2008. 59(1):201-20.
Tauboll, E et al., Interactions between hormones and epilepsy. Seizure. May 2015; 28:3-11.
Teng H, Cai W, Zhou L, Zhang J, Liu Q, Wang Y, et al. (2010) Evolutionary Mode and Functional Divergence of Vertebrate NMDA Receptor Subunit 2 Genes. PLoS ONE 5(10).
Tennant, F. S. Jr., "(-)-a-Acetylmethadol for Treatment of Chronic Pain Patients who Abuse Opioids," Drug and Alcohol Dependence 1983;12:243-247.
Terenius, L., "A Rapid Assay of Affinity for the Narcotic Receptor in Rat Brain: Application to Methadone Analogues," Acta pharmacol. et toxicol. (1974) 34:88-91.
Tonacci, A, Borghini A, Mercuri A, Pioggia G, Andreassi MG. Brain-derived neurotrophic factor (Val66Met) polymorphism and olfactory ability in young adults. J Biomed Sci. Aug. 7, 2013; 20:57. doi: 10.1186/1423-0127-20-57.
Tornoe CW, Gamett CE, Wang Y, Florian J, Li M, Gobburu JV. Creation of a knowledge management system for QT analyses. J Clin Pharmacol. 2011;51(7):1035-1042.
Toskulkao T, Pornchai R, Akkarapatumwong V, Vatanatunyakum S, Govitrapong P. Alteration of lymphocyte opioid receptors in methadone maintenance subjects. Neurochem Int. 2010;56(2):285-290.
Magdalon, J et al. "Dysfunctional mTORC1 Signaling: A Convergent Mechanism between Syndromic and Nonsyndromic Forms of Autism Spectrum Disorder?" Ed. Merlin G. Butler. International Journal of Molecular Sciences 18.3 (2017): 659. PMC. Web. Aug. 21, 2017.
Mahachoklertwattana, P et al., N-methyl-D-aspartate (NMDA) receptors mediate the release of gonadotropin-releasing hormone (GnRH) by NMDA in a hypothalamic GnRH neuronal cell line (GT1-1). Endocrinology. Mar. 1994; 134(3):1023-30.
Mahaling, DU et al., Comparison of lipid profile in different grades of non-alcoholic fatty liver disease diagnosed on ultrasound. Asian Pac J Trop Biomed. Nov. 2013; 3(11):907-912.
Maneckjee R, Minna JD. Characterization of methadone receptor subtypes present in human brain and lung tissues. Life Sci. 1997;61(22).
Manfredi, PL and Houde RW. Prescribing Methadone, A Unique Analgesic. J Supp Oncology 2003. 1(3):216-219.

(56) References Cited

OTHER PUBLICATIONS

Manfredi, PL et al., "Intravenous methadone for cancer pain unrelieved by morphine and hydromorphone: clinical observations," Pain 1997;70:99-101.
Manfredi, PL et al., "Methadone Analgesia in Cancer Pain Patients on Chronic Methadone Maintenance Therapy," J Pain Sympt Manag 2001;21(2):169-174.
Manfredi, PL, Breuer B, Wallenstein S, Stegmann M, Bottomley G and Libow L. Opioid Treatment for Agitation in Patients with Advanced Dementia. Int J Ger Psy 2003; 18:700-705.
Manfredi, PL, Breuer BB, Meier DM and Libow L. Pain Assessment in Elderly Patients with Severe Dementia. J Pain Sympt Manag 2003; 25(1):48-52.
Manfredi, PL, Foley KM, Payne R, Inturrisi CE and Houde R. Parenteral Methadone: an Essential Medication for the Treatment of Pain. J Pain Sympt Manage 2003; 26:687-8.
Manfredi, PL, Gonzales GR and Payne R. Reversible spastic paraparesis induced by high-dose intravenous methadone. J Pain. Feb. 2001; 2(1):77-79.
Manfredi, PL, Shreier G, Ling T. Cancer Pain. In Pappagallo M., ed. The Neurological Basis of Pain. McGraw-Hill. Dec. 2004.
Manfredi, PL. Methadone for cancer pain. [Letter]. Pain 1998; 77:103-104.
Manfredi, PL. Opioids versus antidepressants in postherpetic neuralgia: A randomized placebo-controlled trial. [Letter]. Neurology. Neurology. Mar. 25, 2003; 60(6):1052-3.
Mannaioni G, Lanzi C, Lotti M, et al. Methadone Dose Adjustments, Plasma R-Methadone Levels and Therapeutic Outcome of Heroin Users: A Randomized Clinical Trial. Eur Addict Res. 2018;24(1):9-18.
Marco S, Giralt A, Petrovic MM, et al. Suppressing aberrant GluN3A expression rescues synaptic and behavioral Impairments in Huntington's disease models. Nat Med. 2013; 19(8):1030-1038.
Marimuthu, P, Varadarajan S, Krishnan M, Shanmugam S, Kunjuraman G, Ravinder JR, Arumugam B, Alex D, Swaminathan P. Evaluating the efficacy of memantine on improving cognitive functions in epileptic patients receiving anti-epileptic drugs: A double-blind placebo-controlled clinical trial (Phase IIIb pilot study). Ann Indian Acad Neurol. Jul.-Sep. 2016; 19(3):344-50.
Marmor, M et al., Coronary artery disease and opioid use. Am J Cardiol. May 15, 2004; 93(10):1295-7.
Martin, HGS and Yu Tian W. Blocking the Deadly Effects of the NMDA Receptor in Stroke. Cell 140, Jan. 22, 2010.
Martins, LB, Duarte H, Ferreira AV, Rocha NP, Teixeira AL, Domingues RB. Migraine is associated with altered levels of neurotrophins. Neurosci Lett. Feb. 5, 2015; 587:6-10.
Marvanova, M. et al. The Neuroprotective Agent Memantine Induces Brain-Derived Neurotrophic Factor and trkB Receptor Expression in Rat Brain. Molecular and Cellular Neuroscience 2001; 18:247-258.
Matsui A, Williams JT. Activation of μ-opioid receptors and block of KIR3 potassium channels and NMDA receptor conductance by I- and d-methadone in rat locus coeruleus. Br J Pharmacol. 2010;161(6):1403-1413.
Mayo Clinic Autism Spectrum Disorder (2018 <https://www.nnayoclinic.org/diseases-conditions/autisnn-spectrum-disorder/> symptoms-causes/syc-20352928?p=1). (Year: 2018).
Mazinani, R, Nejati S, Khodaei M. Effects of memantine added to risperidone on the symptoms of schizophrenia: A randomized double-blind, placebo-controlled clinical trial. Psychiatry Res. Jan. 2017; 247:291-295.
McDole, B, Isgor C, Pare C, Guthrie K. BDNF over-expression increases olfactory bulb granule cell dendritic spine density in vivo. Neuroscience. Sep. 24, 2015; 304:146-60.
McGee MA, Abdel-Rahman AA. N-Methyl-D-Aspartate Receptor Signaling and Function in Cardiovascular Tissues. J Cardiovasc Pharmacol. 2016;68(2):97-105.
McLennan, Y et al., Fragile X Syndrome. Curr Genomics. May 2011; 12(3):216-224.
Mealing GA, Lanthorn TH, Murray CL, Small DL, Morley P. Differences in degree of trapping of low-affinity uncompetitive N-methyl-D-aspartic acid receptor antagonists with similar kinetics of block. J Pharmacol Exp Ther. 1999;288(1):204-210.
Mealing GA, Lanthorn TH, Small DL, et al. Structural modifications to an N-methyl-D-aspartate receptor antagonist result in large differences in trapping block. J Pharmacol Exp Ther. 2001;297(3):906-914.
Meisner, Falko et al. for the German Competence Network HIV/AIDS. Memantine Upregulates BDNF and Prevents Dopamine Deficits in SIV-Infected Macaques: A Novel Pharmacological Action of Memantine. Neuropsychopharmacology (2008) 33, 2228-2236.
Meuldijk, R, Colon EJ. Methadone treatment of Tourette's disorder. Am J Psychiatry. Jan. 1992; 149(1):139-40.
Miglio G, Varsaldi F, Lombardi G. Human T lymphocytes express N-methyl-D-aspartate receptors functionally active in controlling T cell activation. Biochem Biophys Res Commun. 2005;338(4):1875-1883.
Milenkovic VM, Stanton EH, Nothdurfter C, Rupprecht R, Wetzel CH, The Role of Chemokines in the Pathophysiology of Major Depressive Disorder, Int J Mol Sci. 2019; 20(9):2283.
Mischoulon, D et al., Randomized, proof-of-concept trial of low dose naltrexone for patients with breakthrough symptoms of major depressive disorder on antidepressants. J Affect Disord. Jan. 15, 2017; 208:6-14.
Mitchell, T.B. et al., "Subjective and physiological responses among racemic-methadone maintenace patients in relation to relative (S)- vs. (R)-methadone exposure," Br J Clin Pharmacol 2004;58(6):609-617.
Mohammadi, MR, Mohammadzadeh S, Akhondzadeh S. Memantine versus Methylphenidate in Children and Adolescents with Attention Deficit Hyperactivity Disorder: A Double-Blind, Randomized Clinical Trial.Iran J Psychiatry. Apr. 2015; 10(2):106-14.
Molassiotis, A, Smith JA, Bennett MI, Blackhall F, Taylor D, Zavery B, Harle A, Booton R, Rankin EM, Lloyd-Williams M, Morice AH. Clinical expert guidelines for the management of cough in lung cancer: report of a UK task group on cough. Cough. Oct. 6, 2010; 6:9.
Monaghan DT, Jane DE. Pharmacology of NMDA Receptors. In: Van Dongen AM, editor. Biology of the NMDA Receptor. Boca Raton (FL): CRC Press/Taylor & Francis; 2009. Chapter 12.
Monaghan DT, Larsen H. NR1 and NR2 subunit contributions to N-methyl-D-aspartate receptor channel blocker pharmacology. J Pharmacol Exp Ther. 1997;280(2):614-620.
Monyer, H. et al. (1994) Developmental and regional expression in the rat brain and functional properties of four NMDA receptors. Neuron 12, 529-540.
Moore JX, Chaudhary N, Akinyemiju T. Metabolic Syndrome Prevalence by Race/Ethnicity and Sex in the United States, National Health and Nutrition Examination Survey, 1988-2012. Prev Chronic Dis 2017;14:160287.
Moravcova et al., The effect of oleic and palmitic acid on induction of steatosis and cytotoxicity on rat hepatocytes in primary culture. Physiol Res 2015;64(Suppl 5):S627-36.
Morley, JE. Pharmacologic Options for the Treatment of Sarcopenia. Calcif Tissue Int. Apr. 2016; 98(4):319-3.
Morley, JS, Watt JW, Wells JC, Miles JB, Finnegan MJ, Leng G. Methadone in pain uncontrolled by morphine. Lancet. Nov. 13, 1993; 342(8881):1243.
Morrison, KE et al., Distinct profiles of social skill in adults with autism spectrum disorder and schizophrenia. Autism Res. May 2017; 10(5):878-887.
Morrison, RS, Carney MT and Manfredi PL. Pain Management. In: Rosenthal RA, Zenilman ME, Katlic MR, eds. Principles and Practice of Geriatric Surgery. New York: Springer; 2001:160-173.
Moryl, N et al., A phase I study of D-methadone in patients with chronic pain, Journal of Opioid Management 12:1, Jan.-Feb. 2016.
Moryl, N, Santiago-Palma J, Kornick C, Derby S, Fischberg D, Payne R, Manfredi P. Pitfalls of opioid rotation: substituting another opioid for methadone in patients with cancer pain. Pain 2002; 96(3):325-328.

(56) References Cited

OTHER PUBLICATIONS

Moryl, N. et al., "Pitfalls of opioid rotation: substituting another opioid for methadone in patients with cancer pain," Pain 2002;96(3):325-328.
Moryl, N. et al., A Phase I/II Study of D-Methadone in Patients with Chronic Pain—Therapeutic/Diagnostic Protocol, Memorial Sloan-Kettering Cancer Center (2008) IRB#: 01-017A(12):1-28.
Zoghbi, HY et al., Cerebrospinal fluid biogenic amines and biopterin in Rett syndrome. Annals of Neurology. 25(1):56-60.
Zott B, Simon MM, Hong W, et al. A vicious cycle of ß amyloid-dependent neuronal hyperactivation. Science. 2019;365(6453):559-565.
Du, J. et al., Glutamate in peripheral organs: Biology and pharmacology. European Journal of Pharmacology 784 (2016) 42-48.
Duchen, MR. Mitochondria, calcium-dependent neuronal death and neurodegenerative disease. Pflugers Arch. 2012: 464(1):111-121.
Dupre, D. J. et al., "Analgesics. I. Esters and ketones derived from alpha-amino-w-cyano-ww-diarylalkanes." Journal of the Chemical Society 1949, 500-510.
Eap CB, Cuendet C, Baumann P. Binding of d-methadone, I-methadone, and dl-methadone to proteins in plasma of healthy volunteers: role of the variants of alpha1-acid glycoprotein. Clin Pharmacol Ther. Mar. 1990;47(3):338-46.
Egan, MF, et al. The BDNF val66met polymorphism affects activity-dependent secretion of BDNF and human memory and hippocampal function. Cell. 2003; 112:257-269.
Eleti, S. Drugs in Alzheimer's disease Dementia: An overview of current pharmacological management and future directions. Psychiatr Danub. Sep. 2016;28(Suppl-1):136-140.
Elkader, A.K. et al., "Major Depressive Disorder and Patient Satisfaction in Relation to Methadone Pharmacokinetics and Pharmacodynamics in Stabilized Methadone Maintenance Patients," Journal of Clinical Psychopharmacology 2009;29(1):77-81.
Elnagar MR, Walls AB, Helal GK, Hamada FM, Thomsen MS, Jensen AA. Probing the putative alpha7 nAChR/NMDAR complex in human and murine cortex and hippocampus: Different degrees of complex formation in healthy and Alzheimer brain tissue. PLoS One. 2017;12(12):e0189513. Published Dec. 20, 2017.
Elvira et al., Covalent Polymer-Drug Conjugates, Molecules, Jan. 31, 2005, vol. 10, pp. 114-125.
Erhardt S, Lim CK, Linderholm KR, et al. Connecting inflammation with glutamate agonism in suicidality. Neuropsychopharmacology. 2013;38(5):743-752.
Erickson, KI, Prakash RS, Voss MW, Chaddock L, Heo S, McLaren M, Pence BD, Martin SA, Vieira VJ, Woods JA, McAuley E, Kramer AF. Brain-derived neurotrophic factor is associated with age-related decline in hippocampal volume. The Journal of Neuroscience 2010. 30(15):5368-75.
Esfahani, MR et al., Memantine for axonal loss of optic neuritis. Graefes Arch Clin Exp Ophthalmol. Jun. 2012; 250(6):863-9.
Estienne, MJ, Barb CR.Modulation of growth hormone, luteinizing hormone, and testosterone secretion by excitatory amino acids in boars. Reprod Biol. Mar. 2002; 2(1):13-24.
European extended Search Report in European Patent Application No. 19913054.3, dated Sep. 23, 2022, 5 pgs.
European Official Action in European Patent Application No. 18706021.5, dated Jan. 4, 2022, 4 pgs.
Euser, AG. Cipolla MJ. Magnesium sulfate for the treatment of eclampsia: a brief review. Stroke. Apr. 2009; 40(4):1169-75.
Fakhri, A, Pakseresht S, Haghdoost MR, Hekmatkhah N, Torkashvand M, Ghorbanzadeh B. Memantine Enhances the Effect of Olanzapine in Patients with Schizophrenia: A Randomized, Placebo-Controlled Study. Acta Med Iran. Nov. 2016; 54(11):696-703.
Farinelli, I, De Filippis S, Coloprisco G, Missori S, Martelletti P. Future drugs for migraine. Intern Emerg Med. Oct. 2009; 4(5):367-73.
Fava M, Freeman MP, Flynn M, et al. Double-blind, placebo-controlled, dose-ranging trial of intravenous ketamine as adjunctive therapy in treatment-resistant depression (TRD) Mol Psychiatry 2018.
Fava M, Stahl S, Pani L, De Martin S, Pappagallo M, Guidetti C, Alimonti A, Bettini E, Mangano RM, Wessel T, de Somer M, Caron J, Vitolo OV, DiGuglielmo GR, Gilbert A, Mehta H, Kearney M, Mattarei A, Gentilucci M, Folli F, Traversa S, Inturrisi CE, Manfredi PL. REL-1017 (Esmethadone) as Adjunctive Treatment in Patients With Major Depressive Disorder: A Phase 2a Randomized Double-Blind Trial. Am J Psychiatry. Feb. 2022;179(2):122-131.
Feinberg, DT, Hartman N. Methadone and schizophrenia. [Letter]. Am J Psychiatry. Dec. 1991; 148(12):1750-1.
Fellin T, Pascual O, Gobbo S, Pozzan T, Haydon PG, Carmignoto G. Neuronal synchrony mediated by astrocytic glutamate through activation of extrasynaptic NMDA receptors [published correction appears in Neuron. Jan. 6, 2005;45(1):177]. Neuron. 2004;43(5):729-743.
Fernandes, C. et al., Development of a PEGylated-Based Platform for Elcient Delivery of Dietary Antioxidants Across the Blood-Brain Barrier, Bioconjugate Chem, 2018, 29, 1677-1689.
Fernandez CA, Smith C, Yang W, et al. Concordance of DMET plus genotyping results with those of orthogonal genotyping methods. Clin Pharmacol Ther. 2012;92:360-365.
Finsterer, J. Mitochondrial disorders, cognitive impairment and dementia. J Neurol Sci. Aug. 15, 2009; 283(1-2):143-8.
Fjelldal, M. F., "Properties of glutamate receptor subunit GluN2B antagonists and effects of prenatal opioid exposure—studies in chicken and rat," Sep. 2019, pp. 1-68.
Flory, JH, Wiesenthal AC, Thaler HT, Koranteng L, Moryl N. Methadone Use and the Risk of Hypoglycemia for Inpatients with Cancer Pain. Journal of pain and symptom management. 2016; 51(1):79-87.
Fogaça MV, Fukumoto K, Franklin T, et al. N-Methyl-D-aspartate receptor antagonist d-methadone produces rapid, mTORC1-dependent antidepressant effects. Neuropsychopharmacology. 2019;44(13):2230-2238.
Forcelli PA, Turner JR, Lee BG, et al. Anxiolytic- and antidepressant-like effects of the methadone metabolite 2-ethyl-5-methyl-3,3-diphenyl-1-pyrroline (EMDP). Neuropharmacology. 2016; Sep. 12, 2015.
Foster DJR, Somogyi AA, White JM, et al. Population pharmacokinetics of (R)-, (S)- and rac-methadone in methadone maintenance patients. Br J Clin Pharmacol. 2004;57:742-755.
Frank, Raw et al., Hierarchical organization and genetically separable subfamilies of PSD95 postsynaptic supercomplexes. J Neurochem. Aug. 2017;142(4):504-511.
Fraser, HF et al., Human pharmacology and addictiveness of certain dextroisomers of synthetic analgesics, United Nations Office on Drugs and Crime, of the National Institute of Mental Health, Addiction Research Center, U.S. Public Health Service, Lexington, KY, Jan. 1, 1962, pp. 25-35.
Fraysse, B, Nagi SM, Boher B et al. Ca2+ overload and mithocondrial permeability transition pore activation in living delta-sarcoglycan-deficient cardiomyocites. Am J Physiol 2010; 299 (3): 1158-1166.
Froimowitz, M., "Conformation-Activity Study of Methadone and Related Compounds," J. Med. Chem. (1982) 25:689-696.
Frontera, JL, Cervino AS, Jungblut LD, Paz DA. Brain-derived neurotrophic factor (BDNF) expression in normal and regenerating olfactory epithelium of Xenopus laevis. Ann Anat. Mar. 2015; 198:41-8.
Frye, CA. Effects and mechanisms of progestogens and androgens in ictal activity. Epilepsia. Jul. 2010; 51 Suppl 3:135-40.
Fuziwara, S et al., NMDA-type glutamate receptor is associated with cutaneous barrier homeostasis. J Invest Dermatol. Jun. 2003; 120(6):1023-9.
Gabrielsen, JS et al.,Trends in Testosterone Prescription and Public Health Concerns. Urol Clin North Am. May 2016; 43(2):261-71.
Gannon, M, Che P, Chen Y, Jiao K, Roberson ED, and Wang Q. Noradrenergic dysfunction in Alzheimer's disease. Front Neurosci. 2015; 9:220.
Garnett C, Bonate PL, Dang Q, Ferber G, Huang D, Liu J, et al. Scientific white paper on concentration-QTc modeling. [published correction appears in J Pharmacokinet Pharmacodyn. 2018;45(3):399]. J Pharmacokinet Pharmacodyn. 2018;45(3):383-397.
Garrido MJ, Aguirre C, Trocóniz IF, Marot M, Valle M, Zamacona MK, Calvo R. Alpha1-acid glycoprotein (AAG) and serum protein

(56) References Cited

OTHER PUBLICATIONS binding of methadone in heroin addicts with abstinence syndrome. Int J Clin Pharmacol Ther. Jan. 2000;38(1):35-40.
Garrido MJ, Jiminez R, Gomez E, Calvo R. Influence of plasma-protein binding on analgesic effect of methadone in rats with spontaneous withdrawal. J Pharm Pharmacol. 1996;48(3):281-284.
Gautam S, Ukawala R, Dhoot H, Jain S. Design and characterization of controlled release tablet of metoprolol. J. Pharm. Bioall. Sci., 4 (5) (2012), p. 90.
Gerber JG, Rhodes RJ, Gal J. Stereoselective metabolism of methadone N-demethylation by cytochrome P4502B6 and 2C19. Chirality. 2004;16:36-44.
Geremia, NM, Pettersson LM, Hasmatali JC, Hryciw T, Danielsen N, Schreyer DJ, Verge VM. Endogenous BDNF regulates induction of intrinsic neuronal growth programs in injured sensory neurons. Exp Neurol. May 2010; 223(1):128-42.
Ghasemi, M, Schachter SC. The NMDA receptor complex as a therapeutic target in epilepsy: a review. Epilepsy Behav. Dec. 2011; 22(4):617-40.
Gill, SS. and Pulido OM. Glutamate Receptors in Peripheral Tissues: Current Knowledge, Future Research and Implications for Toxicology. Toxicologic Pathology 2001; 29(2):208-223.
Glaser, R, et al., Testosterone pellet implants and migraine headaches: a pilot study. Maturitas. Apr. 2012, 71(4):385-8.
Glass, MJ et al., NMDA Receptor Plasticity in the Hypothalamic Paraventricular Nucleus Contributes to the Elevated Blood Pressure Produced by Angiotensin II. Journal of Neuroscience, 2015, 35(26):9558-9567.
Glue, P, Cape G, Tunnicliff D, Lockhart M, Lam F, Gray A, Hung N, Hung CT, Harland S, Devane J, Howes J, Weis H, Friedhoff L. Switching Opioid-Dependent Patients From Methadone to Morphine: Safety, Tolerability, and Methadone Pharmacokinetics. Clin Pharmacol. Aug. 2016; 56(8):960-5.
"Coronavirus, i tossicodipendenti sembrano immuni: l'ipotesi degli esperti di Villa Maraini-Cri" Il Messaggero, May 4, 2020, Caltagirone Editore.
Abe, Koji et al. "Confirmatory Double-Blind, Parallel-Group, Placebo-Controlled Study of Efficacy and Safety of Edaravone (MCI-186) in Amyotrophic Lateral Sclerosis Patients." Amyotrophic Lateral Sclerosis & Frontotemporal Degeneration 15.7-8 (2014): 610-617.
Abramson FP. Methadone plasma protein binding: alterations in cancer and displacement from alpha1-acid glycoprotein. Clin Pharmacol Ther. 1982;32(5):652-658.
Ahmed, A and Simmons Z. Pseudobulbar affect: prevalence and management. Therapeutics and Clinical Risk Management 2013; 9:483-489.
Ahmed, A. et al., Pseudobulbar affect: prevalence and management. Therapeutics and Clinical Risk Management 2013;9:483-489.
Allen, RP, Barker PB, Horska DA, Earley CJ. Thalamic glutamate/glutamine in restless legs syndrome. Neurology 2013; 80:2028-2034.
Almatroudi, A. et al., "Combined adminsitration of buprenorphine and naltrexone produces antidepressant-like effects in mice," Journal of Psychopharmacology (2015) 29(7):812-821.
Alsemari, A. Hypogonadism and neurological diseases. Neurol Sci. May 2013; 34(5):629-38.
Andreassen, CS, Jakobsen J, Flyvbjerg A, Andersen H. Expression of neurotrophic factors in diabetic muscle-relation to neuropathy and muscle strength. Brain. Oct. 2009; 132 (Pt 10):2724-33.
Andreassen, OA, Aamo, TO and Jorgensen, HA. Inhibition by memantine of the development of persistent oral dyskinesias induced by long-term haloperidol treatment of rats. British Journal of Phamacology. 1996; 119:751-757.
Andreassen, OA, Waage J, Finsen B, Jørgensen HA. Memantine attenuates the increase in striatal preproenkephalin mRNA expression and development of haloperidol-induced persistent oral dyskinesias in rats. Brain Res. 2003; 24; 994(2):188-92.
Anitha, M, Nandhu MS, Anju TR, Jes P, Paulose CS. Targeting glutamate mediated excitotoxicity in Huntington's disease: neural progenitors and partial glutamate antagonist—memantine. Med Hypotheses. Jan. 2011; 76(1):138-40.
Arnone D, McIntosh AM, Ebmeier KP, Munafò MR, Anderson IM (2012). "Magnetic resonance imaging studies in unipolar depression: systematic review and meta-regression analyses". European Neuropsychopharmacology. 22 (1): 1-16.
Asp, L., A.S. Johansson, A. Mann, B. Owe-Larsson, E.M. Urbanska, T. Kocki, M. Kegel, G. Engberg, G.B. Lundkvist, and H. Karlsson. 2011. Effects of pro-inflammatory cytokines on expression of kynurenine pathway enzymes in human dermal fibroblasts. Journal of Inflammation 8: 25.
Attems, J et al., Olfaction and Aging: A Mini-Review. Gerontology. 2015; 61(6):485-90.
Australian Office Action in Australian Patent Application No. 2013323645, dated Jul. 19, 2017, 4 pgs.
Australian Office Action in Australian Patent Application No. 2018215056, dated Feb. 20, 2023, 9 pgs.
Axelrod, FB. Familial dysautonomia. Muscle & Nerve 2004; 29(3):352-363.
Bach, TV, Pan J, Kirstein A, Grief CJ, Grossman D. Use of Methadone as an Adjuvant Medication to Low-Dose Opioids for Neuropathic Pain in the Frail Elderly: A Case Series. J Palliat Med. Dec. 2016; 19(12):1351-1355.
Bai, X, Zhang C, Chen A, Liu W, Li J, Sun Q, Wang H. Protective Effect of Edaravone on Glutamate-Induced Neurotoxicity in Spiral Ganglion Neurons. Neural Plast 2016; Article ID 4034218, 10 pgs.
Banaschewski T., Becker K., Scherag S., Franke B. & Coghil, D. Molecular genetics of attention deficit/hyperactivity disorder. an overview. Eur. Child Adolesc. Psychiatry 19, 237-257 (2010).
Banerjee, A, Larsen RS, Philpot BD, Paulsen O. Roles of Presynaptic NMDA Receptors in Neurotransmission and Plasticity. Trends in Neurosciences, 2015, vol. 39, Issue 1.
Banke TG, Traynelis SF. Activation of NR1/NR2B NMDA receptors. Nat Neurosci. 2003;6(2):144-152.
Bannai H, Niwa F, Sherwood MW, Shrivastava AN, Arizono M, Miyamoto A, Sugiura K, Lévi S, Triller A, Mikoshiba K. Bidirectional control of synaptic GABAAR clustering by glutamate and calcium. Cell reports. Dec. 29, 2015;13(12):2768-80.
Bart, G et al., Methadone and the QTc Interval: Paucity of Clinically Significant Factors in a Retrospective Cohort. Journal of Addiction Medicine 2017. 11(6):489-493.
Bartus, RT, Bétourné A, Basile A, Peterson BL,Glass J, Boulis NM. Beta2-Adrenoceptor agonists as novel, safe and potentially effective therapies for Amyotrophic lateral sclerosis (ALS) Neurobiology of Disease 85 (2016) 11-24.
Bathina, S. et al., "Brain-derived neurotrophic factor and its clinical implications," Arch Med Sci 2015; 11, 6: 1164-1178.
Bathina, S. et al., BDNF protects pancreatic b cells (RIN5F) against cytotoxic action of alloxan, streptozotocin, doxorubicin and benzo(a)pyrene in vitro. Metabolism. May 2016; 65(5):667-84.
Bauer, J, Werner A, Kohl W, Kugel H, Shushakova A, Pedersen A, Ohrmann P.Hyperactivity and impulsivity in adult attention deficit/hyperactivity disorder is related to glutamatergic dysfunction in the anterior cingulate cortex. World J Biol Psychiatry. Dec. 2016 15:1-9.
Beal MF, Kowall NW, Ellison DW, Mazurek MF, Swartz KJ, Martin JB. Replication of the neurochemical characteristics of Huntington's disease by quinolinic acid. Nature. 1986;321(6066):168-171.
Beckett, A. H., and N. J. Harper. "162. Configurational studies in synthetic analgesics: the synthesis of (-)-methadone from D-(-)-alanine." Journal of the Chemical Society (Resumed) (1957): 858-861.
Benedek IH, Blouin RA, McNamara PJ. Serum protein binding and the role of increased alpha1-acid glycoprotein in moderately obese male subjects. Br J Clin Pharmacol. 1984;18(6):941-946.
Berken, GH, Stone MM, Stone SK. Methadone in schizophrenic rage: a case study. Am J Psychiatry. Feb. 1978; 135(2):248-9.
Berman, EF, Adler MW. The anticonvulsant effect of opioids and opioid peptides against maximal electroshock seizures in rats. Neuropharmacology. Mar. 1984; 23(3):367-71.
Berman, R.M. et al., "Antidepressant Effects of Ketamine in Depressed Patients," Biol. Psych. 2000;47:351-354.

(56) References Cited

OTHER PUBLICATIONS

Bernstein G, Davis K, Mills C, Wang L, McDonnell M, Oldenhof J, et al. Characterization of the safety and pharmacokinetic profile of D-methadone, a novel N-methyl-D-aspartate receptor antagonist in healthy, opioid-naive subjects: results of two phase 1 studies. J Clin Psychopharmacol. 2019;39:226-37.
Bernstein, G. et al., Characterization of the Safety and Pharmacokinetic Profile of D-Methadone, a Novel N-Methyl-D-Aspartate Receptor Antagonist in Healthy, Opioid-Naive Subjects: Results of Two Phase 1 Studies J Clin Psychopharmacol. May-Jun. 2019;39(3):226-237.
Berretta N, Jones RS. Tonic facilitation of glutamate release by presynaptic N-methyl-D-aspartate autoreceptors in the entorhinal cortex. Neuroscience 1996; 75:339-344.
Bezprozvanny, I, Klockgether T. Therapeutic prospects for spinocerebellar ataxia type 2 and 3.Drugs Future. Dec. 2009; 34(12).
Biederman, J., Monuteaux, M. C., Mick, E., Spencer, T., Wilens, T. E., Silva, J. M., et al. (2006). Young adult outcome of attention deficit hyperactivity disorder: a controlled 10-year follow-up study. Psychological Medicine, 36(167-179).
Bikbova, G et al., Neuronal Changes in the Diabetic Cornea: Perspectives for Neuroprotection. Biomed Res Int. 2016; Article ID 5140823, 8 pgs.
Binder, DK, Scharfman HE. Brain-derived Neurotrophic Factor. Growth Factors. Sep. 2004; 22(3):123-31.
Bisaga, A. et al., "Therapeutic potential of NMDA receptor antagonists in the treatment of alcohol and substance use disorders," Exp Opin Invest Drugs 2009;9(10):2233-2248.
Blanke ML, VanDongen AM. Constitutive activation of the N-methyl-D-aspartate receptor via cleft-spanning disulfide bonds. J Biol Chem. 2008;283(31):21519-21529.
Blasco, H et al., The Glutamate Hypothesis in ALS: Pathophysiology and Drug Development. Curr Med Chem. 2014; 21(31):3551-75.
Blue, ME et al., Development of amino acid receptors in frontal cortex from girls with Rett syndrome. Annals of Neurology 1999; 45(4):541-5.
Blyumin, E. V. et al. "Construction of Three Contiguous Tertiary StereoCenters From Aziridines in One Step", Organic Letters, 2007, vol. 9(23), pp. 4677-4680. abstract; p. 4678, Scheme 1; p. 4679, Table 1, entry 1; p. 4680, col. 2, para 2.
Borzelleca, J. F. et al., "Toxicological Evaluation of μ-Agonists. Part II: 9-12, Assessment of Toxicity Following 30 Days of Repeated Oral Dosing of Male and Female Rats with Levo-alpha-noracetylmethadol HCI (NorLAAM)," Journal of Applied Toxicology (1995) 15(5):339-355.
Botez, MI, Botez-Marquard T, Elie R, Pedraza OL, Goyette K, Lalonde R.Amantadine hydrochloride treatment in heredodegenerative ataxias: a double blind study. J Neurol Neurosurg Psychiatry. Sep. 1996; 61(3):259-64.
Bouvier G, Bidoret C, Casado M, Paoletti P. Presynaptic NMDA receptors: Roles and rules. Neuroscience. 2015;311:322-340.
Boyer, P.A. et al., "Chronic Administration of Imipramine and Citalopram Alters the Expression of NMDA Receptor Subunit mRNAs in Mouse Brain: A Quantitative In Situ Hybridization Study," J Mol Neurosci 1998;10:219-233.
Bozic M, Valdivielso JM. The potential of targeting NMDA receptors outside the CNS. Expert Opin Ther Targets. 2015;19(3):399-413.
Brachman, RA, McGowan JC, Perusini JN, et al. Ketamine as a Prophylactic Against Stress-Induced Depressive-like Behavior. Biol Psychiatry. 2015;79(9):776-786.
Braidy N, Grant R, Adams S, Brew BJ, Guillemin GJ. Mechanism for quinolinic acid cytotoxicity in human astrocytes and neurons. Neurotox Res. 2009;16(1):77-86.
Brennan, BP, Roberts JL, Fogarty KV, Reynolds KA, Jonas JM, Hudson JI. Memantine in the treatment of binge eating disorder. an open-label, prospective trial. Int J Eat Disord. 2008 41(6):520-6.
Brizer, DA, Hartman N, Sweeney J, Millman RB. Effect of methadone plus neuroleptics on treatment-resistant chronic paranoid schizophrenia. Am J Psychiatry. Sep. 1985; 142(9):1106-7.
Broglio K. Randomization in Clinical Trials: Permuted Blocks and Stratification. JAMA. 2018;319(21):2223-2224.
Brown RT, Nicholas CR, Cozzi NV, Gassman MC, Cooper KM, Muller D, Thomas CD, Hetzel SJ, Henriquez KM, Ribaudo AS, Hutson PR. Pharmacokinetics of Escalating Doses of Oral Psilocybin in Healthy Adults. Clin Pharmacokinet. Dec. 2017;56(12):1543-1554.
Bruce, RD. The marketing of methadone: how an effective medication became unpopular. Int J Drug Policy. Nov. 2013; 24(6):e89-e90.
Brunoni, AR et al., Decreased brain-derived neurotrophic factor plasma levels in psoriasis patients. Braz J Med Biol Res. Aug. 2015; 48(8):711-4.
Cacabelos R, Takeda M, Winblad B. The glutamatergic system and neurodegeneration in dementia: preventive strategies in Alzheimer's disease. Int J Geriatr Psychiatry. Jan. 1999;14(1):3-47.
Cai, X, et al. The association between brain-derived neurotrophic factor gene polymorphism and migraine: a meta-analysis. J Headache Pain. 2017; 18(1):13.
Callahan RJ, Au JD, Paul M, Liu C, Yost CS. Functional inhibition by methadone of N-methyl-D-aspartate receptors expressed in Xenopus oocytes: stereospecific and subunit effects. Anesth Analg. 2004;98(3).
Canitano et al. ("Glutamatergic agents in Autism spectrum disorders: current trends", Research in Autism Spectrum Disorders, 2014, vol. 8, pp. 255-265), (Year: 2014).
Canitano et al. ("Glutannatergic agents in Autism spectrum disorders: current trends", Research in Autism Spectrum Disorders, 2014, vol. 8, pp. 255-265), (Year: 2014).
Capuron L, et al. Interferon-alpha-induced changes in tryptophan metabolism: relationship to depression and paroxetine treatment, Biol. Psychiatry. 2003, 54:906-914.
Carroll, FI and Carlezon WA. Development of Kappa Opioid Receptor Antagonists. Journal of medicinal chemistry. 2013; 56(6):2178-2195.
Casy, A. F., The steric factor in medicinal chemistry; dissymetric probes of pharmacological receptors (Opioid ligands part 2): pp. 503-548. 1993. Plenum Press.
Celiker, H et al., Neuroprotective Effects of Memantine in the Retina of Glaucomatous Rats: An Electron Microscopic Study. J Ophthalmic Vis Res. Apr.-Jun. 2016; 11(2):174-82.
Chen, Huei-Sheng Vincent and Lipton, Stuart A., The chemical biology of clinically tolerated NMDA receptor antagonists. Journal of Neurochemistry, 2006, 97, 1611-1626.
Chen, Huei-Sheng Vincent et al., The chemical biology of clinically tolerated NMDA receptor antagonists. Journal of Neurochemistry, 2006, 97, 1611-1626.
Cheng, A, Hou Y, Mattson MP. Mitochondria and neuroplasticity. ASN Neuro. Oct. 4, 2010;2(5).
Chisu, V et al., Testosterone induces neuroprotection from oxidative stress. Effects on catalase activity and 3-nitro-L-tyrosine incorporation into alpha-tubulin in a mouse neuroblastoma cell line. Arch Ital Biol. May 2006; 144(2):63-73.
Chou R, Cruciani RA, Fiellin DA, Compton P, Farrar JT, Haigney MC, Inturrisi C et al. Methadone safety: a clinical practice guideline from the American Pain Society and College on Problems of Drug Dependence, in collaboration with the Heart Rhythm Society. J Pain. 2014;15(4):321-337.
Cleveland WS. Robust locally weighted regression and smoothing scatterplots. J Am Stat Assoc. 1979;74(368):829-836.
Codd, E.E. et al., "Serotonin and Norepinephrine Uptake Inhibiting Activity of Centrally Acting Analgesics: Structural Determinants and Role in Antinociception," JPET 1995; 274(3):1263-1270.
Codd, EE, Shank RP, Schupsky JJ, Raffa RB. Serotonin and norepinephrine uptake inhibiting activity of centrally acting analgesics: structural determinants and role in antinociception. J Pharmacol Exp Ther. Sep. 1995;274(3):1263-70.
Colognesi et al., Depression and Cognitive Impairment—Extrahepatic Manifestations of NAFLD and NASH, Biomedicines 2020, 8, 229.

(56) References Cited

OTHER PUBLICATIONS

Compston, A, Coles A (Apr. 2002). "Multiple sclerosis". Lancet. 359 (9313):1221-31.
Corona, G et al., Testosterone supplementation and body composition: results from a meta-analysis of observational studies. J Endocrinol Invest. Sep. 2016; 39(9):967-81.
Coskunoglu, A. et al., Evidence of associations between brain-derived neurotrophic factor (BDNF) serum levels and gene polymorphisms with tinnitus. Noise Health. May-Jun. 2017; 19(88):140-148.
Cowan, A., Geller EB, Adler MW. Differential effects of opioids on flurothyl seizure thresholds in rats. NIDA Res Monogr 1979; 27:198-204.
Coyle, JT. NMDA Receptor and Schizophrenia: A Brief History. Schizophrenia Bulletin vol. 38 No. 5 pp. 920-926, 2012.
Dan, B. Angelman syndrome: Current understanding and research prospects. Epilepsia, 2009; 50:2331-2339.
Data from the NIMH Psychoactive Drug Screening Program (<http://pdsp.med.unc.edu>).
Davis, A.M. et al., "d-Methadone Blocks Morphine Tolerance and N-Methyl-D-Aspartate-Induced Hyperalgesia," J Pharma and Exper Therap, 1999;289:1048-1053.
Daws at al., Increased global integration in the brain after psilocybin therapy for depression. Nature Medicine, 2022.
Dayalu, P and Teener JW. Stiff Person Syndrome and Other Anti-GAD-Associated Neurologic Disorders. Semin Neurol. Nov. 2012; 32(5):544-9.
De Carvalho LP, Bochet P, Rossier J. The endogenous agonist quinolinic acid and the non endogenous homoquinolinic acid discriminate between NMDAR2 receptor subunit. Neurochem. Int. 1996; 28:445-452.
De Cid, R., Fonseca, F., Gratacs, M., Gutierrez, F., Martn-Santos, R., Estivill, X., & Torrens, M. (2008). BDNFvariability in opioid addicts and response to methadone treatment: preliminary findings. Genes, Brain and Behavior, 7(5), 515-522. doi:10.1111/j.1601-183x.2007.00386.x [Date of Publication: Sep. 8, 2008].
De Conno, F, Groff L, Brunelli C, Zecca E, Ventafridda V, Ripamonti Clinical experience with oral methadone administration in the treatment of pain in 196 advanced cancer patients C.J Clin Oncol. Oct. 1996; 14 (10):2836-42.
De Martin S, Vitolo O, Bernstein G, Alimonti A, Traversa S, Inturrisi CE, Manfredi PL, The NMDAR Antagonist Dextromethadone Increases Plasma BDNF Levels in Healthy Volunteers Undergoing a 14-Day In-Patient Phase 1 Study, ACNP 57th Annual Meeting: Poster Session II. Neuropsychopharmacol. 43, 228-382 (2018).
Delyfer, MN et al., Evidence for glutamate-mediated excitotoxic mechanisms during photoreceptor degeneration in the rd1 mouse retina. Mol Vis. Sep. 1, 2005; 11:688-96.
Den Boer, M et al., Hepatic steatosis: a mediator of the metabolic syndrome. Lessons from animal models. Arterioscler Thromb Vasc Biol. Apr. 2004; 24(4):644-9. Epub 2004.
Desseilles et al., Massachusetts General Hospital Safer Criteria for Clinical Trials and Research. Harvard Review of Psychiatry. Psychopharmacology, Sep.-Oct. 2013; 21(5):1-6.
Dickman KG, Youssef JG, Mathew SM, Said SI. Ionotropic glutamate receptors in lungs and airways: molecular basis for glutamate toxicity. Am J Respir Cell Mol Biol. 2004;30(2):139-144.
Djupesland PG, Mahmoud RA, Messina JC. Accessing the brain: the nose may know the way. J Cereb Blood Flow Metab. 2013;33(5):793-794.
Doble, The pharmacology and mechanism of action of riluzole. Neurology. Dec. 1996; 47(6 Suppl 4):S233-41.
Drago, F et al., Effects of opiates and opioids on intraocular pressure of rabbits and humans. 1985 Clin Exp Pharmacol Physiol. Mar.-Apr. 1985; 12(2):107-13.
Drug Enforcement Administration. Diversion Control Division. Drug & Chemical Evaluation Section. Methadone. Jul. 19, 2019.
Japanese Office Action in Japanese Patent Application No. 2023-562287, dated Oct. 14, 2025, 4 pgs. (English translation available).
Japanese Office Action issued in Japanese Application No. 2023-562287, dated Feb. 24, 2026, 4 pgs. (English translation available).
Organic Letters, 2007, vol. 9, No. 23, p. 4577-4680, DOI: 10.1021/ol7015302.
Olivan-Blázquez, B, Herrera-Mercadal P, Puebla-Guedea M, Pérez-Yus MC, Andrés E, Fayed N, López-Del-Hoyo Y, Magallon R, Roca M, Garcia-Campayo J. Efficacy of memantine in the treatment of fibromyalgia: A double-blind, randomised, controlled trial with 6-month follow-up. Pain. Dec. 2014; 155(12):2517-25.
Olney JW, Labruyere J, Price MT (1989) "Pathological Changes Induced in Cerebrocortical Neurons by Phencyclidine and Related Drugs". Science. 244:1360-1362.
Olsen, G.D., Wendel, H.A., Livermore, J.D., Leger, R.M., Lynn, R.K. and Gerber, N., Clinical effects and pharmacokinetics of racemic methadone and its optical isomers, Clin. Pharmacol. Ther., 21 (1976) 147-157.
Ondo, W. G., "Methadone for Refractory Restless Legs Syndrome,." Movement Disorders: Official Journal of the Movement Disorder Society (Mar. 2005) 20(3):345-348.
Ortiz-López, L, González-Olvera JJ, Vega-Rivera NM, García-Anaya M, Carapia-Hernández AK, Velázquez-Escobar JC, Ramírez-Rodríguez GB. Human neural stem/progenitor cells derived from the olfactory epithelium express the TrkB receptor and migrate in response to BDNF. Neuroscience. Jul. 4, 2017; 355:84-100.
Paoletti, P. et al., NMDA receptor subunit diversity: impact on receptor properties, synaptic plasticity and disease. Nature Reviews Neuroscience 14, 383-400 (2013).
Papakostas GI, Fava M. Predictors, moderators, and mediators (correlates) of treatment outcome in major depressive disorder. Dialogues Clin Neurosci. 2008;10(4):439-451.
Partial International Search Report in International Patent Application No. PCT/US2018/016159, mailed May 7, 2018, 2 pgs.
Pasternak GW, Pan YX. Mu opioids and their receptors: evolution of a concept. Pharmacol Rev. 2013;65(4):1257-1317. Published Sep. 27, 2013.
Patel, AV et al., Lingual and palatal gustatory afferents each depend on both BDNF and NT-4, but the dependence is greater for lingual than palatal afferents. J Comp Neurol. Aug. 15, 2010; 518(16):3290-301.
Patrizi, A et al., Chronic Administration of the N-Methyl-D-Aspartate Receptor Antagonist Ketamine Improves Rett Syndrome Phenotype. Biol Psychiatry. May 1, 2016; 79(9):755-64.
Patrizi, A, Picard N, Simon AJ, Gunner G, Centofante E, Andrews NA, Fagiolini M. Chronic Administration of the N-Methyl-D-Aspartate Receptor Antagonist Ketamine Improves Rett Syndrome Phenotype. Biol Psychiatry. May 1, 2016;79(9):755-64.
Peeters M, Romieu P, Maurice T, Su TP, Maloteaux JM, Hermans E. Involvement of the sigma1 receptor in the modulation of dopaminergic transmission by amantadine, The European Journal of Neuroscience 2004. 19(8):2212-20.
Pellissier, LP et al., m opioid receptor, social behaviour and autism spectrum disorder: reward matters. Br J Pharmacol. Apr. 3, 2017 doi: 10.1111/bph. 13808. [Epub ahead of print].
Pereverseff RS, Beshai S, Dimova M. First episode indices associated with lifetime chronicity of depression among formerly depressed participants: an exploratory study [published online ahead of print, May 10, 2017] [published correction appears in J Ment Health. Dec. 2018;27(6):604]. J Ment Health. 2017;1-7.
Peter, S, Manousaridis K, Boesch S, Mennel S. Memantine for optic nerve atrophy in Friedreich's Ataxia. Article in German. Ophthalmologe. Aug. 2016; 113(8):704-7.
Peyman, GA et al. Effects of morphine on corneal sensitivity and epithelial wound healing: implications for topical ophthalmic analgesia. Br J Ophthalmol. Feb. 1994; 78(2):138-141.
Pfister et al. NASH limits anti-tumour surveillance in immunotherapy-treated HCC. Nature 2021; 592: 450-456.
Pietersen, HG et al., Glutamate metabolism of the heart during coronary artery bypass grafting. Clin Nutr. Apr. 1998; 17(2):73-5.
Pochwat B, Palucha-Poniewiera A, Szewczyk B, Pilc A, Nowak G. NMDA antagonists under investigation for the treatment of major depressive disorder. Expert Opin Investig Drugs. 2014.
Pontius, A. A., Overwhelming Remembrance of Things Past: Proust Portrays Limbic Kindling by External Stimulus-Literary Genius

(56) References Cited

OTHER PUBLICATIONS

Can Presage Neurobiological Patterns of Puzzling Behavior. Psychological Reports, 73(2), 1993, pp. 615-621.
Povysheva NV, Johnson JW. Tonic NMDA receptor-mediated current in prefrontal cortical pyramidal cells and fast-spiking interneurons. J Neurophysiol. 2012;107(8):2232-2243.
Prentice, H, Modi JP, Wu JY. Mechanisms of Neuronal Protection against Excitotoxicity, Endoplasmic Reticulum Stress, and Mitochondrial Dysfunction in Stroke and Neurodegenerative Diseases. Oxid Med Cell Longev. 2015.
Prokopova, B, Hlavacova N, Vlcek M, Penesova A, Grunnerova L, Garafova A, Turcani P, Kollar B, Jezova D. Early cognitive impairment along with decreased stress-induced BDNF in male and female patients with newly diagnosed multiple sclerosis. J Neuroimmunol. Jan. 15, 2017; 302:34-40.
PubChem. CID 10072. Mar. 26, 2005, pp. 1-19. Retrieved from the Internet <URL: <https://pubchem.ncbi.nlm.nih.gov/compound/10072>>; p. 2, formula.
PubChem. CID 426183. Mar. 26, 2005, pp. 1-9. Retrieved from the Internet <URL: https://pubchem.ncbl.nlm.nih.gov/compound/426183>>; p. 2, formula.
PubChem. CID 44795. Aug. 8, 2005, pp. 1-10. Retrieved from the Internet <URL: <https://pubchem.ncbi.nlm.nih.gov/compound/44795>>; p. 2, formula.
PubChem. CID 62408. Aug. 8, 2005, pp. 1-10. Retrieved from the Internet <URL: https://pubchem.ncanlm.nlh.gov/compound/62408>; p. 2, formula.
PubChem. CID 643985. Jun. 1, 2005, pp. 1-22. Retrieved from the Internet <URL: <https://pubchem.ncbi.nim.nih.gov/compound/643985>>; p. 2, formula.
PubChem. CID 9648. Mar. 26, 2005, pp. 1-21. Retrieved from the Internet <URL: <https://pubchem.ncbi.nlm.nih.gov/compound/9648>>; p. 2, formula.
Ragguett RM, Rong C, Rosenblat JD, Ho RC, McIntyre RS. Pharmacodynamic and pharmacokinetic evaluation of buprenorphine + samidorphan for the treatment of major depressive disorder. Expert Opin Drug Metab Toxicol. 2018, 14(4):475-482.
Raison CL, et al. CSF concentrations of brain tryptophan and kynurenines during immune stimulation with IFN-alpha: relationship to CNS immune responses and depression, Mol. Psychiatry. 2010, 15:393-403.
Ramírez LA, Pérez-Padilla EA, García-Oscos F, Salgado H, Atzori M, Pineda JC. A new theory of depression based on the serotonin/kynurenine relationship and the hypothalamic-pituitary-adrenal axis, Biomedica. 2018;38(3):437-450. Published Sep. 1, 2018.
Rasika, S et al., BDNF Mediates the Effects of Testosterone on the Survival of New Neurons in an Adult Brain. Proc Natl Acad Sci U S A. Aug. 16, 1994; 91(17):7854-8.
Reddy, DS. Anticonvulsant activity of the testosterone-derived neurosteroid 3alpha-androstanediol. Neuroreport. Mar. 1, 2004; 15(3):515-8.
Ribeiro, S, Schmidt AP, Schmidt SR. Opioids for treating nonmalignant chronic pain: the role of methadone. Rev Bras Anestesiol. Sep. 2002; 52(5):644-51.
Rickli A, Liakoni E, Hoener MC, Liechti ME. Opioid-induced inhibition of the human 5-HT and noradrenaline transporters in vitro: link to clinical reports of serotonin syndrome. Br J Pharmacol. 2018;175(3):532-543.
Riva, V, Battaglia M, Nobile M, Cattaneo F, Lazazzera C, Mascheretti S, Giorda R, Mérette C, Émond C, Maziade M, Marino C. GRIN2B predicts attention problems among disadvantaged children.Eur Child Adolesc Psychiatry. Jul. 2015; 24(7):827-36.
Roberts, A. C. et al. Downregulation of NR3A-containing NMDARs is required for synapse maturation and memory consolidation. Neuron 63, 342-356 (2009).
Rodríguez-Muñoz M, Sánchez-Blázquez P, Vicente-Sánchez A, Berrocoso E, Garzón J. The mu-opioid receptor and the NMDA receptor associate in PAG neurons: implications in pain control. Neuropsychopharmacology. 2012;37(2):338-349.
Roffey, P, Mikhail M, Thangathurai D. NMDA receptor blockade prevents nitroglycerin-induced headaches. Headache. Jul.-Aug. 2001; 41(7):733.
Rojas-Corrales, MO, Gibert-Rahola J, Mico JA. Role of atypical opiates in OCD. Experimental approach through the study of 5-HT2A/C receptor-mediated behavior. Psychopharmacology (Berl). Feb. 2007; 190(2):221-31.
Rosanoff, A. Magnesium and hypertension. Clin Calcium. Feb. 2005; 15(2):255-60.
Rosini, F, Federighi P, Pretegiani E, Piu P, Leigh RJ, Serra A, Federico A, Rufa A. Ocular-motor profile and effects of memantine in a familial form of adult cerebellar ataxia with slow saccades and square wave saccadic intrusions. PLOS One. Jul. 22, 2013; 8(7).
Rottach, KG, Schaner BM, Kirch MH, Zivotofsky AZ, Teufel LM, Gallwitz T, Messer T. Restless legs syndrome as side effect of second generation antidepressants. J Psychiatr Res. 2009 43(1):70-5.
Rush AJ, Trivedi MH, Wisniewski SR, Nierenberg AA, Stewart JW, Warden D, et al. Acute and longer-term outcomes in depressed outpatients requiring one or several treatment steps: a Star*D report. Am J Psychiatry. 2006;163:1905-17.
Saint-Mont U. Randomization Does Not Help Much, Comparability Does. PLoS One. 2015;10(7):e0132102. Published Jul. 20, 2015.
Sala, G. Antioxidants Partially Restore Glutamate Transport Defect in Leber Hereditary Optic Neuropathy Cybrids. Journal of Neuroscience Research 2008, 86:3331-3337.
Sanacora, G et al., Ketamine: Promising Path or False Prophecy in the Development of Novel Therapeutics for Mood Disorders?, Neuropsychopharmacology (2015) 40, 259-267.
Sanacora, G. et al., "Subtype-Specific Alterations of y-Aminobutyric Acid and Glutamate in Patients with Major Depression," Arch Gen Psychiatry 2004;61:705-713.

* cited by examiner (S)-2-aminopropanoic acid

1

2

3

1,1,2-trimethylaziridin-1-ium intermediate

4

(S)-methadone*HCl

Methadone-nitrile

Isomethadone-nitrile

* = chiral center (*R*)-, (*S*)-, or rac- configuration or (*R*)-, (*S*)- or rac-methadone*HCl

* = chiral center (*R*)-, (*S*)-, or rac- configuration. Configuration is retained during the synthesis
PG = protecting group 1.1 1.2

1.2 1.3

1.3 1

* = chiral center (*R*)-, (*S*)-, or rac- configuration. Configuration is retained during the synthesis
PG = protecting group 1.1 1.2

1.2 2.1

2.1 2

* = chiral center (R)-, (S)-, or rac- configuration. Configuration is retained during the synthesis
PG = protecting group (I)

(*S*)-1.1

(*S*)-1.2'

(*S*)-1'

(*R*)-1.1

(*R*)-2.2''

(*R*)-2''

(S)-1' + 3 → (S)-4' → (S)-5

| Name | Retention time (min) | % Area | USP Resolution |
|---|---|---|---|
| (*R*)-Methadone nitrile ((*R*)-5) | 6.65 | 49.37 | 2.77 |
| (S)-Methadone nitrile ((S)-5) | 7.98 | 50.63 | |

| Name | Retention time (min) | % Area | USP Resolution |
|---|---|---|---|
| (*R*)-Methadone nitrile ((*R*)-5) | - | - | - |
| (S)-Methadone nitrile ((S)-5) | 7.93 | 100 | |

(R)-2''

3

(R)-4''

(R)-5

| Name | Retention time (min) | % Area | USP Resolution |
|---|---|---|---|
| (*R*)-Methadone nitrile ((*R*)-5) | 6.65 | 49.37 | 2.77 |
| (S)-Methadone nitrile ((S)-5) | 7.98 | 50.63 | |

| Name | Retention time (min) | % Area | USP Resolution |
|---|---|---|---|
| (*R*)-Methadone nitrile ((*R*)-5) | 6.62 | 100 | - |
| (S)-Methadone nitrile ((S)-5) | - | - | |

(S)-5

(S)-methadone*HCl

| Name | Retention time (min) | % Area | USP Resolution |
|---|---|---|---|
| (*R*)-Methadone | 7.88 | 50.26 | 1.4 |
| (S)-Methadone | 8.85 | 49.74 | |

| Name | Retention time (min) | % Area | USP Resolution |
|---|---|---|---|
| (*R*)-Methadone | - | - | - |
| (*S*)-Methadone | 8.79 | 100 | |

***(R)*-5**

***(R)*-methadone*HCl**

| Name | Retention time (min) | % Area | USP Resolution |
|---|---|---|---|
| (*R*)-Methadone | 7.88 | 50.26 | 1.4 |
| (*S*)-Methadone | 8.85 | 49.74 | |

| Name | Retention time (min) | % Area | USP Resolution |
|---|---|---|---|
| (*R*)-Methadone | 7.92 | 100 | - |
| (*S*)-Methadone | - | - | |

METHODS FOR SYNTHESIZING ENANTIOPURE (S)-METHADONE, (R)-METHADONE, RACEMIC (R,S)-METHADONE AND RELATED ANALOGUE SUBSTANCES

CROSS-REFERENCE TO RELATED APPLICATION

This application claims priority to, and the benefit of the filing date of, U.S. Patent Application Ser. No. 63/172,901, filed on Apr. 9, 2021, the disclosure of which is incorporated by reference herein in its entirety.

FIELD OF THE INVENTION

The present invention relates generally to methods for the synthesis of enantiopure (S)-methadone, (R)-methadone, (R,S)-methadone, and related analogues.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

As initially discovered by the applicants, (S)-methadone, the dextrorotatory isomer of methadone (which may also be referred to herein as dextromethadone, esmethadone, and/or REL-1017) is an uncompetitive, low-affinity, low-potency N-methyl-D-aspartate (NMDA) receptor antagonist displaying a preference for pathologically and tonically open, hyperactive ion channels, thus prompting potential effectiveness for a multiplicity of diseases and disorders at well tolerated dosages, without psychotomimetic effects (Gorman A L, Elliott K J, Inturrisi C E. *The d- and l-isomers of methadone bind to the non-competitive site on the N-methyl-D-aspartate (NMDA) receptor in ratforebrain and spinal cord.* Neurosci Lett. 1997 Feb. 14; 223(1):5-8. doi: 10.1016/s0304-3940(97)13391-2. PMID: 9058409; Bernstein G, Davis K, Mills C, Wang L, McDonnell M, Oldenhof J, Inturrisi C, Manfredi P L, Vitolo O V. *Characterization of the Safety and Pharmacokinetic Profile of D-Methadone, a Novel N-Methyl-D-Aspartate Receptor Antagonist in Healthy, Opioid-Naive Subjects: Results of Two Phase* 1 *Studies.* J Clin Psychopharmacol. 2019 May/June; 39(3): 226-237. doi: 10.1097/JCP.0000000000001035. PMID: 30939592; Fava M, Stahl S, Pani L, De Martin S, Pappagallo M, Guidetti C, Alimonti A, Bettini E, Mangano R M, Wessel T, de Somer M, Caron J, Vitolo O V, DiGuglielmo G R, Gilbert A, Mehta H, Kearney M, Mattarei A, Gentilucci M, Folli F, Traversa S, Inturrisi C E, Manfredi P L. REL-1017 (*Esmethadone*) *as Adjunctive Treatment in Patients With Major Depressive Disorder: A Phase* 2a *Randomized Double-Blind Trial.* Am J Psychiatry. 2022 February; 179 (2):122-131. doi: 10.1176/appi.ajp.2021.21020197. Epub 2021 Dec. 22. PMID: 34933568). Esmethadone exhibits a 20-fold lower affinity for the opioid receptors compared to the enantiomeric (R)-methadone (Codd E E, Shank R P, Schupsky J J, Raffa R B. *Serotonin and norepinephrine uptake inhibiting activity of centrally acting analgesics: structural determinants and role in antinociception.* J Pharmacol Exp Ther. 1995 September; 274(3):1263-70. PMID: 7562497), and does not display meaningful opioid agonist effects, including addiction liability.

Racemic methadone is used for the treatment of opioid use disorder (OUD) and for the treatment of pain. Based on clinical and experimental evidence, half dose of (R)-methadone instead of (R,S)-methadone can be administered to patients (Gutwinski S, Schoofs N, Stuke H, Riemer T G, Wiers C E, Bermpohl F. *Opioid tolerance in methadone maintenance treatment: comparison of methadone and levomethadone in long-term treatment.* Harm Reduct J. 2016 Feb. 16; 13:7. doi: 10.1186/s12954-016-0095-0. PMID: 26879120; PMCID: PMC4754801; Soyka M, Zingg C. *Feasability and safety of transfer from racemic methadone to* (*R*)-*methadone in primary care: clinical results from an open study.* World J Biol Psychiatry. 2009; 10(3):217-24. doi: 10.1080/15622970802416057. PMID: 19629858). The administration of the (R)-form would decrease plasma concentrations of methadone by two-fold, thereby producing a safer safety profile, while not affecting the activity on the mu opioid receptors. Prescription of (R)-methadone would also diminish the clinical concern of CYP2B6 slow metabolizer status for cardiotoxic effects. At the doses used to treat OUD and pain, (R)-methadone may therefore confer a lower risk of QTc interval prolongation (time from the start of the Q wave to the end of the T wave, time taken for ventricular depolarisation and repolarization) resulting in a better safety profile compared to (R,S)-methadone (Grilo L S, Carrupt P A, Abriel H. *Stereoselective Inhibition of the hERGI Potassium Channel.* Front Pharmacol. 2010 Nov. 22; 1:137. doi: 10.3389/fphar.2010.00137. PMID: 21833176; PMCID: PMC3153011).

The emerging importance of the two methadone isomers and the benefits of their administration as separate drugs (rather than the administration of racemic methadone), underscores the importance of developing cost-effective procedures for the synthesis of methadone isomers with high optical purity.

Beckett et al. reported the first protocol for a stereoselective synthesis of (R)-methadone starting from (R)-alanine in 1957 [Beckett, A. H., and N. J. Harper. "162. *Configurational studies in synthetic analgesics: the synthesis of* (−)-*methadone from D*-(−)-*alanine*." Journal of the Chemical Society (Resumed) (1957): 858-861]. This protocol included a seven step procedure resulting in roughly 5% overall yield with an optical purity of approximately 72% for the final levomethadone. Such a procedure, in principle, could be utilized for the preparation of both (R)-, and (S)-methadone. However, the complex synthetic route, low optical purity, and poor overall yield are not practical and discourage its use, especially for exploitation in the pharmaceutical industry.

In 2000, U.S. Pat. No. 6,143,933 by Scheinmann et al. provided a method involving the enzymatic resolution of the racemic intermediate 1-(dimethylamino)propan-2-ol followed by conversion of the enantiomers to optically active (R)- and (S)-methadone with about 3% overall yield and enantiomeric excess greater than 99%. Despite the excellent enantiomeric excess achieved, the overall yield for this process is prohibitively low and the involvement of an enzymatic reaction is not practical and contemplates a high-cost incurrence for industrial-scale processes. Additionally, methods based on the racemic synthesis of methadone followed by resolution of enantiomers (including those disclosed in U.S. Publication No. US2014/0350302) suffer from the introduction of undesirable impurities, complex operations, and significant reduction in the overall yield of the desired enantiomer, resulting in strategies for large scale manufacturing that are not appealing.

U.S. Publication No. 2017/0057909 by Mkrtchyan et al. represented an advance in the state of the art for the chiral synthesis of either (R)- or (S)-methadone providing more efficient methods for the synthesis of optically active methadones starting from (R)- or (S)-alanine respectively with about 20% overall yield and enantiomeric excess greater than 99%. The best performing enantioselective procedure provided by Mkrtchyan et al. for the synthesis of optically pure methadones consists of converting (R)- or (S)-alanine to the corresponding enantiopure N,N-dimethyl-alanine; reduction of the N,N-dimethyl-alanine to form N,N-dimethyl-alaninol; converting the N,N-dimethyl-alaninol to the corresponding chloride intermediate via a substitution reaction; mixing the chloride intermediate and a base, to form 1,1,2-trimethylaziridin-1-ium in situ, then treatment with 2,2-diphenylacetonitrile to provide enantiopure methadone-nitrile; and finally exposing the methadone-nitrile to ethyl magnesium bromide to form an ethyl imine intermediate, which is subsequently hydrolyzed in the presence of hydrochloric acid to provide optically pure methadone hydrochloride (See FIG. 1, which depicts this synthesis strategy with respect to (S)-methadone).

When one looks to the best results among the two enantiomers in the examples provided in Mkrtchyan's US 2017/0057909 using this synthetic strategy, the reagents and conditions chosen (and resulting yields) are: i) $CH_2O$, Pd/C, $H_2$, water, 50° C. for 20 h, then reflux for 1 h, (85% yield); ii) $LiAlH_4$, THF, 0° C. to reflux, 16 h, (68% yield); iii) $SOCl_2$, $CHCl_3$, 0° C. to reflux, 1 h, (93% yield); iv) KOtBu, $Ph_2CHCN$, DMF, rt for 2.5 h and then 45° C. for 15 h, (38% yield); v) EtMgBr, toluene, 110° C. for 3 h, then 6M HCl, 75° C. for 3 h, (88% yield). Overall yield: 18%

All the synthetic procedures disclosed in the literature (for example WO2013/168000, WO2017/35224, WO2013/77720, and US2015/152081) are based on one key step shown at step "iv" in FIG. 1, namely the attack of 2,2-diphenylacetonitrile anion on the 1,1,2-trimethylaziridin-1-ium generated by an intramolecular $S_N2$-reaction of (generally) 1-dimethylamino-2-chloropropane under basic conditions. The diphenylacetonitrile anion can then attack from two sides of the aziridinium salt resulting in competitive ring-opening reactions with low levels of regiochemical discrimination. In case of an attack at the least substituted C-atom of the aziridinium salt, the desired methadone-nitrile is formed. However, if the attack occurs at the higher order C-atom, the by-product isomethadone-nitrile is formed (See FIG. 2). Under the optimal mixture of base, solvent, and reaction conditions, the outcome of this reaction is at best a 1:3 (isomethadone-nitrile:methadone-nitrile) mixture of the two regioisomeric products. The resulting mixture is then purified by adopting a complex crystallization process that exploit the higher solubility isomethadone-nitrile, leading to non-efficient recovery and low purified yield of the desired methadone-nitrile.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

As described above, the emerging importance of the two methadone isomers, and the benefits of their administration as separate drugs, underscores the importance of developing cost-effective procedures for the synthesis of methadone isomers with high optical purity. And so, one aspect of the present invention is directed to novel enantioselective approaches for the synthesis of (S)-methadone, (R)-methadone, (R,S)-methadone and their analogues. In particular, one aspect includes a method for preparing (S)-methadone, (R)-methadone or (R,S)-methadone from optically pure ((S)- or (R)-) or racemic N-protected 4-methyl-cyclic sulfamidate or N-protected 2-methylaziridine. In certain embodiments, the process includes a ring opening reaction of optically pure ((S)- or (R)-) or racemic N-protected 4-methyl-cyclic sulfamidate or N-protected 2-methylaziridine with 2,2-diphenylacetonitrile in the presence of a base to provide ((S)- or (R)-) or racemic N-protected-dinormethadone nitrile with retention of configuration. This ring opening reaction is then followed by a two-step/one-pot deprotection/reductive amination of the N-protected-dinormethadone nitrile to provide (R)-, (S)-, or (R,S)-methadone nitrile. A reaction of the (R)-, (S)-, or (R,S)-methadone nitrile with an organomagnesium halide reagent to form an ethyl-imine intermediate is then performed—followed by imine hydrolysis to provide (R)-, (S)-, or (R,S)-methadone.

Another aspect of the present invention is directed to a method for preparing (S)-methadone hydrochloride, (R)-methadone hydrochloride or (R,S)-methadone hydrochloride from optically pure ((S)- or (R)-) or racemic N-protected 4-methyl-cyclic sulfamidate or N-protected 2-methylaziridine. In certain embodiments, the process includes a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration. This ring opening reaction is then followed by a two-step/one-pot deprotection/reductive amination of the N-protected-dinormethadone nitrile to provide (R)-, (S)-, or (R,S)-methadone nitrile. A reaction of the (R)-, (S)-, or (R,S)-methadone nitrile with an organomagnesium halide reagent to form an ethyl-imine intermediate is then performed—followed by hydrochloric acid-mediated imine hydrolysis to provide (R)-, (S)-, or (R,S)-methadone hydrochloride.

Another aspect of the present invention is directed to a compound (or pharmaceutically acceptable salt thereof, prepared by the method of the two aspects described above. In various embodiments, the compound (or pharmaceutically acceptable salt thereof) has the formula:

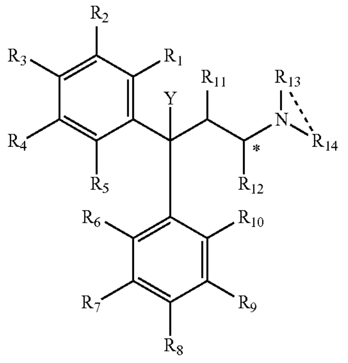

wherein (1) $R_1$ to $R_{10}$ are, independently for each occurrence, hydrogen, deuterium, halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (2) $R_1$ and $R_{12}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or $R_1$ and $R_{12}$ are, independently for each occurrence, selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (3) $NR_{13}R_{14}$ is optionally cyclized through $C_3$-$C_{12}$ cycloalkyl, or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (4) if $NR_{13}R_{14}$ is not cyclized $R_{13}$ and $R_{14}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, or $R_{13}$ and $R_{14}$ are, independently for each occurrence, selected from the group consisting of alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (5) Y is cyano, —C(O)$R_{15}$, —C(OH)$R_{15}$, —C($OR_{16}$)$R_{15}$. $R_{15}$ and $R_{16}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or $R_{15}$ and $R_{16}$ are, independently for each occurrence, selected from the group consisting of alkyl ester, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; and (6) * is a stereocenter selected from (R)-, (S)- or (R,S)-configuration, wherein the stereocenter is in an R configuration, and wherein the compound is present in greater than 90%, 95%, 97%, 99%, 99.5%, or 99.9% enantiomeric excess (e.e) compared to the S isomer, or wherein the stereocenter is in an S configuration, and wherein the compound is present in greater than 90%, 95%, 97%, 99%, 99.5%, or 99.9% enantiomeric excess (e.e.) compared to the R isomer.

A further aspect of the present invention is directed to a method for the chromatography free and scalable preparation of a cyclic sulfamidate starting material selected from benzyl (S)-4-methyl-1,2,3-oxathiazolidine-3-carboxylate 2,2-dioxide, (R)-4-methyl-1,2,3-oxathiazolidine-3-carboxylate 2,2-dioxide, and (R,S)-4-methyl-1,2,3-oxathiazolidine-3-carboxylate 2,2-dioxide.

A further aspect of the present invention is directed to a method for preparing (R)-, (S)-, or (R,S)-methadone nitrile. In this aspect, the method includes a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration. And this step is then followed by a two-step/one-pot deprotection/reductive amination of the N-protected-dinormethadone nitrile to provide (R)-, (S)-, or (R,S)-methadone nitrile.

Another aspect of the present invention is directed to a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE INVENTION

Figure 1:
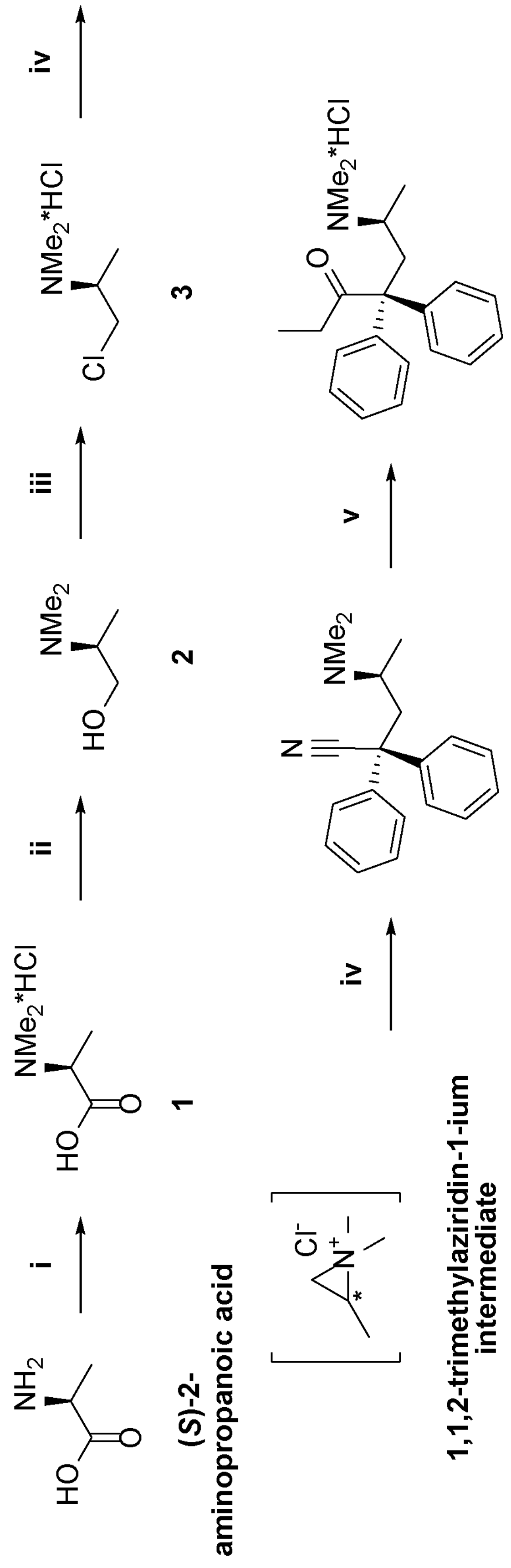
FIG. 1 is a schematic showing the synthesis of (S)-methadone using the strategy proposed in U.S. Publication No. 2017/0057909.
Figure 2:
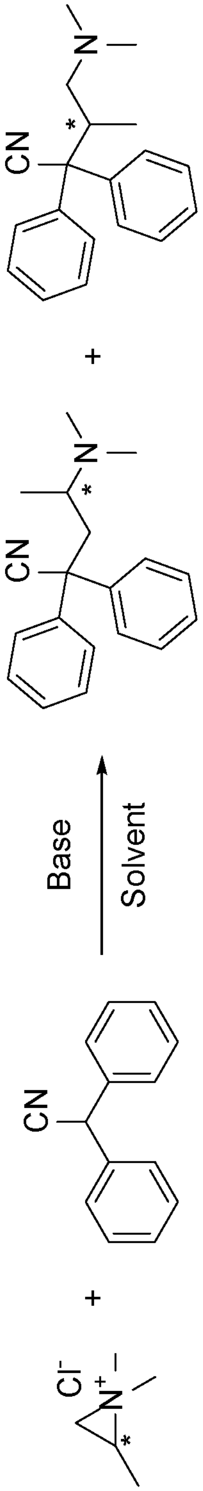
FIG. 2 is a schematic showing a key step in previously reported procedures for the synthesis of (R)-, (S)- and (R,S)-methadone.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described above, one aspect of the present invention is directed to a method for preparing (S)-methadone, (R)-methadone or (R,S)-methadone from optically pure ((S)- or (R)-) or racemic N-protected 4-methyl-cyclic sulfamidate or N-protected 2-methylaziridine. In certain embodiments, the process includes a ring opening reaction of optically pure ((S)- or (R)-) or racemic N-protected 4-methyl-cyclic sulfamidate or N-protected 2-methylaziridine with 2,2-diphenylacetonitrile in the presence of a base to provide ((S)- or (R)-) or racemic N-protected-dinormethadone nitrile with retention of configuration. This ring opening reaction is then followed by a two-step/one-pot deprotection/reductive amination of the N-protected-dinormethadone nitrile to provide (R)-, (S)-, or (R,S)-methadone nitrile. A reaction of the (R)-, (S)-, or (R,S)-methadone nitrile with an organomagnesium halide reagent to form an ethyl-imine intermediate is then performed—followed by imine hydrolysis to provide (R)-, (S)-, or (R,S)-methadone.

Another aspect of the present invention is directed to a method for preparing (S)-methadone hydrochloride, (R)-methadone hydrochloride or (R,S)-methadone hydrochloride from optically pure ((S)- or (R)-) or racemic N-protected 4-methyl-cyclic sulfamidate or N-protected 2-methylaziridine. In certain embodiments, the process includes a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration. This ring opening reaction is then followed by a two-step/one-pot deprotection/reductive amination of the N-protected-dinormethadone nitrile to provide (R)-, (S)-, or (R,S)-methadone nitrile. A reaction of the (R)-, (S)-, or (R,S)-methadone nitrile with an organomagnesium halide reagent to form an ethyl-imine intermediate is then performed—followed by hydrochloric acid-mediated imine hydrolysis to provide (R)-, (S)-, or (R,S)-methadone hydrochloride.

Another aspect of the present invention is directed to a compound (or pharmaceutically acceptable salt thereof, prepared by the method of the two aspects described above. In various embodiments, the compound (or pharmaceutically acceptable salt thereof) has the formula:

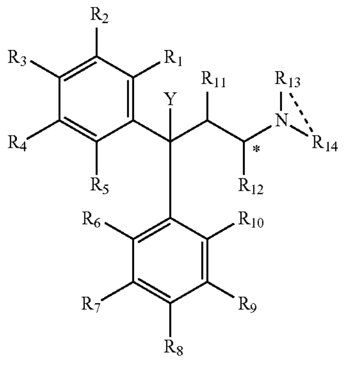

wherein (1) $R_1$ to $R_{10}$ are, independently for each occurrence, hydrogen, deuterium, halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (2) $R_{11}$ and $R_{12}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or Ru and $R_{12}$ are, independently for each occurrence, selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (3) $NR_{13}R_{14}$ is optionally cyclized through $C_3$-$C_{12}$ cycloalkyl, or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (4) if $NR_{13}R_{14}$ is not cyclized $R_{13}$ and $R_{14}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, or $R_{13}$ and $R_{14}$ are, independently for each occurrence, selected from the group consisting of alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (5) Y is cyano, —C(O)$R_{15}$, —C(OH)$R_{15}$, —C($OR_{16}$)$R_{15}$. $R_{15}$ and $R_{16}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or $R_{15}$ and $R_{16}$ are, independently for each occurrence, selected from the group consisting of alkyl ester, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; and (6) * is a stereocenter selected from (R)-, (S)- or (R,S)-configuration, wherein the stereocenter is in an R configuration, and wherein the compound is present in greater than 90%, 95%, 97%, 99%, 99.5%, or 99.9% enantiomeric excess (e.e) compared to the S isomer, or wherein the stereocenter is in an S configuration, and wherein the compound is present in greater than 90%, 95%, 97%, 99%, 99.5%, or 99.9% enantiomeric excess (e.e) compared to the R isomer.

A further aspect of the present invention is directed to a method for the chromatography free and scalable preparation of a cyclic sulfamidate starting material selected from benzyl (S)-4-methyl-1,2,3-oxathiazolidine-3-carboxylate 2,2-dioxide, (R)-4-methyl-1,2,3-oxathiazolidine-3-carboxylate 2,2-dioxide, and (R,S)-4-methyl-1,2,3-oxathiazolidine-3-carboxylate 2,2-dioxide.

Yet a further aspect of the present invention is directed to a method for preparing (R)-, (S)-, or (R,S)-methadone nitrile. In this aspect, the method includes a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration. And this step is then followed by a two-step/one-pot deprotection/reductive amination of the N-protected-dinormethadone nitrile to provide (R)-, (S)-, or (R,S)-methadone nitrile.

And another aspect of the present invention is directed to a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration.

Figure 3:
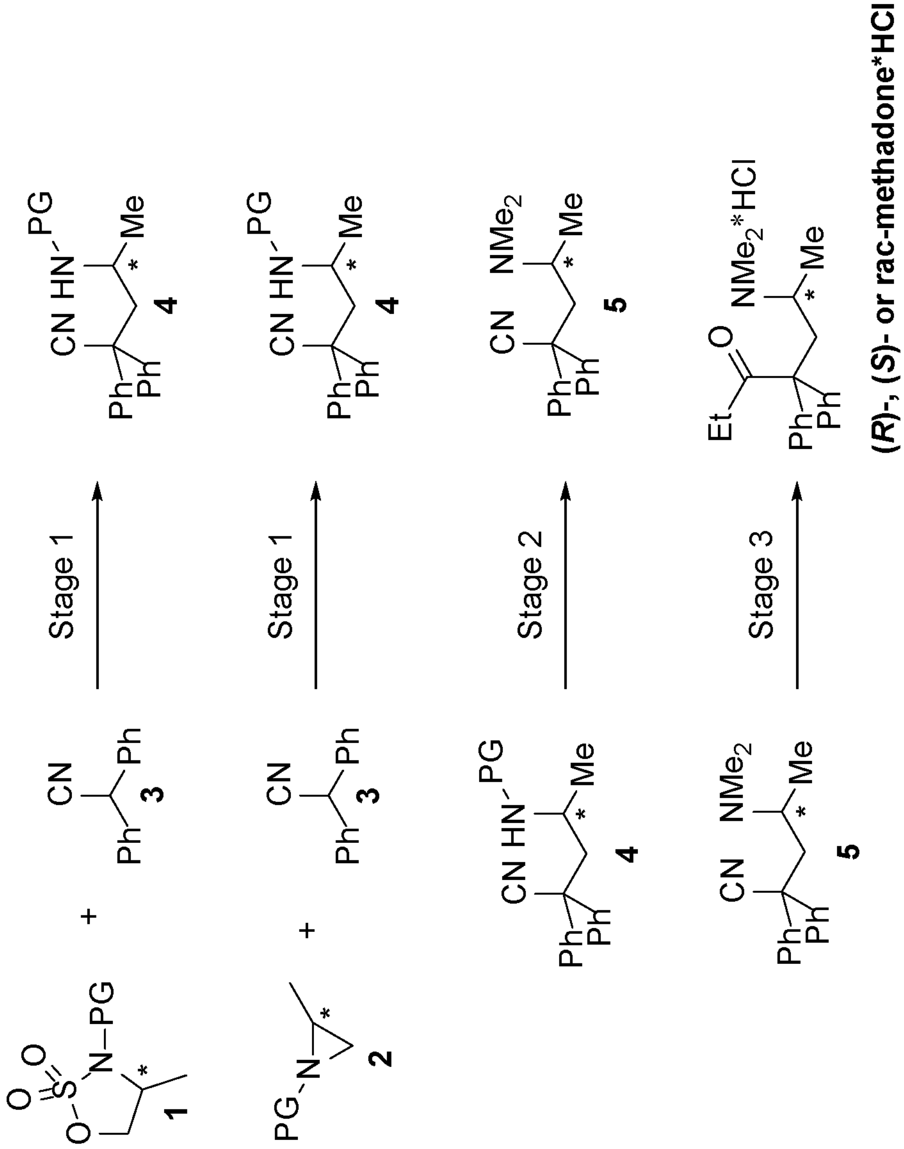
FIG. 3 is a schematic representation of a procedure for preparation of (R)-, (S)- or, (R,S)-methadone.

The methods for the synthesis of (S)-methadone, (R)-methadone, (R,S)-methadone and analogues disclosed herein were envisioned and developed by the present inventors as enantio-retentive, scalable, three-stage processes concluding with the isolation of the (R), (S), or (R,S)-methadone in the hydrochloric salt form. Referring to FIG. 3, major features of these methods are the strategic exploitation of the chiral pool employing (R), (S), or (R,S)-alaninol-derived N-protected cyclic 4-methyl-sulfamidate (1), or N-protected 2-methylaziridine (2) as key starting materials of the synthetic process. The N-protecting group can be chosen among the most common carbamate protecting groups for amines [e.g., fluorenylmethyloxycarbonyl (Fmoc), tert-butyloxycarbonyl (Boc), carboxybenzyl (Cbz), acetyl ($C(O)CH_3$), trifluoroacetyl ($C(O)CF_3$), benzyl (Bn), triphenylmethyl ($CPh_3$), p-toluenesulfonyl (Ts)].

Previously reported processes for the synthesis of (R)- and (S)-methadone consist of nucleophilic ring-opening reactions of aziridiniums. However, these technologies suffer from poor regioselectivity, resulting in isomeric impurities complicating purification and isolation of the desired nitrile intermediate (see, e.g., the processes disclosed in US 2020/0277250 A1; WO, 2017/035225 A1; WO 2017/035524 A1; US 2000/6143933; and US 2018/10040752 B2). Furthermore, unlike the ring-opening of N-protected cyclic 4-methyl-sulfamidate (1) or N-protected 2-methylaziridine (2), the aziridinium strategy can result in loss of optical purity, requiring resolution techniques for the isolation of enantiopure material (as in WO 2013/077720 A1; WO 1997/45551 A1; IN 2014/MU04118 A; US 2015/9212128 B2).

In the disclosed methods in accordance with aspects of the present invention—and still referring to FIG. 3—Stage 1 of the present method was useful for the minimization of regioisomeric by-products observed in previous synthesis (i.e. isomethadone-nitrile). Employing N-protected cyclic 4-methyl-sulfamidate (1) as starting material for the reaction with 2,2-diphenylacetonitrile (3) in the presence of a base, resulted in excellent yield and purity of the N-protected intermediate (4) following crystallization. Similarly, reaction of N-protected 2-methylaziridine (2) with 2,2-diphenylacetonitrile (3) in the presence of a base, resulted in good yield and efficient conversion to the N-protected intermediate (4) after purification.

Stage 2 of the present method (as noted above) is a two-step/one-pot deprotection/reductive amination of the N-protected intermediate (4), resulting in the synthesis of common intermediate (R)-, (S)-, or (R,S)-methadone nitrile (5), in good yield and purity. Reaction conditions of Stage 2 depend on the N-protecting group adopted, as shown in the Examples provided below.

In Stage 3 of the present method (as noted above), treatment of the intermediate (R)-, (S)-, or (R,S)-methadone nitrile (5) with a slight excess of EtMgBr (one example of a organomagnesium halide agent) resulted in the generation of the corresponding ethyl-imine, which was hydrolyzed under acidic conditions to provide (R)-, (S)-, or (R,S)-methadone as already disclosed. The desired (R)-, (S)-, or (R,S)-methadone was isolated via a seeded crystallization in good yield and high purity.

Figure 4:
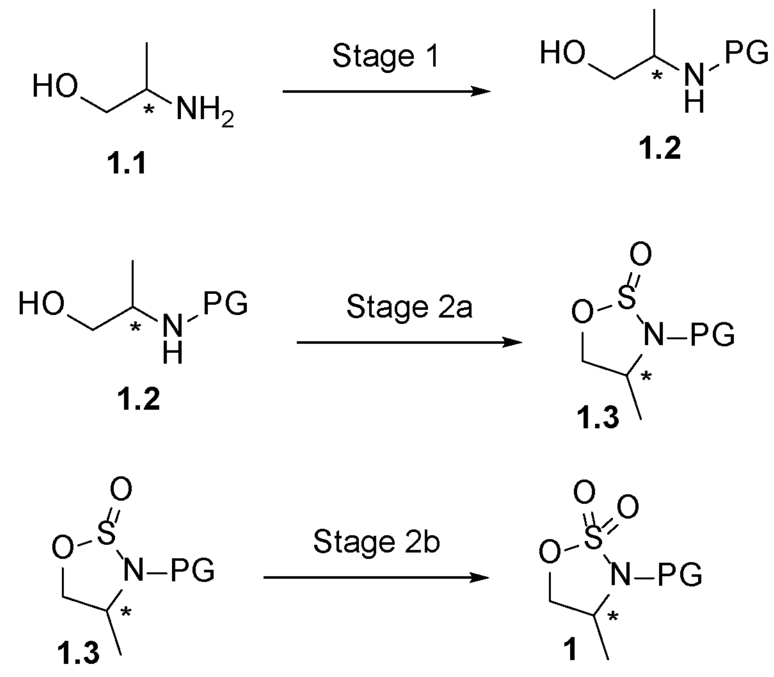
FIG. 4 is a schematic representation of a procedure for preparation of N-protected cyclic sulfamidate starting material.

Referring now to FIG. 4, N-protected cyclic 4-methyl-sulfamidate (one possible starting material) can be produced in a two-stage process starting from (R)-, (S)-, or (R,S)-2-aminopropan-1-ol (1.1). The first stage is the protection of the amino group with the selected protecting group to obtain the corresponding N-protected (R)-, (S)-, or (R,S)-2-amino-propan-1-ol (1.2). The second stage is a two-steps/one-pot process to obtain first the N-protected cyclic sulfamidite intermediate (1.3 in Stage 2a) by cyclization reaction with thionyl chloride in the presence of a base followed by the oxidation of the sulfur atom in the presence of sodium periodate as an oxidizing agent and ruthenium chloride as a catalyst (Stage 2b) to obtain the desired N-protected cyclic sulfamidate (1) in good yield and purity after crystallization (See FIG. 4).

Figure 5:
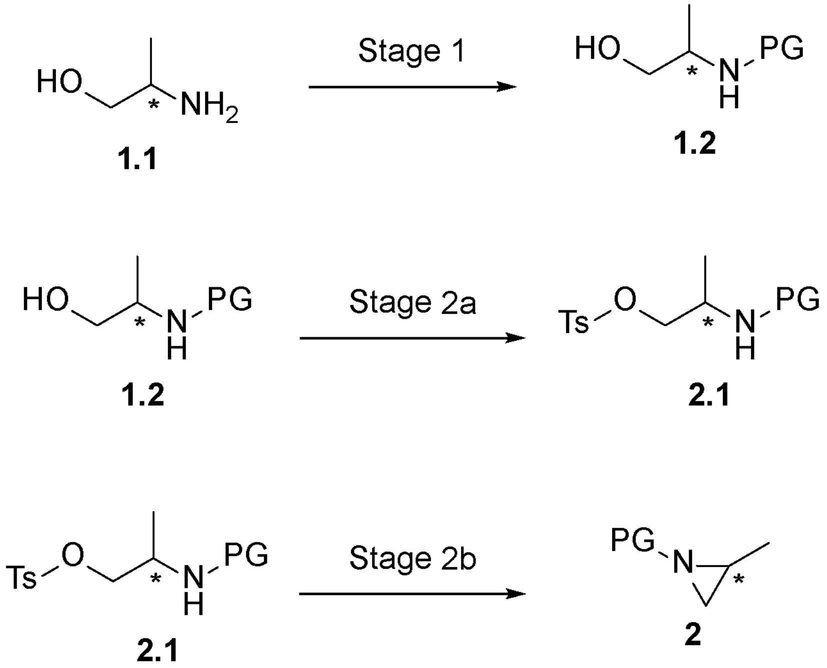
FIG. 5 is a schematic representation of the preparation of N-protected 2-methylaziridine starting material.

N-protected 2-methylaziridine (an alternate starting material) can be produced in a two-stage process as already disclosed for example in WO 2012/014109 or WO2019/52545 starting from (R)-, (S)-, or (R,S)-2-aminopropan-1-ol (1.1). Referring to FIG. 5, the first stage in this production is the protection of the amino group with the selected carbamate protecting group to obtain the corresponding N-protected (R)-, (S)-, or (R,S)-2-aminopropan-1-ol (1.2). The second stage is a two-step/one-pot process to obtain initially the N-protected (R)-, (S)-, or (R,S)-2-aminopropan-1-tosylate intermediate (2.1 in Stage 2a) by reaction with p-toluenesulfonyl chloride in the presence of a base followed by aziridine ring closure (Stage 2b) to obtain the desired N-protected 2-methylaziridine (2) in good yield and purity.

Figure 6:
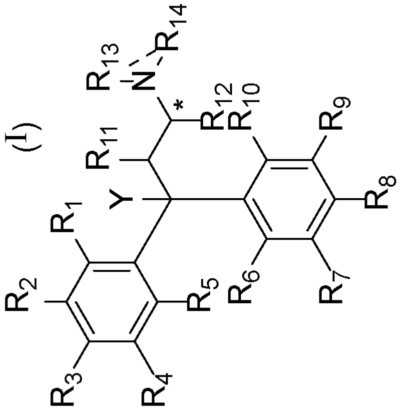
FIG. 6 shows the general structure of enantiopure or racemic methadone analogues that can be synthesized using the disclosed methods.

As mentioned above, the methods disclosed herein are also applicable to the synthesis of methadone analogues according to the general Formula (I)—shown below and also in FIG. 6:

(I)

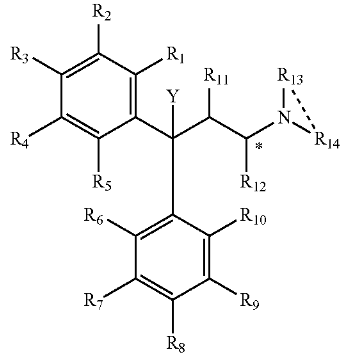

wherein:

$R_1$ to $R_{10}$ are, independently for each occurrence, hydrogen, deuterium, halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate;

$R_{11}$ and $R_{12}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or $R_{11}$ and $R_{12}$ are, independently for each occurrence, selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; $NR_{13}R_{14}$ is optionally cyclized through $C_3$-$C_{12}$ cycloalkyl, or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate;

If $NR_{13}R_{14}$ is not cyclized $R_{13}$ and $R_{14}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, or $R_{13}$ and $R_{14}$ are, independently for each occurrence, selected from the group consisting of alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate;

Y is cyano, —C(O)$R_{15}$, —C(OH)$R_{15}$, —C($OR_{16}$)$R_{15}$. $R_{15}$ and $R_{16}$ are, independently for each occurrence, hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or $R_{15}$ and $R_{16}$ are, independently for each occurrence, selected from the group consisting of alkyl ester, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; and

* is a stereocenter selected from (R)-, (S)- or (R,S)-configuration, wherein the Stereocenter is in an R configuration, and wherein the compound is present in greater than 90%, 95%, 97%, 99%, 99.5%, or 99.9% enantiomeric excess (e.e) compared to the S isomer, or wherein the stereocenter is in an S configuration, and wherein the compound is present in greater than 90%, 95%, 97%, 99%, 99.5%, or 99.9% enantiomeric excess (e.e) compared to the R isomer.

EXAMPLES

The compound structures in the examples below were confirmed by one or more of the following methods: $^1$H NMR, $^{13}$C NMR, mass spectrometry (LC-MS), FTIR spectroscopy, HPLC-UV, Chiral-HPLC. $^1$H NMR spectra were determined using an NMR spectrometer operating at 300 MHz or 400 MHz field. Chemical shifts were referenced to signals from residual protons in deuterated solvents as follows: $CDCl_3$=7.25 ppm, DMSO-$d_6$=2.49 ppm, $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz).

Mass spectra (MS) data are obtained using a mass spectrometer with ESI ionization and Ion trap or TOF mass analyzer.

In the examples below, reagents and solvents may be purchased from commercial suppliers, and may be used without further purification unless otherwise indicated.

Example 1: benzyl (S)-4-methyl-L2,3-oxathiazolidine-3-carboxylate 2,2-dioxide ((S)-1')

Figure 7:
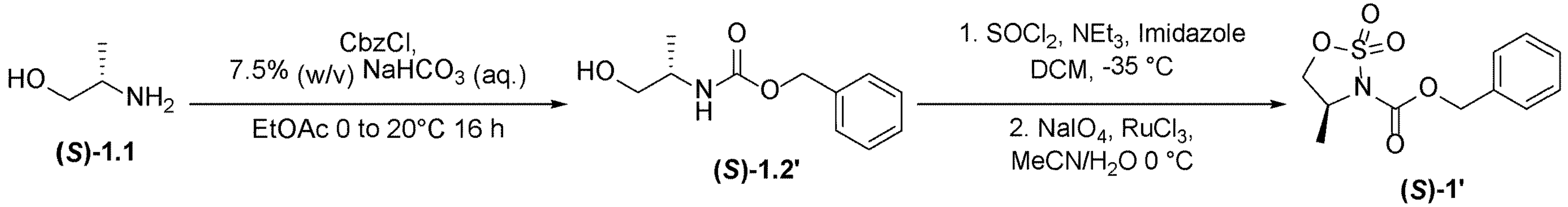
FIG. 7 is a schematic showing the synthesis of Cbz-protected (S)-cyclic sulfamidate starting material.

This Example 1 describes a two-step method that was used to prepare benzyl (S)-4-methyl-1,2,3-oxathiazolidine-3-carboxylate 2,2-dioxide ((S)-1'), as shown in FIG. 7.

Step 1: Cbz protection of (S)-2-aminopropan-1-ol ((S)-1.1) to form benzyl (S)-(1-hydroxypropan-2-yl)carbamate ((S)-1.2').

Figure 8:
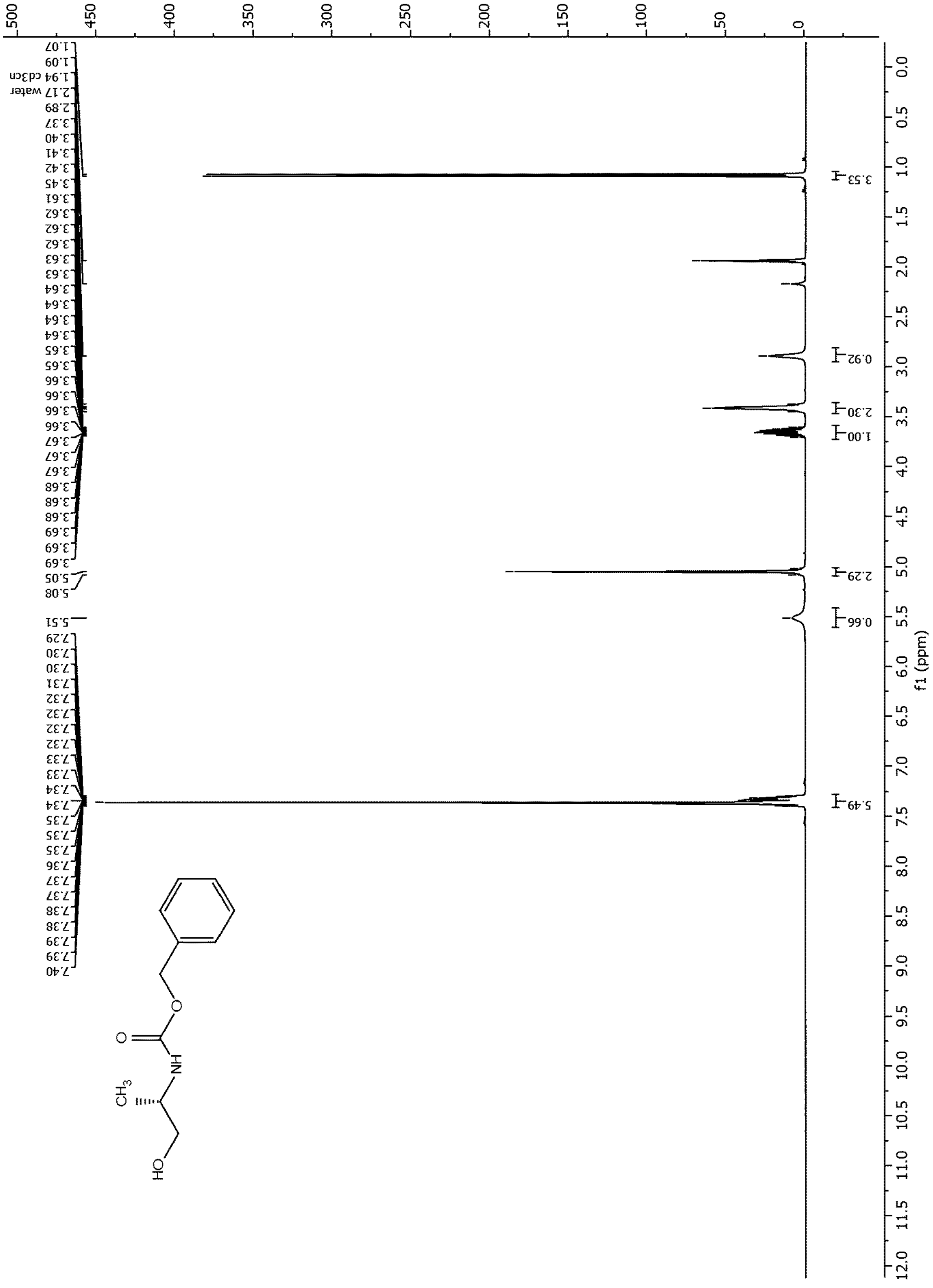
FIG. 8 is a graph showing the $^{1}H$ NMR spectrum of benzyl (S)-(1-hydroxypropan-2-yl)carbamate.

To a 5 L round bottom flask equipped with an overhead mechanical stirrer, thermocouple, $N_2$ inlet, and addition funnel was added (S)-2-aminopropan-1-ol ((S)-1.1) (100.0 g, 1331 mmol, 1.0 equiv.), EtOAc (1000 mL, 10 vol.), and 7.5% (w/v) $NaHCO_3$ (aq.) (1000 mL, 10 vol.). The stirring solution was cooled to 0° C. via an ice-water bath and CbzCl (209.0 mL, 1460 mmol, 1.1 equiv.) was added over 25 min via addition funnel. The biphasic reaction was allowed to equilibrate to an internal temperature of 20° C. over 16 h. Upon reaction completion, as determined by consumption of (S)-1.1 by $^1$H-NMR and TLC (DCM:MeOH [9:1 ratio] using ceric ammonium molybdate stain, Rf=~0.6), stirring was discontinued and the biphasic mixture was allowed to settle. The organic fraction was separated, and the aqueous fraction was extracted further with IPAc (2×500 mL, 5 vol.). The combined organic layers were washed with 36% (w/v) NaCl (aq) (100 mL, 1 vol.) and evaporated under reduced pressure to provide a clear colorless oil. The crude material was diluted with IPAc (2.8 V, 280-mL) and warmed to 45° C. with rotary agitation. Dissolution was not complete after 45 minutes, so additional IPAc (2.8 V, 280-mL) was added and heating with stirring was continued. Dissolution was complete after 1 h. Heating was discontinued, and the solution was seeded with authentic ((S)-1.2') (approx. 100 mg). Moderate stirring (200-250 rpm) was continued while equilibrating to 20° C. over 16 h to provide a free-flowing slurry. The solids were collected via vacuum filtration and dried under reduced pressure at 45° C. to provide benzyl (S)-(1-hydroxypropan-2-yl)carbamate ((S)-1.2') as a white solid (185.9 g, 67% yield) from a single crop. An additional crystallization attempt was performed via concentration of the mother liquor followed by seeding with authentic ((S)-1.2') to provide a free-flowing slurry that was subsequently filtered and dried under reduced pressure to give an additional 21.4 g of benzyl (S)-(1-hydroxypropan-2-yl)carbamate ((S)-1.2') as a white solid. Combined total amount isolated after the second crop: 207.3 g, 74% yield. $^1$H NMR (400 MHz, Acetonitrile-$d_3$) δ 7.41-7.28 (m, 5H), 5.51 (s, 1H), 5.10-5.01 (m, 2H), 3.72-3.59 (m, 1H), 3.47-3.35 (m, 2H), 2.89 (s, 1H), 1.08 (d, J=6.8 Hz, 3H), as shown in FIG. 8.

Step 2: Two-step/one-pot cyclization/oxidation to form benzyl (S)-4-methyl-1,2,3-oxathiazolidine-3-carboxylate 2,2-dioxide ((S)-1').

To a 400 mL Easy Max Reactor equipped with an overhead mechanical stirrer, thermocouple, and $N_2$ inlet was added imidazole (32.54 g, 477.9 mmol, 4.0 equiv.), DCM (100 mL, 4 vol.), and $NEt_3$ (37 mL, 262.8 mmol, 2.2 equiv.). The vessel was purged with $N_2$ for 30 min and cooled to an internal temperature of −35° C. To the stirring suspension was added a solution of thionyl chloride (9.5 mL, 131.4 mmol, 1.1 equiv.) in DCM (50 mL, 2 vol.) over 2 h, via syringe pump, and allowed to stir for an additional 15 min. To the resultant suspension was added a solution of benzyl (S)-(1-hydroxypropan-2-yl)carbamate ((S)-1.2') (25.00 g, 119.5 mmol, 1.0 equiv.) in DCM (100 mL, 4 vol.) over 1 h, via syringe pump. The reaction was warmed to −30° C. and allowed to stir for 15 h. Upon reaction completion, as determined by consumption of 2 by HPLC and $^1$H NMR, the reaction was warmed to 0° C. over 2 h. The reaction was washed with $H_2O$ (2×10 vol.) and the organic fraction was concentrated under reduced pressure. The crude oil was reconstituted in MeCN (100 mL, 4 vol.) and $H_2O$ (125 mL, 5 vol.) then cooled to an internal temperature of 0° C. To the stirring solution was added $NaIO_4$ (28.11 g, 131.4 mmol, 1.1 equiv.) followed by $RuCl_3$ (25 mg, 0.12 mmol, 0.001 equiv.) and the solution was agitated for 3 h at 0° C. Upon reaction completion, as determined by consumption of the intermediate sulfamidite by HPLC and $^1$H NMR, the reaction was treated with a pH=7 $KH_2PO_4$/KOH buffer (aq) (250 mL, 10 vol.) and PhMe (100 mL, 4 vol.). The MeCN was removed under reduced pressure and the organic and aqueous fractions were separated. The aqueous fraction (pH=7) was extracted further with IPAc (2×4 vol.), and the combined organic layers were concentrated under reduced pressure to an estimated 50 mL (~2 V). The solution was warmed to 45°

Figure 9:
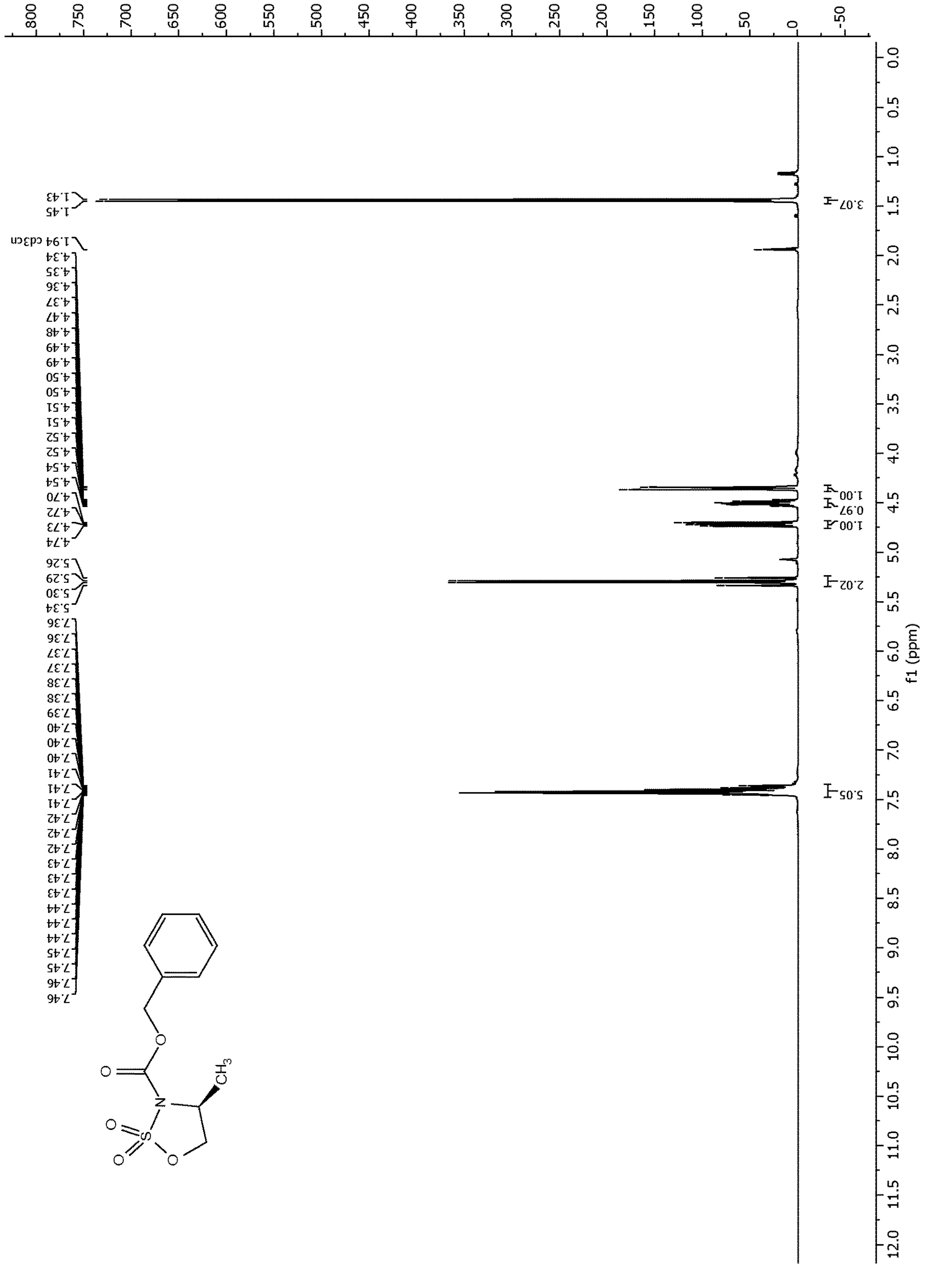
FIG. 9 is a graph showing the $^{1}H$ NMR spectrum of benzyl (S)-4-methyl-1,2,3-oxathiazolidine-3-carboxylate 2,2-dioxide.
Figure 10:
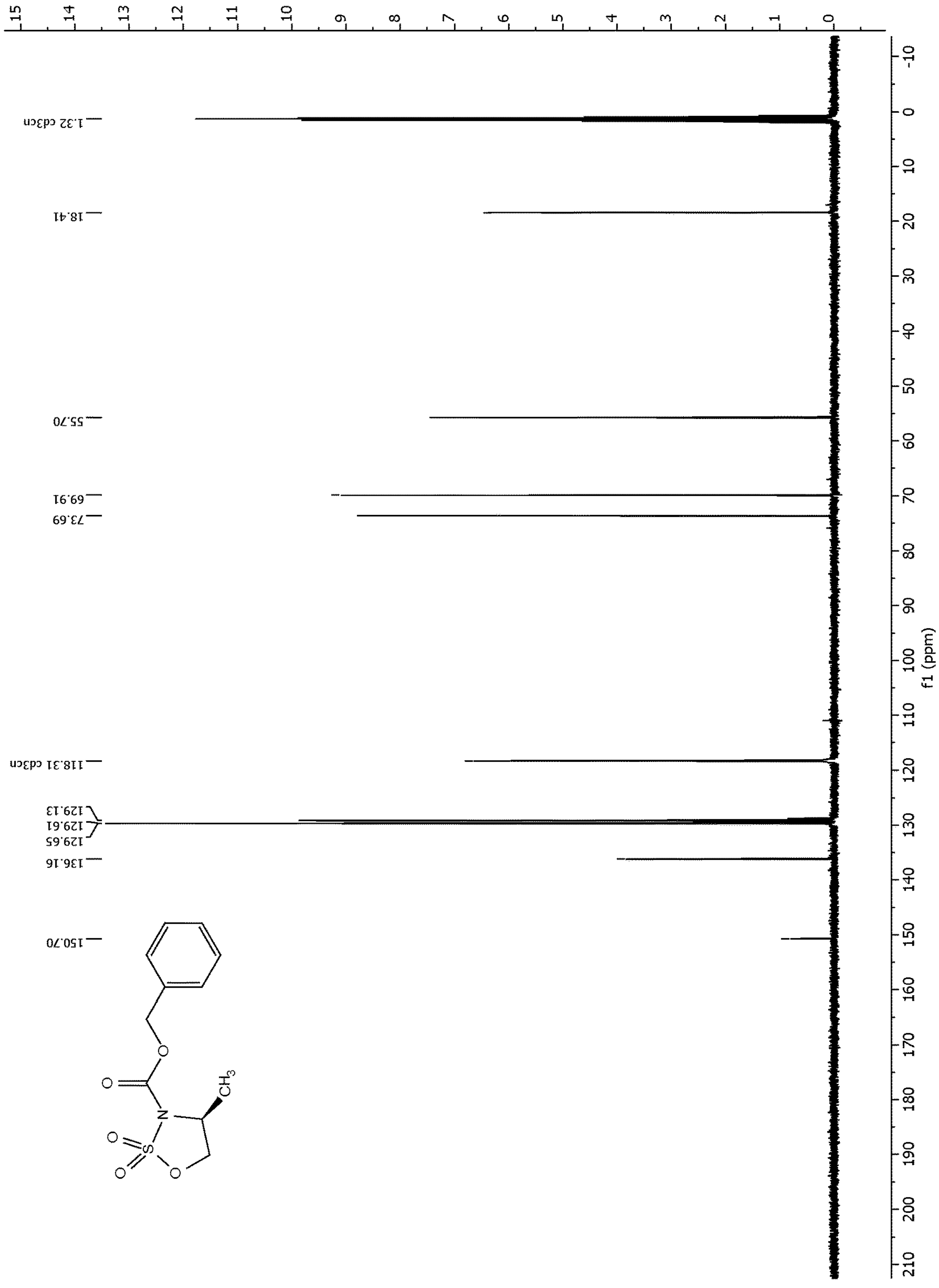
FIG. 10 is a graph showing the $^{13}C$ NMR spectrum of benzyl (S)-4-methyl-1,2,3-oxathiazolidine-3-carboxylate 2,2-dioxide.

C. and seeded with authentic (S)-3-Cbz-4-methyl-1,2,3-oxathiazolidine 2,2-dioxide 3. To the stirring suspension was added n-heptane (250 mL, 10 vol.) dropwise over 1 h to provide a white slurry. The suspension was cooled and allowed to stir at 20° C. for 1 h, gradually cooled to −20° C. over 2 h, then stirred for an additional 15 h. The slurry was filtered, and the solids were washed with n-heptane (4 vol.). The collected solids were dried under reduced pressure at 20° C. to provide benzyl (S)-3-Cbz-4-methyl-1,2,3-oxathiazolidine 2,2-dioxide ((S)-1') as a white solid (27.17 g, 84% yield). $^1$H NMR (400 MHz, Acetonitrile-$d_3$) δ 7.48-7.34 (m, 5H), 5.36-5.23 (m, 2H), 4.72 (dd, J=9.4, 5.8 Hz, 1H), 4.56-4.45 (m, 1H), 4.35 (dd, J=9.4, 2.3 Hz, 1H), 1.44 (d, J=6.4 Hz, 3H), as shown in FIG. 9. $^{13}$C NMR (101 MHz, Acetonitrile-$d_3$) δ 150.70, 136.16, 129.65, 129.61, 129.13, 73.69, 69.91, 55.70, 18.41, as shown in FIG. 10.

Example 2: tert-butyl (R)-2-methylaziridine-1-carboxylate ((R)-2")

Figure 11:
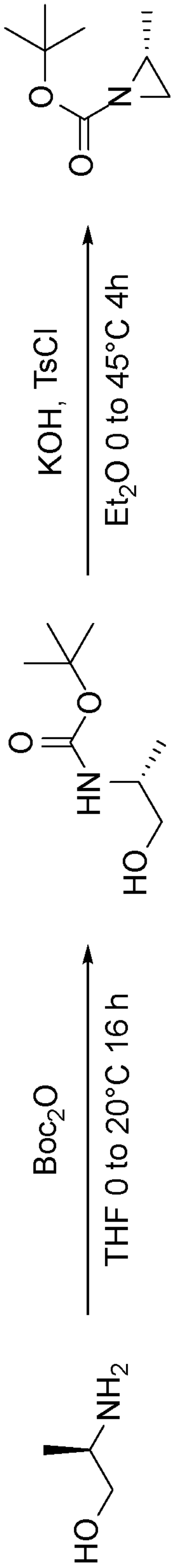
FIG. 11 is a schematic showing the synthesis of Boc-protected (R)-aziridine starting material.

This Example 2 describes a two-step method that was used to prepare tert-butyl (R)-2-methylaziridine-1-carboxylate ((R)-2"), as shown in FIG. 11.

Step 1: Boc protection of (R)-2-aminopropan-1-ol ((R)-1.1) to form tert-butyl (R)-(1-hydroxypropan-2-yl)carbamate ((R)-2.2"). This step was carried out by following literature procedures (see WO 2014/159224, incorporated by reference herein in its entirety) with modifications.

Figure 12:
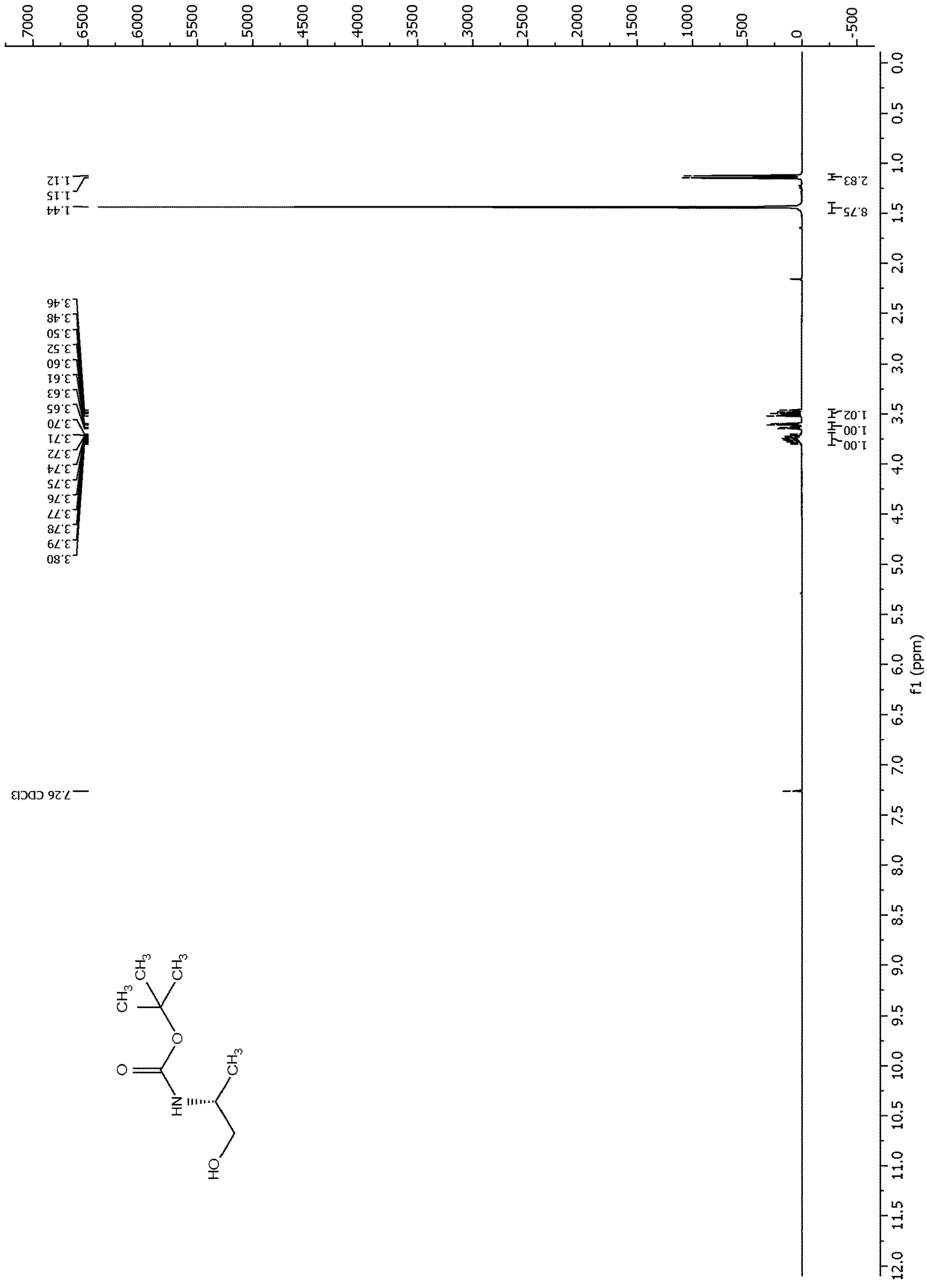
FIG. 12 is a graph showing the $^{1}H$ NMR spectrum of tert-butyl (R)-(1-hydroxypropan-2-yl)carbamate.
Figure 13:
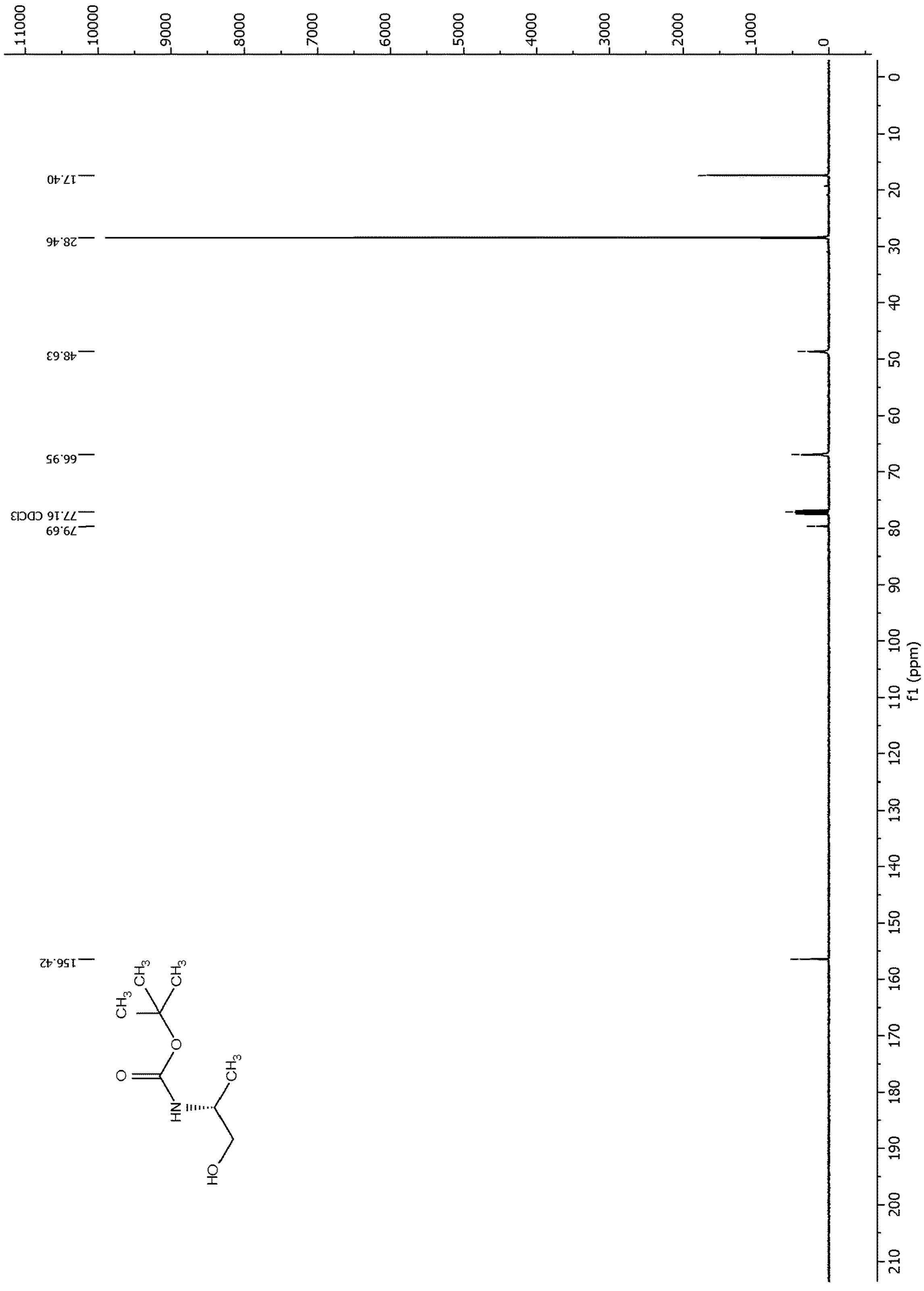
FIG. 13 is a graph showing the $^{13}C$ NMR spectrum of tert-butyl (R)-(1-hydroxypropan-2-yl)carbamate.

To a 250 mL round bottom flask under $N_2$ atmosphere was added (R)-2-aminopropan-1-ol ((R)-1.1) (10.0 g, 133.1 mmol, 1.0 equiv.) and anhydrous THF (100 mL). The flask was cooled to 0° C. and a solution of $Boc_2O$ (30.52 g, 139.8 mmol, 1.05 eq.) in anhydrous THF (40 mL) was added dropwise over 30 minutes. The reaction mixture was stirred at 0° C. for a further 1 h and then warmed to 20° C. over a further 16 h. Upon reaction completion, as determined by consumption of (R)-1.1 by $^1$H-NMR and TLC (DCM: MeOH [9:1 ratio] using potassium permanganate stain, Rf=~0.6), stirring was discontinued. The organics were concentrated under reduced pressure and the residue was triturated with n-hexane. The resulting solid was filtered and air dried to give the title compound ((R)-2.2") as a colorless solid (20.81 g, 89% yield). HRMS (ESI): m/z calculated for $C_8H_{17}NO_3+Na^+$ $[M+Na]^+$: 198.1101. Found: 198.0791. $^1$H NMR (300 MHz, $CDCl_3$) δ 3.81-3.69 (m, 1H), 3.62 (dd, J=10.9, 3.9 Hz, 1H), 3.49 (dd, J=10.9, 6.1 Hz, 1H), 1.44 (s, 9H), 1.14 (d, J=6.8 Hz, 3H) ppm as shown in FIG. 12. $^{13}$C NMR (101 MHz, $CDCl_3$) δ 156.42, 79.69, 66.95, 48.63, 28.46, 17.40 ppm as shown in FIG. 13.

Step 2: Two-step/one-pot tosylation/cyclization to form tert-butyl (R)-2-methylaziridine-1-carboxylate ((R)-2"). This step was carried out by following literature procedures (see WO 2012/14109, incorporated by reference herein in its entirety) with modifications.

Figure 14:
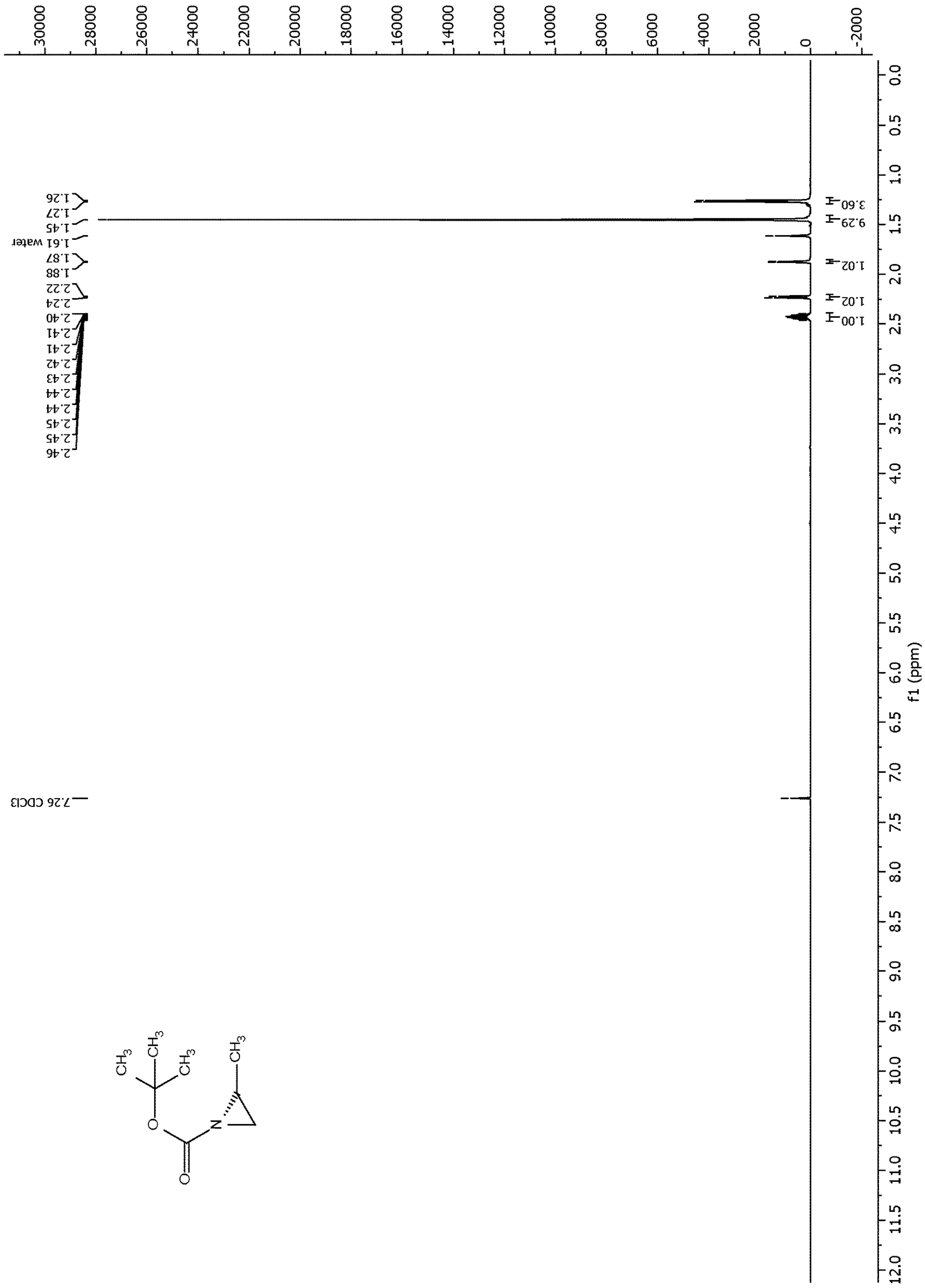
FIG. 14 is a graph showing the $^{1}H$ NMR spectrum of tert-butyl (R)-2-methylaziridine-1-carboxylate.
Figure 15:
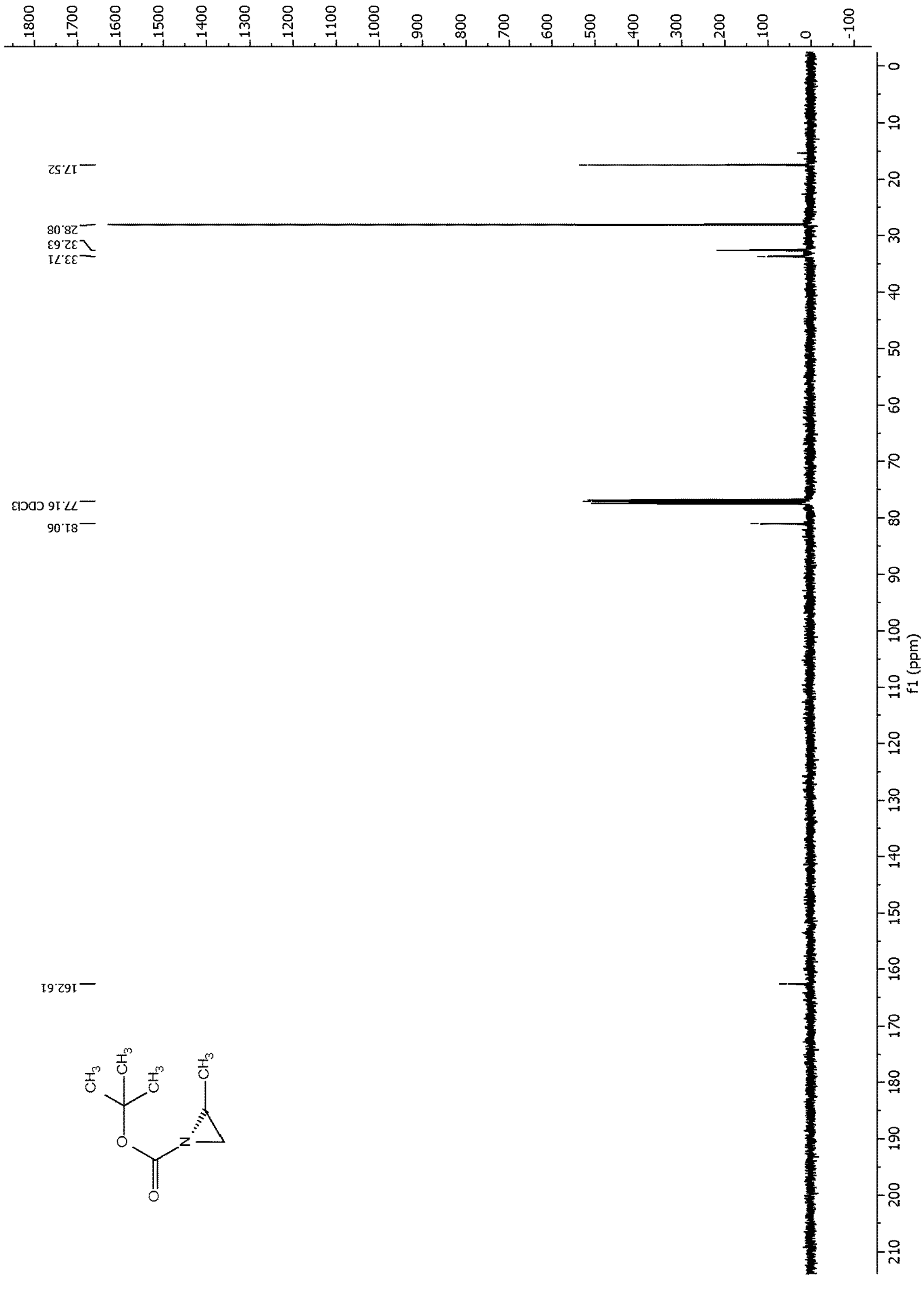
FIG. 15 is a graph showing the $^{13}C$ NMR spectrum of tert-butyl (R)-2-methylaziridine-1-carboxylate.

To a 250 mL round bottom flask under $N_2$ atmosphere was added tert-butyl (R)-(1-hydroxypropan-2-yl)carbamate ((R)-2.2") (10.00 g, 57.1 mmol, 1 equiv.), anhydrous diethyl ether (120 ml) and tosyl chloride (14.14 g, 74.2 mmol, 1.3 equiv.). The reaction mixture was stirred for 15 minutes and then cooled to 0° C. Crushed potassium hydroxide (25.62 g, 456.8 mmol, 8 equiv.) was added portion-wise over 30 minutes. The reaction mixture was warmed at 45° C. for about 3 hours, and upon reaction completion, as determined by consumption of (R)-2.2' by $^1$H-NMR and TLC (Hex: EtOAc [8:2 ratio] using potassium permanganate stain, Rf=~0.3), stirring was discontinued. Reaction mixture was diluted with water (100 mL), the organic fraction was separated, and the aqueous fraction was extracted further with diethyl ether (2×50 mL). The combined organic layers were washed with 36% (w/v) NaCl (aq) (100 mL) and evaporated under reduced pressure to provide tert-butyl (R)-2-methylaziridine-1-carboxylate ((R)-2") as a clear colorless oil (7.04 g, 78% yield). $^1$H NMR (400 MHz, $CDCl_3$) δ 2.48-2.39 (m, 1H), 2.23 (d, J=5.8 Hz, 1H), 1.88 (d, J=3.8 Hz, 1H), 1.45 (s, 9H), 1.27 (d, J=5.5 Hz, 3H) ppm as shown in FIG. 14. $^{13}$C NMR (101 MHz, $CDCl_3$) δ 162.61, 81.06, 33.71, 32.63, 28.08, 17.52 ppm as shown in FIG. 15.

Example 3: (S)-4-(dimethylamino)-2,2-diphenylpentanenitrile ((S)-5)

Figure 16:
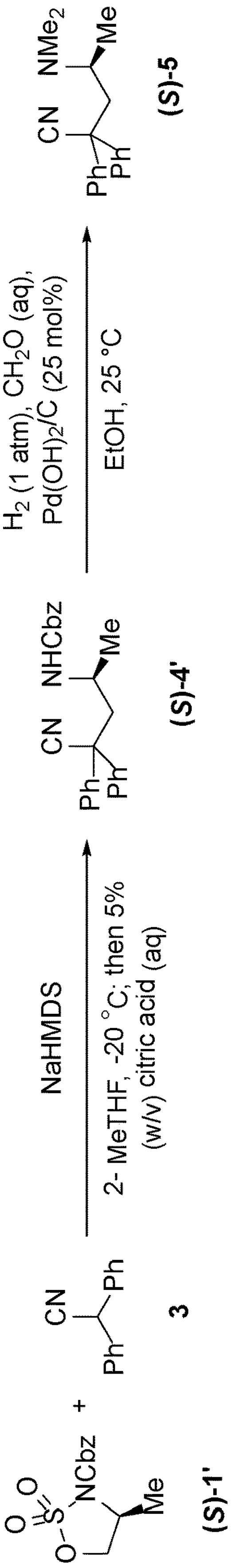
FIG. 16 is a schematic showing the synthesis of (S)-methadone nitrile using Cbz-protected (S)-cyclic sulfamidate starting material.

This Example 3 describes a two-step method that was used to prepare (S)-4-(dimethylamino)-2,2-diphenylpentanenitrile ((S)-5), as shown in FIG. 16.

Step 1: Ring-opening reaction of benzyl (S)-4-methyl-1,2,3-oxathiazolidine-3-carboxylate 2,2-dioxide ((S)-1') on the 2,2-diphenylacetonitrile (3) anion to form benzyl (S)-(4-cyano-4,4-diphenylbutan-2-yl)carbamate ((S)-4').

Figure 17:
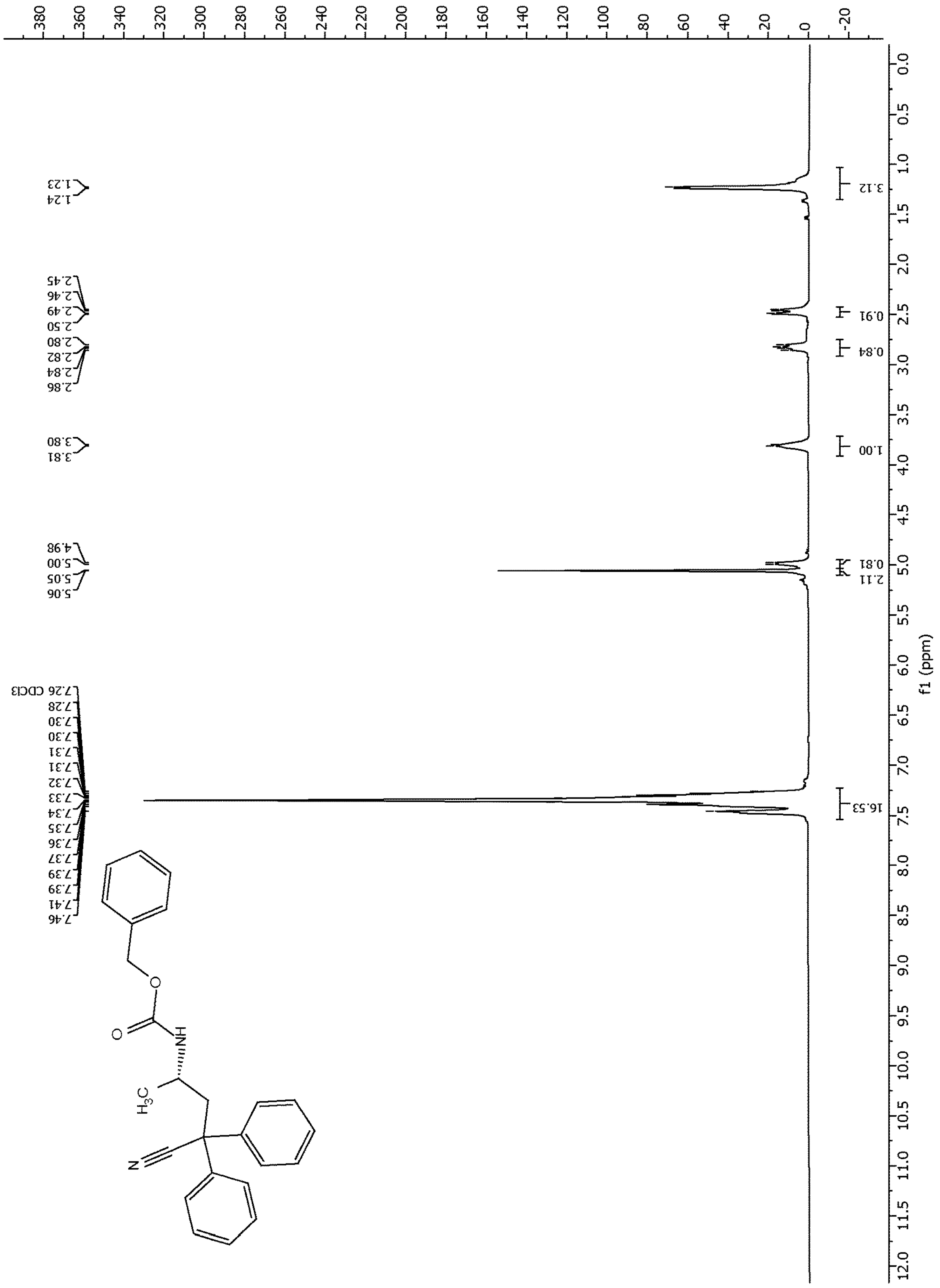
FIG. 17 is a graph showing the $^{1}H$ NMR spectrum of benzyl (S)-(4-cyano-4,4-diphenylbutan-2-yl)carbamate.
Figure 18:
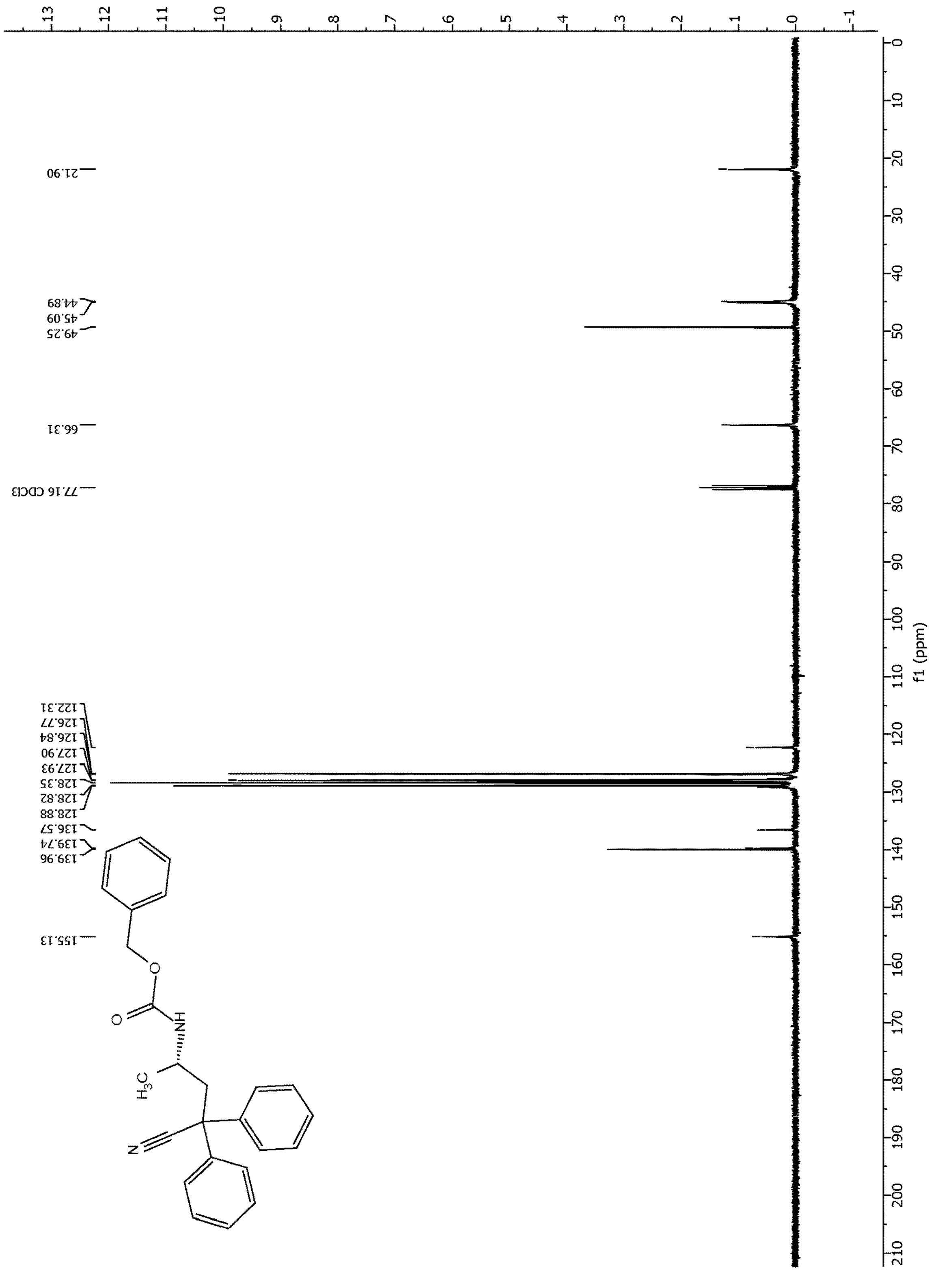
FIG. 18 is a graph showing the $^{13}C$ NMR spectrum of benzyl (S)-(4-cyano-4,4-diphenylbutan-2-yl)carbamate.

To a 400 mL Easy Max Reactor equipped with an overhead mechanical stirrer, thermocouple, and $N_2$ inlet was added benzyl (S)-4-methyl-1,2,3-oxathiazolidine-3-carboxylate 2,2-dioxide ((S)-1') (10.00 g, 36.9 mmol, 1 equiv.) and diphenylacetonitrile (3) (7.85 g, 40.6 mmol, 1.1 equiv.). The vessel was purged with $N_2$ for 30 min, diluted with 2-MeTHF (100 mL, 10 vol.), and cooled to an internal temperature of −20° C. To the stirring solution was added NaHMDS (1 M in THF, 44.3 mL, 44.3 mmol, 1.2 equiv.) dropwise over 1 h, via syringe pump, and allowed to stir for an additional 15 h. The mixture was warmed to 0° C. and stirred for 1 h. Upon reaction completion, as determined by consumption of (S)-1' by HPLC, the solution was treated with 5% (w/v) citric acid (aq.) (50 mL, 5 vol.) added dropwise over 1 h. The biphasic mixture was warmed to 20° C. then the organic and aqueous fractions were separated. The aqueous fraction was extracted further with 2-MeTHF (2×50 mL, 5 vol.). The combined organic layers were concentrated under reduced pressure to an estimated 20 mL (~2 vol.) at 35° C. To the stirring solution was added n-heptane (100 mL, 10 vol.), dropwise over 1 h, then seeded with authentic benzyl (S)-(4-cyano-4,4-diphenylbutan-2-yl) carbamate ((S)-4') to provide an off-white slurry. The slurry was allowed to stir at 20° C. for 6 h, gradually cooled to −20° C. over 15 h (~3° C./h), then stirred for an additional 15 h. The slurry was filtered, and the solids were washed with n-heptane (3×10 vol.). The collected solids were dried under reduced pressure at 20° C. to provide benzyl (S)-(4-cyano-4,4-diphenylbutan-2-yl)carbamate ((S)-4') as a white solid (13.62 g, 96% yield). Purity HPLC: 97.9%. HRMS (ESI) m/z: $[M+H]^+$ Required $C_{25}H_{24}N_2O_2$ 385.19; Found 385.20. $^1$H NMR (400 MHz, $CDCl_3$) δ 7.51-7.20 (m, 15H), 5.06 (s, 2H), 4.99 (d, J=8.3 Hz, 1H), 3.86-3.74 (m, 1H), 2.83 (dd, J=14.4, 8.0 Hz, 1H), 2.48 (dd, J=14.4, 4.7 Hz, 1H), 1.24 (d, J=6.7 Hz, 3H) ppm, as shown in FIG. 17. $^{13}$C NMR (400 MHz, $CDCl_3$) δ 155.13, 139.96, 139.74, 136.57, 128.88, 128.82, 128.35, 127.93, 127.90, 126.84, 126.77, 122.31, 66.31, 49.25, 45.09, 44.89, 21.90 ppm, as shown in FIG. 18.

Step 2: Two-step/one-pot deprotection/reductive amination of benzyl (S)-(4-cyano-4,4-diphenylbutan-2-yl)carbamate ((S)-4') to form (S)-methadone nitrile ((S)-5).

Figure 19A:
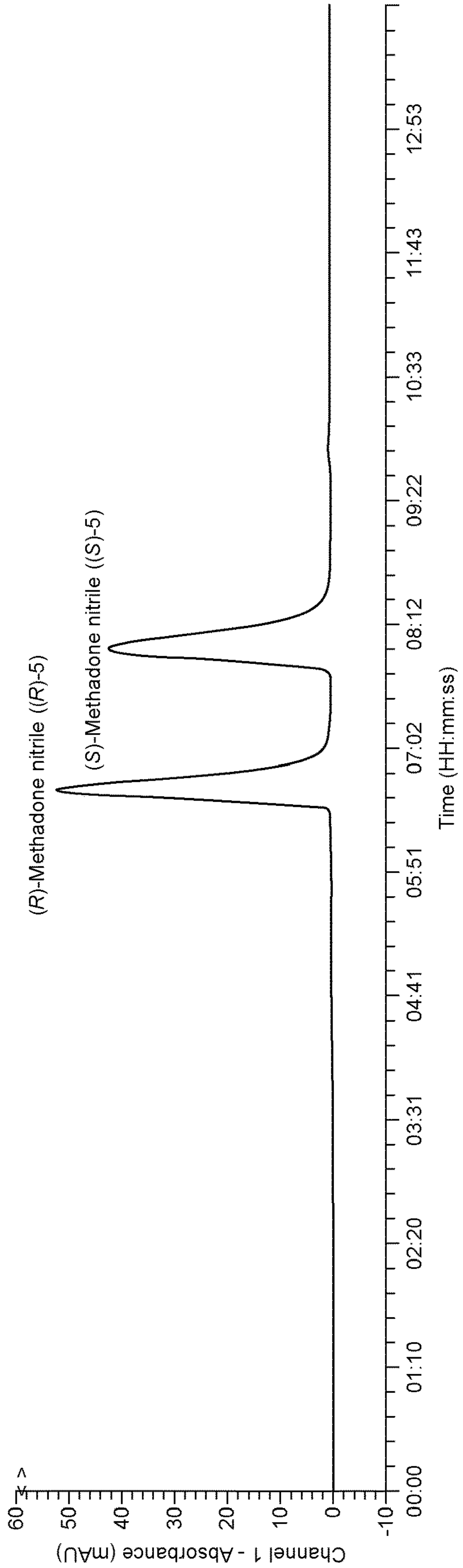
FIG. 19A is a graph and table showing a Chiral HPLC chromatogram of (R,S)-methadone nitrile.
Figure 19B:
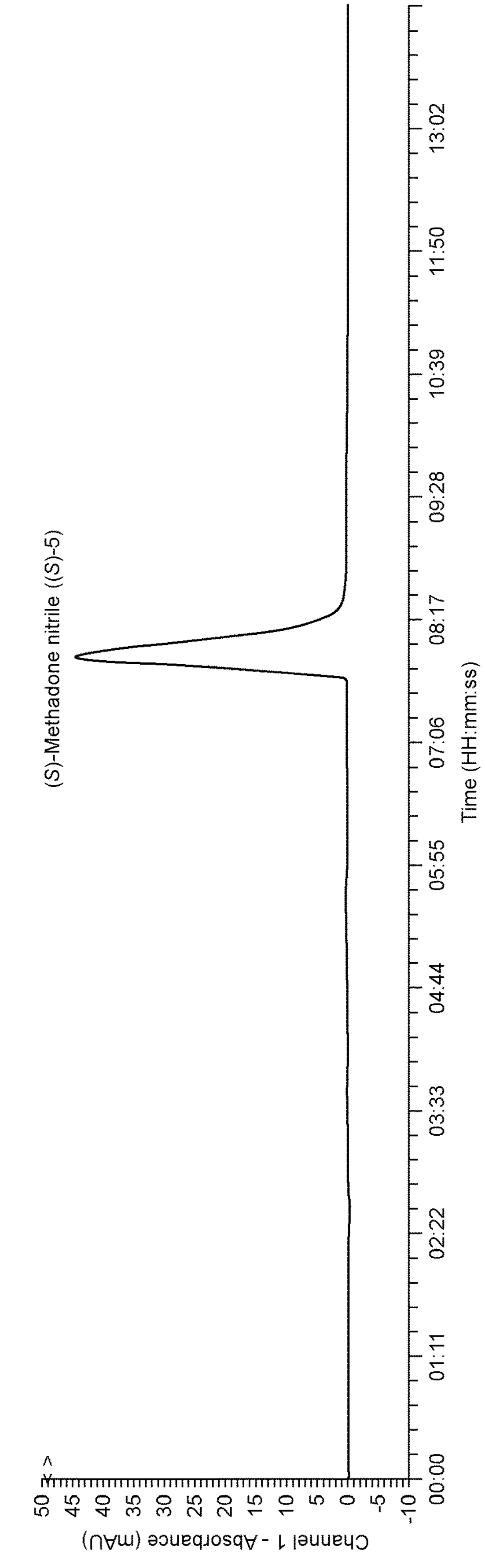
FIG. 19B is a graph and table showing a Chiral HPLC chromatogram of (S)-methadone nitrile.
Figure 20:
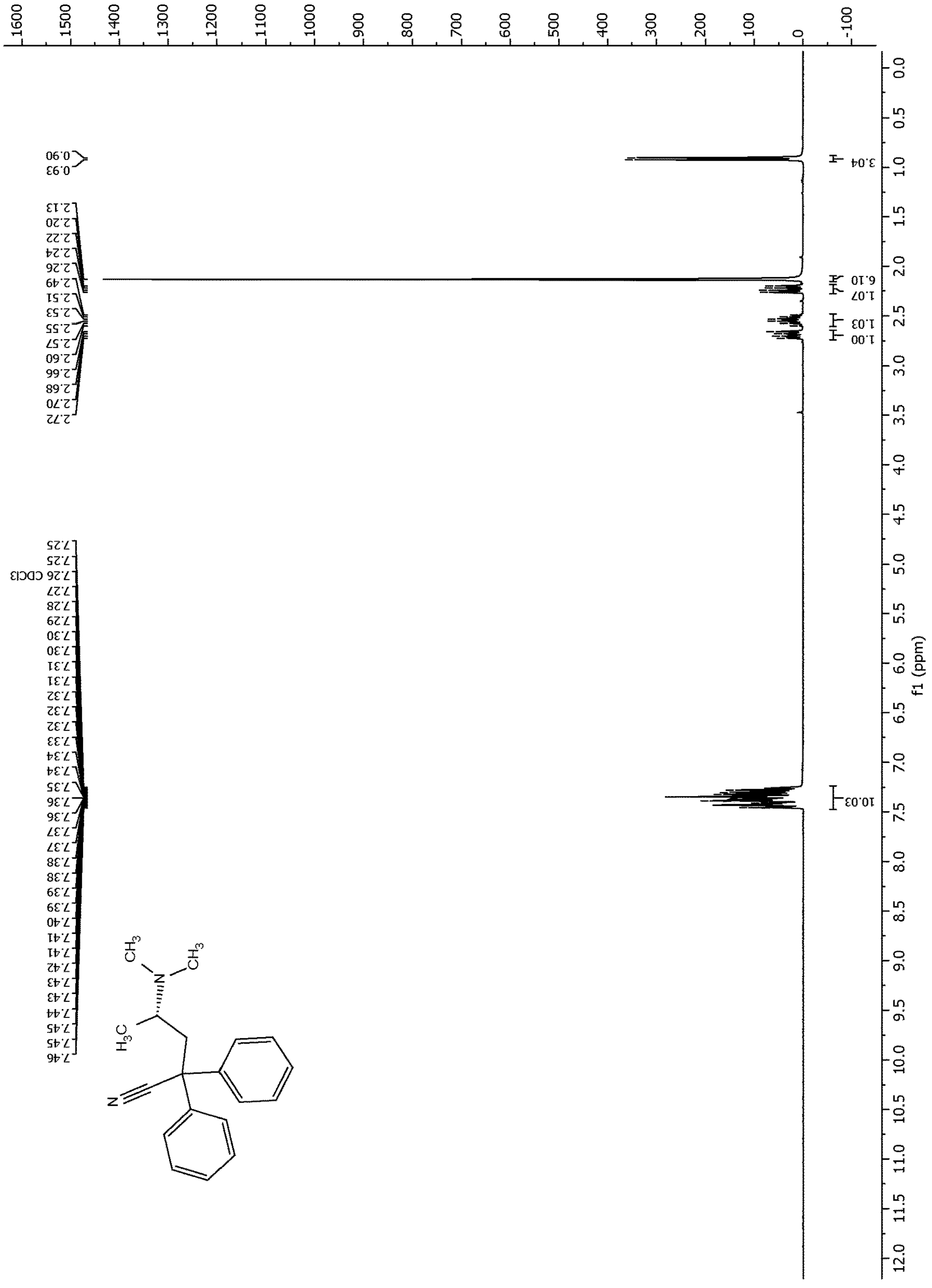
FIG. 20 is a graph showing the $^{1}H$ NMR spectrum of (S)-methadone nitrile.
Figure 21:
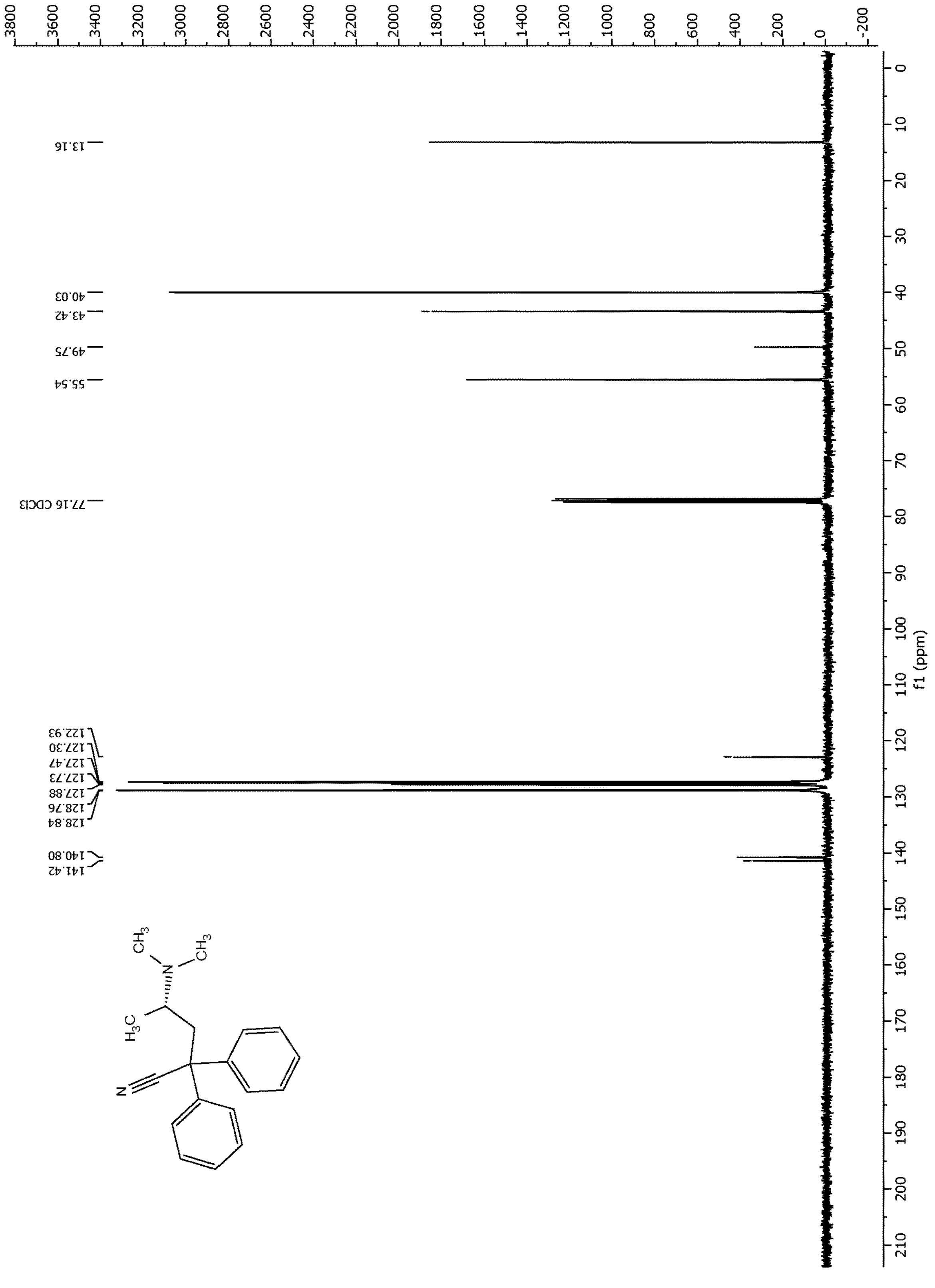
FIG. 21 is a graph showing the $^{13}C$ NMR spectrum of (S)-methadone nitrile.

To a 100 mL Morton Type round bottom flask equipped with a magnetic stir bar was added benzyl (S)-(4-cyano-4,4-diphenylbutan-2-yl)carbamate ((S)-4') (1.00 g, 2.60 mmol, 1 equiv.) and $Pd(OH)_2/C$ 20% on activated charcoal (460 mg, 0.65 mmol, 25 mol %). The vessel was purged with $N_2$ for ~30 min, diluted with EtOH (20 mL, 20 vol.), then to the stirring solution was added aqueous $CH_2O$ 37% w/w (2 mL, 2 vol.). The vessel was equipped with a balloon of $H_2$ and allowed to stir at 25° C. for 24 h. Upon reaction completion, as determined by consumption of ((S)-4') by HPLC, the vessel was purged with $N_2$ for ~30 min. The suspension was filtered through a bed a celite eluting with EtOH (2×5 vol.) and concentrated under reduced pressure to ~2 volumes. To the stirring ethanolic solution was added H2O (14 mL, 14 vol.) over 1 h and the slurry was allowed to stir at 25° C. for 15 h, cooled to −5° C. via an ice-water bath, then stirred for an additional 5 h. The solids were collected via vacuum filtration and washed with $H_2O$ (5 mL, 5 vol.). The collected solids were dried under reduced pressure at 50° C. to provide (S)-4-(dimethylamino)-2,2-diphenylpentanenitrile ((S)-5) as a white solid (630 mg, 87% yield). Chiral HPLC: one single enantiomer (e.e. >99%) as shown in FIG. 19. HRMS (ESI) m/z: $[M+H]^+$ Required $C_{19}H_{22}N_2$ 279.18; Found 279.20. $^1H$ NMR (300 MHz, $CDCl_3$) δ 7.49-7.22 (m, 10H), 2.69 (dd, J=13.7, 6.4 Hz, 1H), 2.54 (h, J=6.4 Hz, 1H), 2.23 (dd, J=13.6, 6.0 Hz, 1H), 2.13 (s, 6H), 0.91 (d, J=6.6 Hz, 3H). ppm, as shown in FIG. 20. $^{13}C$ NMR (101 MHz, $CDCl_3$) δ 141.42, 140.80, 128.84, 128.76, 127.88, 127.73, 127.47, 127.30, 122.93, 55.54, 49.75, 43.42, 40.03, 13.16 ppm, as shown in FIG. 21.

Example 4: (R)-4-(dimethylamino)-2,2-diphenylpentanenitrile ((R)-5)

Figure 22:
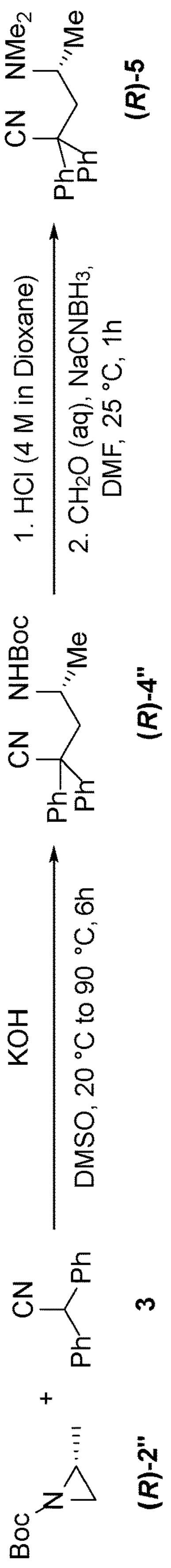
FIG. 22 is a schematic showing the synthesis of (R)-methadone nitrile using Boc-protected (R)-2-methylaziridine starting material.

This Example 4 describes a two-step method that was used to prepare (R)-4-(dimethylamino)-2,2-diphenylpentanenitrile ((R)-5), as shown in FIG. 22.

Step 1: Ring-opening reaction of tert-butyl (R)-2-methylaziridine-1-carboxylate ((R)-2") on the 2,2-diphenylacetonitrile (3) anion to form tert-butyl (R)-(4-cyano-4,4-diphenylbutan-2-yl)carbamate ((R)-4").

Figure 23:
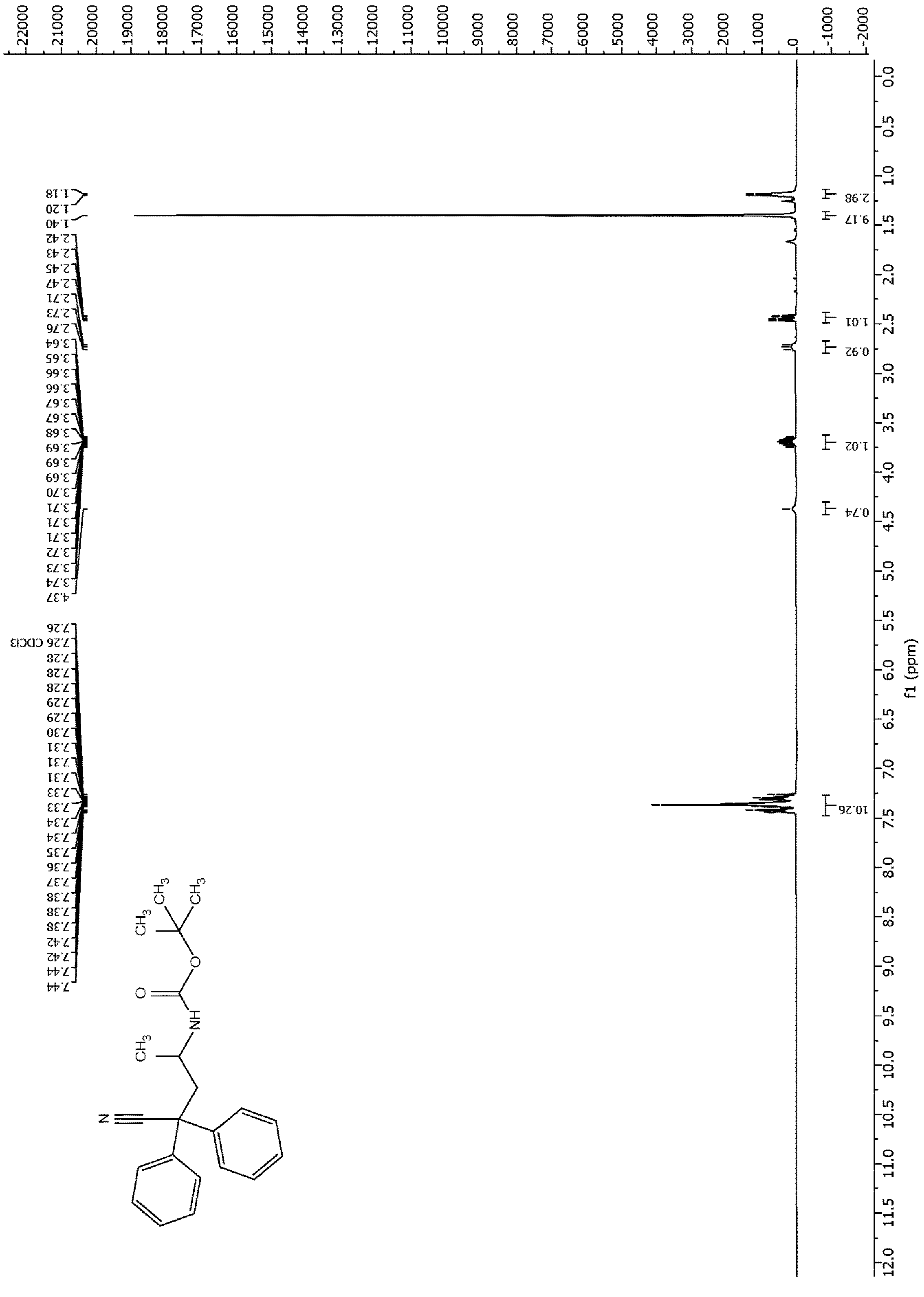
FIG. 23 is a graph showing the $^{1}H$ NMR spectrum of tert-butyl (R)-(4-cyano-4,4-diphenylbutan-2-yl)carbamate.
Figure 24:
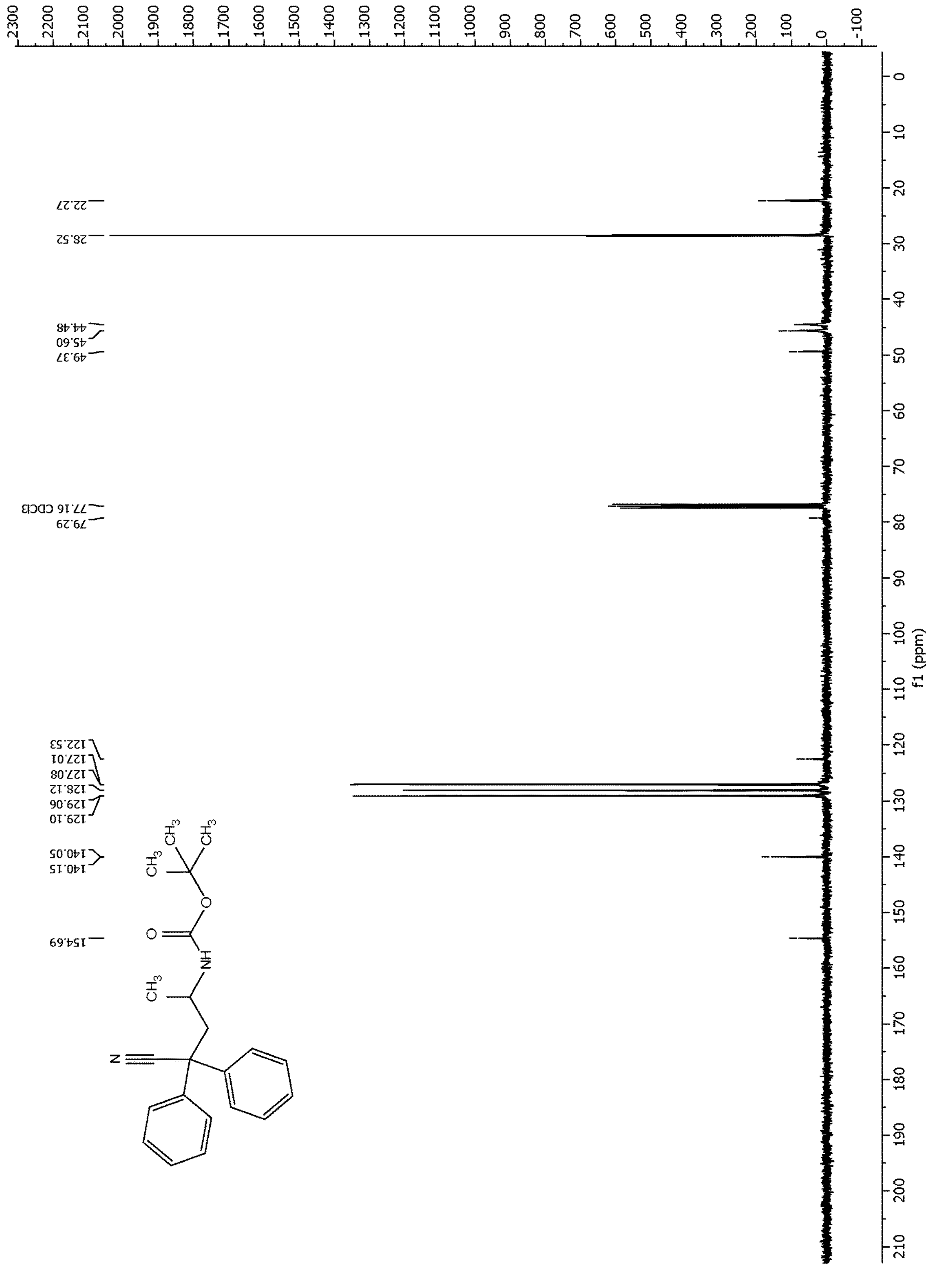
FIG. 24 is a graph showing the $^{13}C$ NMR spectrum of tert-butyl (R)-(4-cyano-4,4-diphenylbutan-2-yl)carbamate.

To a solution of KOH (35 mg) in anhydrous DMSO (1.44 mL) was added diphenylacetonitrile (3) (0.669 g, 3.5 mmol, 1.25 eq.) and a solution of tert-butyl (R)-2-methylaziridine-1-carboxylate ((R)-2") (0.4365 g, 2.8 mmol, 1.0 eq.) in anhydrous DMSO (2.91 mL). The reaction mixture was stirred at 90° C. for 6 h. Upon reaction completion, as determined by consumption of (R)-2" by $^1H$-NMR and TLC (Hex:EtOAc [8:2 ratio] using potassium permanganate stain, Rf=~0.6), stirring was discontinued. The resulting mixture was then poured into 50 mL of water/brine 1:1 and DCM (50 mL) was added. The organic layer was separated and the aqueous phase was further extracted with DCM (20 mL×3). The combined organic layers were evaporated under reduced pressure and the crude was purified by column chromatography using DCM/ethyl acetate 98:2 as eluent to obtain tert-butyl (R)-(4-cyano-4,4-diphenylbutan-2-yl)carbamate ((R)-4") as a pale yellow solid (0.756 g, 78% yield). HRMS (ESI) m/z: $[M+H]^+$ Required $C_{22}H_{26}N_2O_2$ 351.2067; Found: 351.2078. $^1H$ NMR (400 MHz, $CDCl_3$) δ 7.48-7.27 (m, 10H), 4.38 (s, 1H), 3.76-3.63 (m, 1H), 2.80-2.67 (m, 1H), 2.44 (dd, J=14.2, 5.2 Hz, 1H), 1.40 (s, 9H), 1.19 (d, J=6.6 Hz, 3H) ppm, as shown in FIG. 23. $^{13}C$ NMR (101 MHz, $CDCl_3$) δ 154.69, 140.15, 140.05, 129.10, 129.06, 128.12, 127.08, 127.01, 122.53, 79.29, 49.37, 45.60, 44.48, 28.52, 22.27 ppm, as shown in FIG. 24.

Step 2: Two-step/one-pot deprotection/reductive amination of tert-butyl (R)-(4-cyano-4,4-diphenylbutan-2-yl)carbamate ((R)-4") to form (R)-methadone nitrile ((R)-5).

Figure 25A:
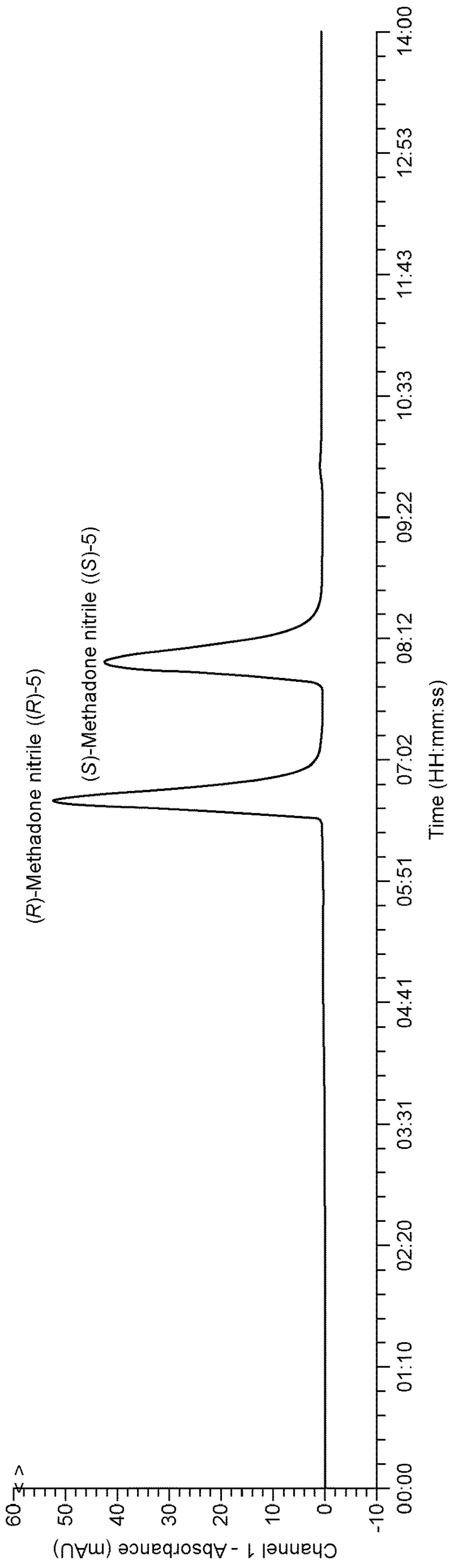
FIG. 25A is a chiral HPLC chromatogram of (R,S)-methadone nitrile.
Figure 25B:
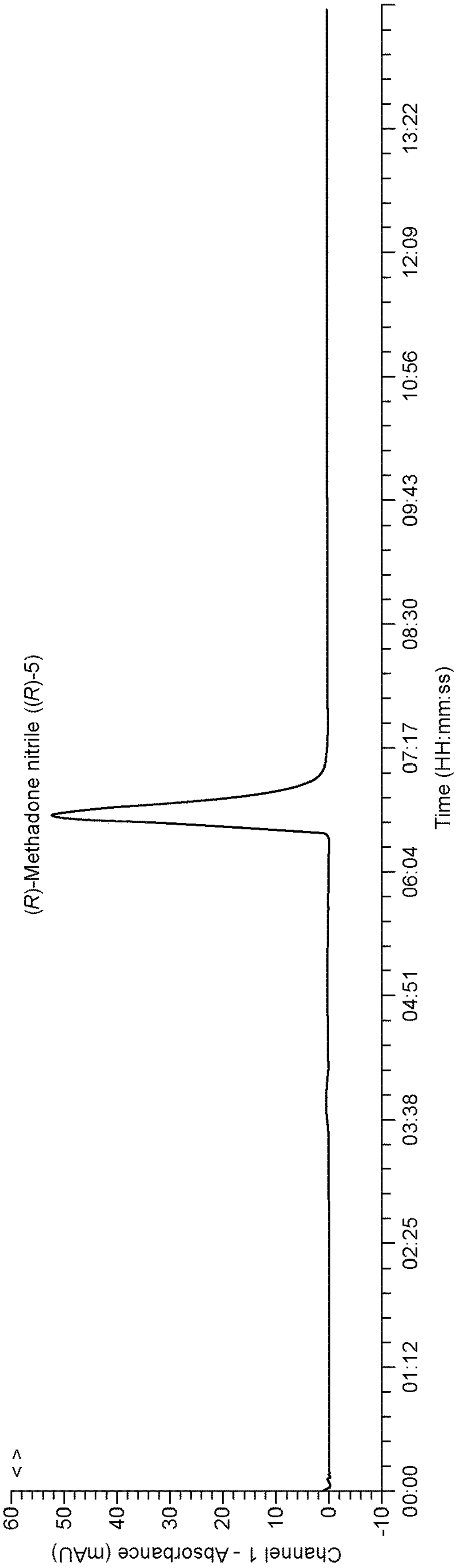
FIG. 25B is a chiral HPLC chromatogram of (R)-methadone nitrile.
Figure 26:
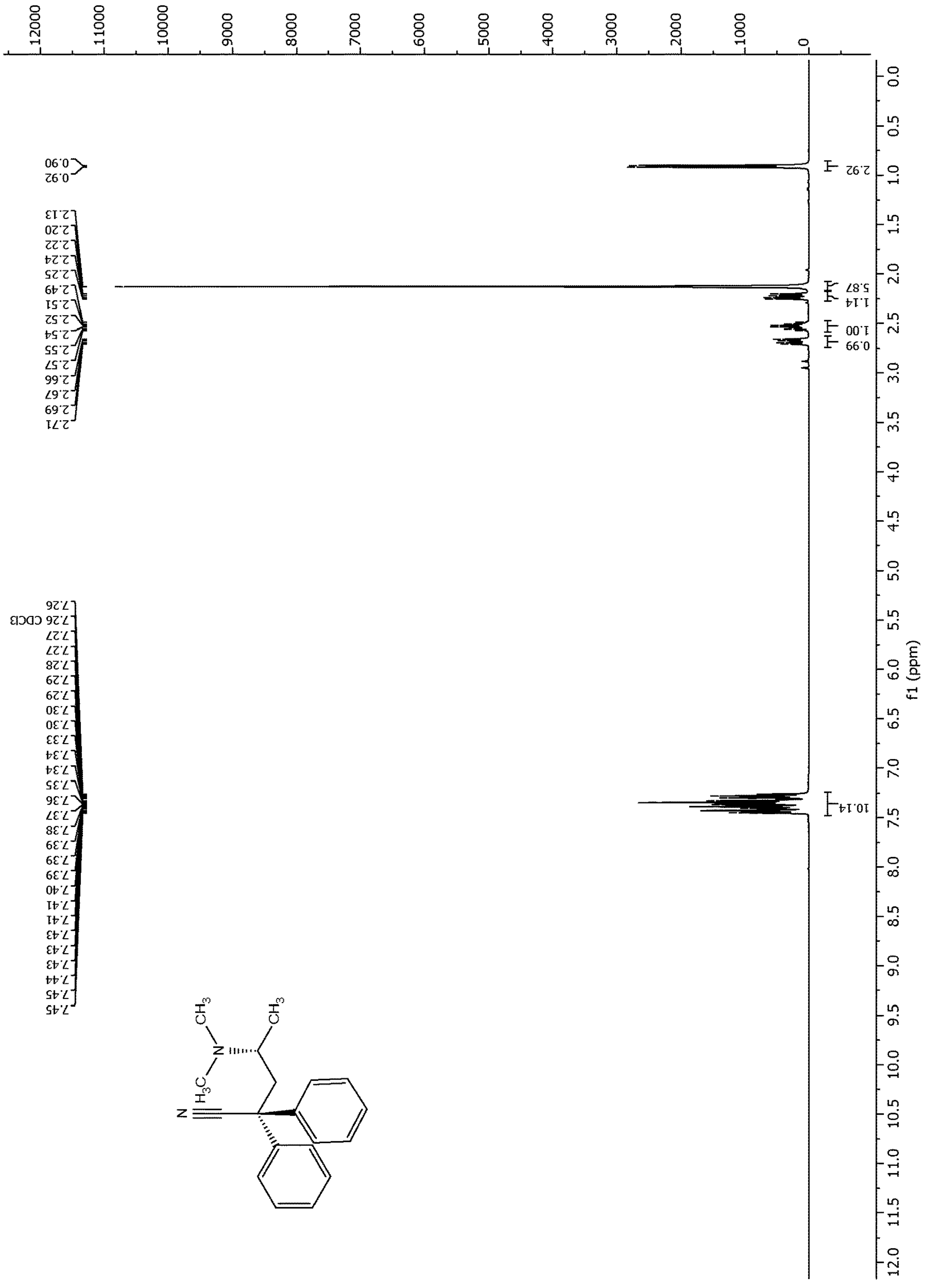
FIG. 26 is a graph showing the $^{1}H$ NMR spectrum of (R)-methadone nitrile.
Figure 27:
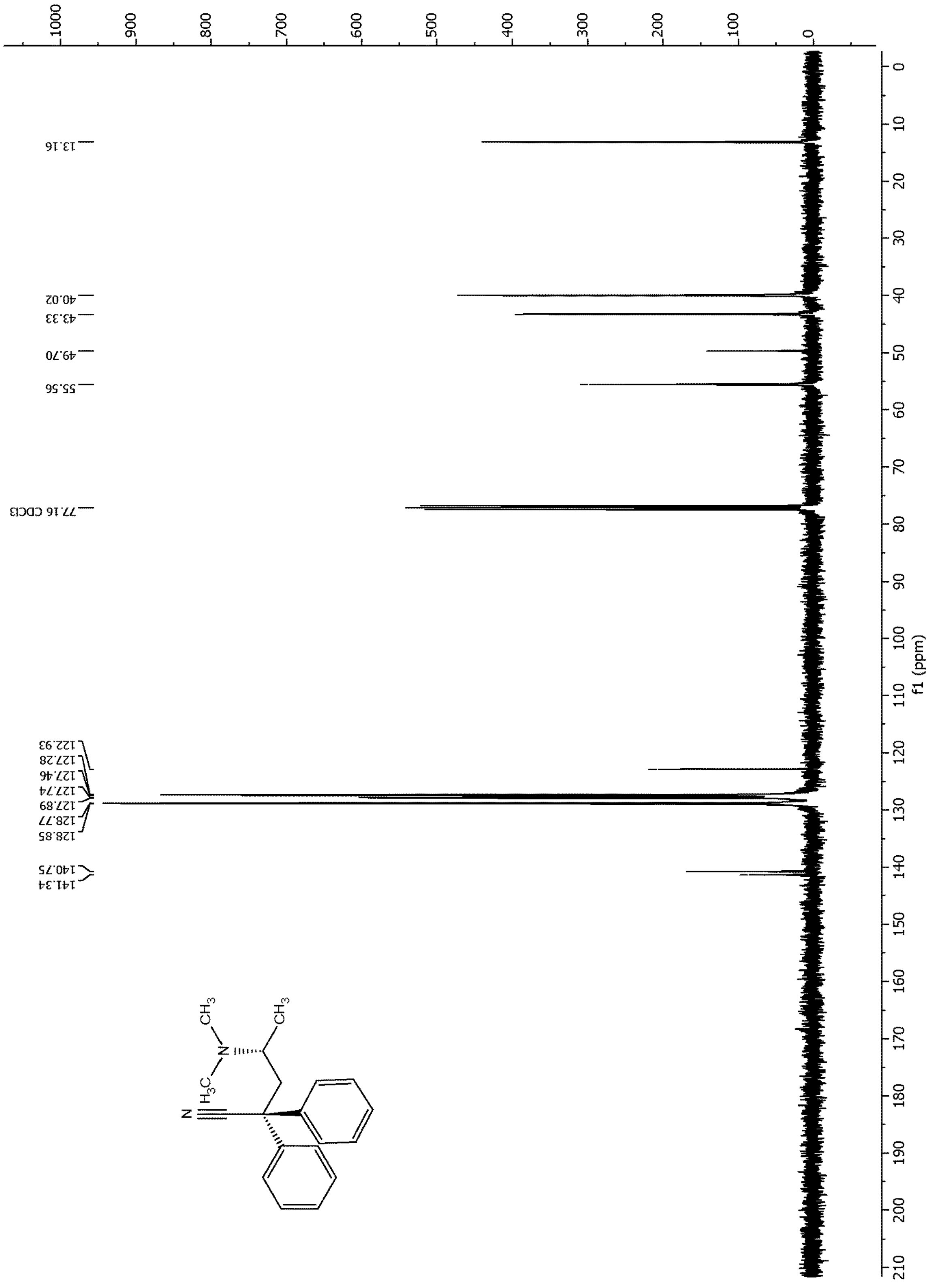
FIG. 27 is a graph showing the $^{13}C$ NMR spectrum of (R)-methadone nitrile.

To an ice-cooled solution of tert-butyl (R)-(4-cyano-4,4-diphenylbutan-2-yl)carbamate ((R)-4") (0.200 g, 0.57 mmol, 1 eq.) in DCM (2 mL) was added HCl (4M in dioxane, 2 mL, 14 mmol, 25 eq.) dropwise under nitrogen atmosphere and the mixture was stirred at 0° C. for 3 h. Then, the solvents and residual HCl were removed under reduced pressure to obtain a slightly yellow oil of Boc-deprotected (R)-4" which was redissolved in DMF (4.3 mL) and cooled in ice-bath. Formaldehyde (37% in water, 1.15 mL, 15 mmol, 25 eq.) and $NaCNBH_3$ (76 mg, 1.22 mmol, 2 eq) were added and the mixture was stirred at rt for 1 h. The solution was then poured into 50 mL of sat. $NaHCO_3$ and extracted with DCM (3×50 mL). The combined organic fractions were evaporated under reduced pressure, and the crude was purified by column chromatography using $CHCl_3$/Methanol 95:5 as eluent to obtain (R)-4-(dimethylamino)-2,2-diphenylpentanenitrile ((R)-5) (138 mg, 87% yield). Chiral HPLC: one single enantiomer (e.e. >99%) as shown in FIG. 25. HRMS (ESI) m/z: $[M+H]^+$ Required $C_{19}H_{22}N_2$ 279.1861; Found 279.1924. $^1H$ NMR (400 MHz, $CDCl_3$) δ 7.48-7.24 (m, 10H), 2.68 (dd, J=13.8, 6.5 Hz, 1H), 2.59-2.47 (m, 1H), 2.23 (dd, J=13.9, 6.0 Hz, 1H), 2.13 (s, 6H), 0.91 (d, J=6.6 Hz, 3H) ppm, as shown in FIG. 26. $^{13}C$ NMR (101 MHz, $CDCl_3$) δ 141.34, 140.75, 128.85, 128.77, 127.89, 127.74, 127.46, 127.28, 122.93, 55.56, 49.70, 43.33, 40.02, 13.16 ppm, as shown in FIG. 27.

Example 5: (S)-6-(Dimethylamino)-4,4-Diphenyl-3-Heptanone Hydrochloride ((S)-Methadone*HCl)

Figure 28:
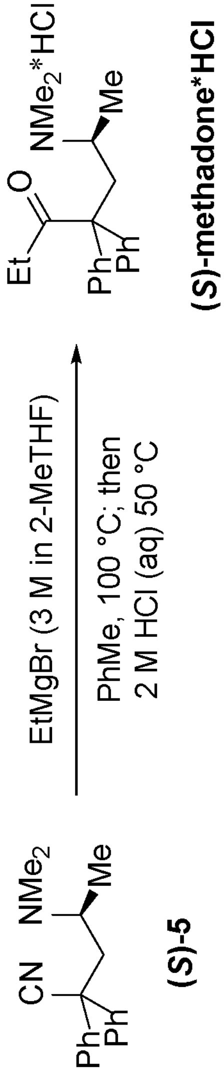
FIG. 28 is a schematic showing the synthesis of (S)-methadone hydrochloride from (S)-4-(dimethylamino)-2,2-diphenylpentanenitrile.

This Example 5 describes a one-step method that was used to prepare (S)-6-(dimethylamino)-4,4-diphenyl-3-heptanone hydrochloride ((S)-methadone*HCl), as shown in FIG. 28. This step was carried out by following literature procedures (see WO 2017/35224 and US2020/277250, incorporated by reference herein in their entireties) with modifications.

Figure 29A:
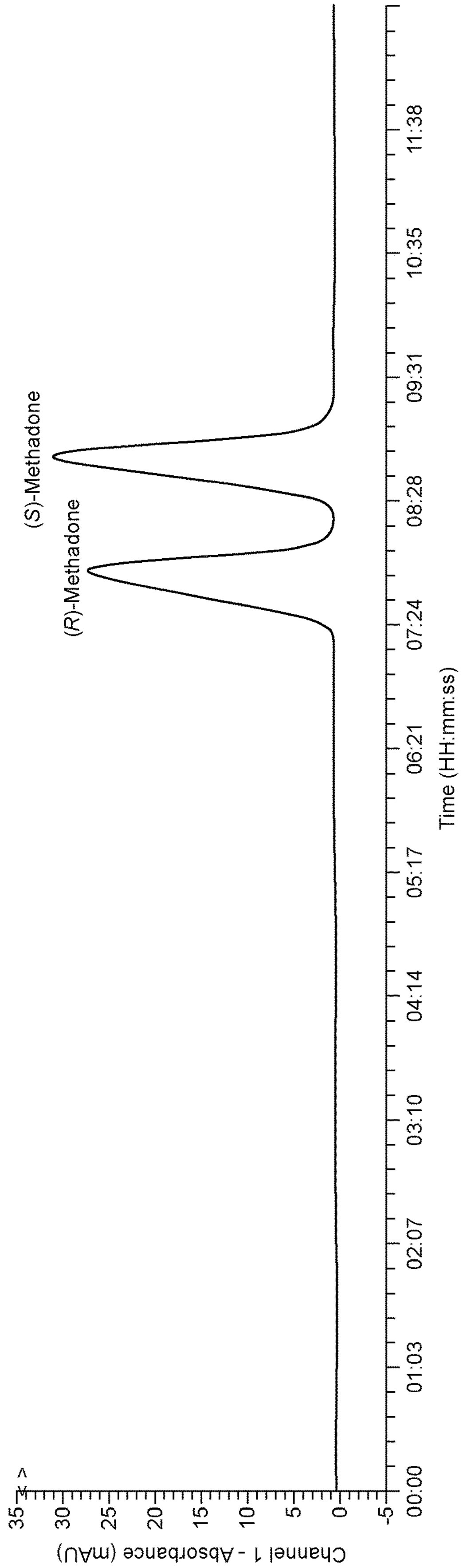
FIG. 29A is a chiral HPLC chromatogram of (R,S)-methadone.
Figure 29B:
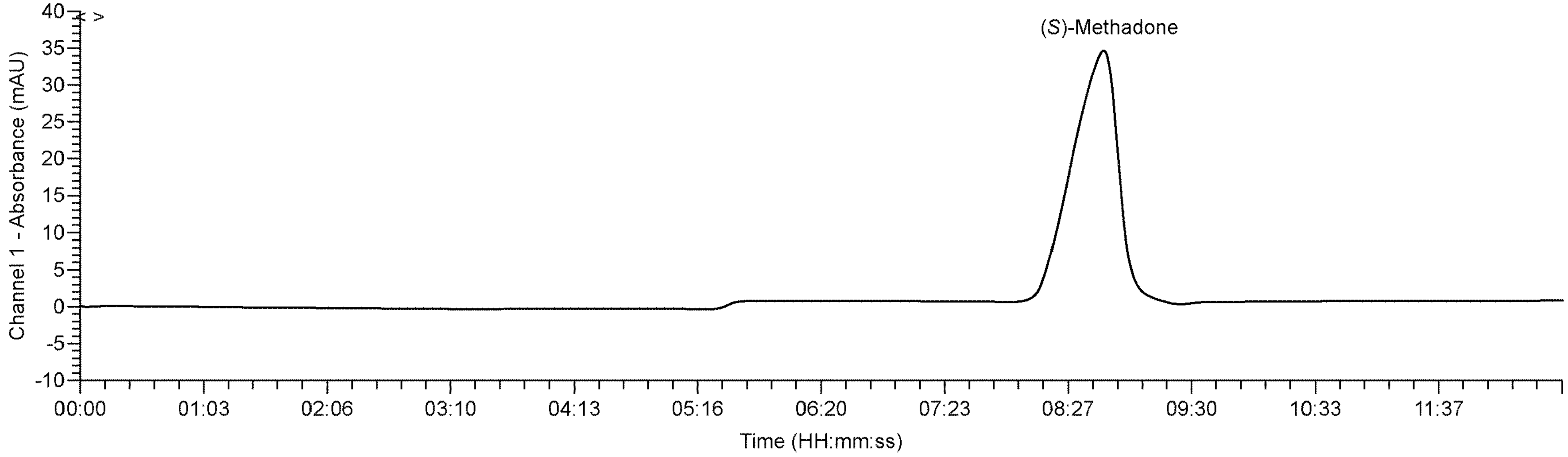
FIG. 29B is a chiral HPLC chromatogram of (S)-methadone.
Figure 30:
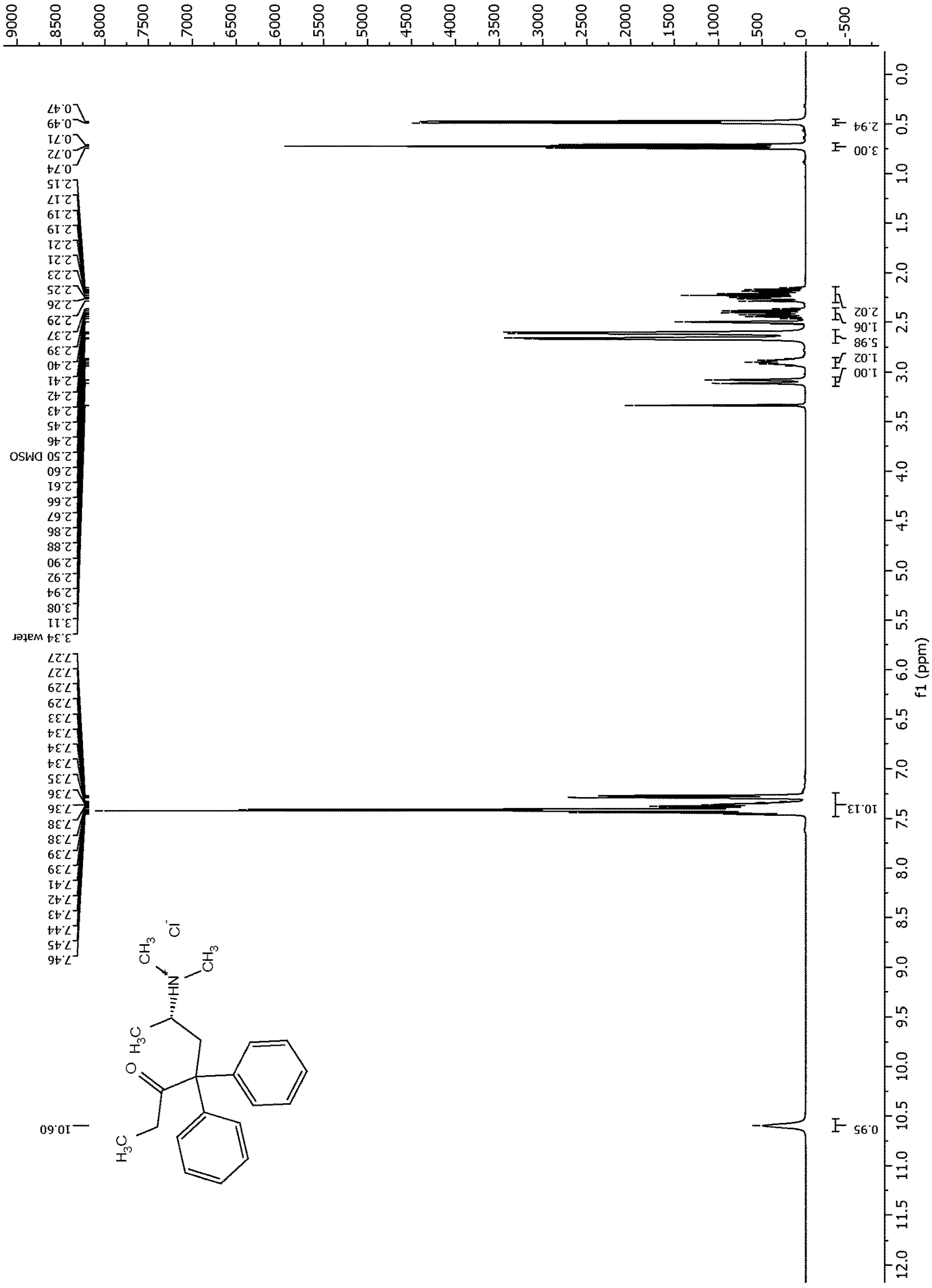
FIG. 30 is a graph showing the $^{1}H$ NMR spectrum of (S)-methadone*HCl.
Figure 31:
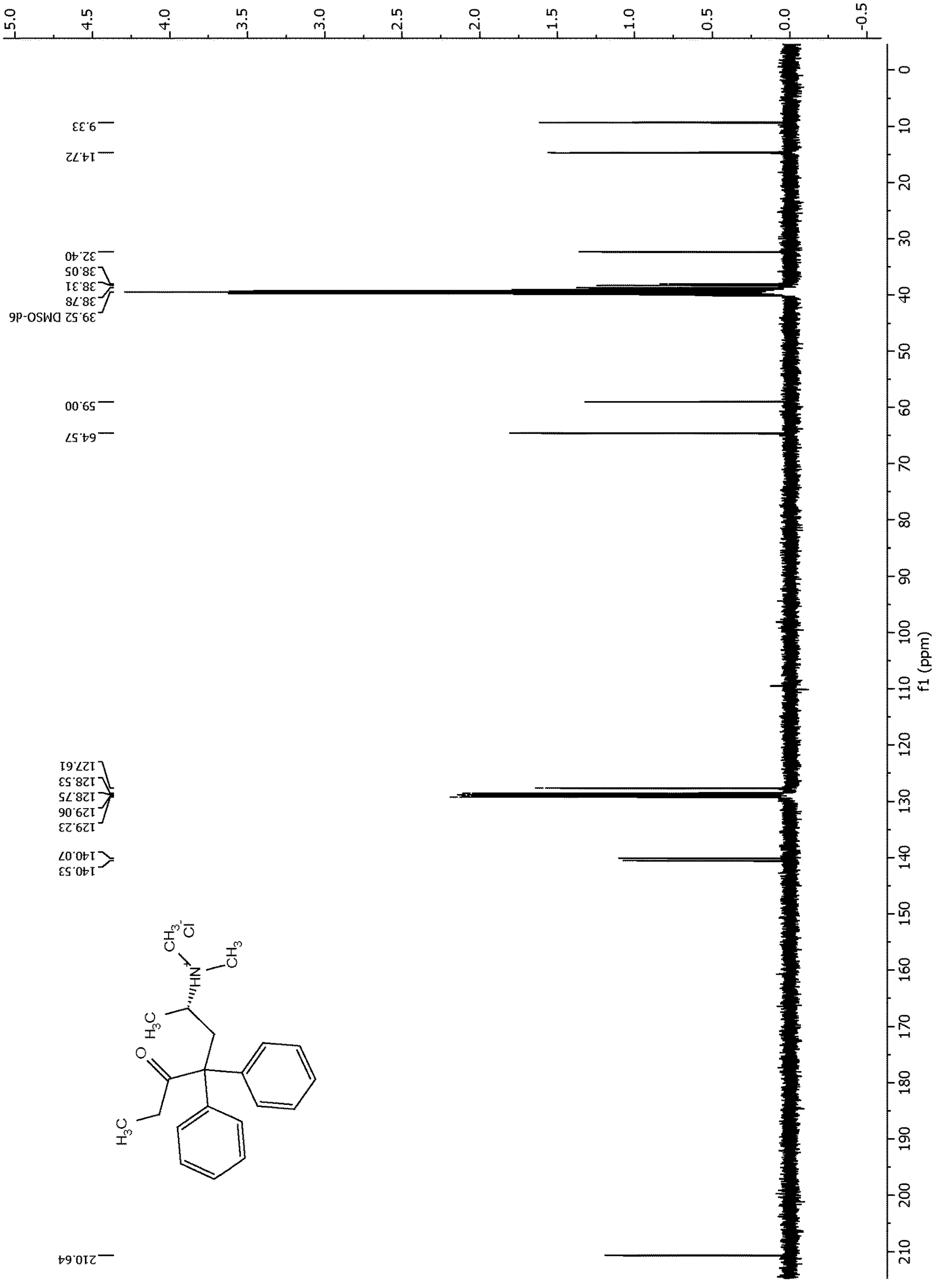
FIG. 31 is a graph showing the $^{13}C$ NMR spectrum of (S)-methadone*HCl.

To a 200 mL two-neck round bottom flask equipped with a thermocouple, magnetic stir bar, and $N_2$ inlet was added (S)-4-(dimethylamino)-2,2-diphenylpentanenitrile ((S)-5) (6.62 g, 23.78 mmol, 1 equiv.). The vessel was purged with $N_2$ for 30 min, diluted with PhMe (66 mL, 10 vol.), and to the resultant solution was added 3 M EtMgBr in 2-MeTHF (12 mL, 35.68 mmol, 1.5 equiv.) dropwise over 30 min. The reaction mixture was then warmed to 100° C. via a heating mantle and allowed to stir for 24 h. Upon consumption of (S)-5 as determined by the HPLC, the solution was cooled to 0° C., and charged with 2 M aqueous HCl (13 mL, 2 vol.). The biphasic mixture was then warmed to 50° C. and allowed to stir vigorously for 24 h. The organic and aqueous fractions were separated, and the aqueous layer was cooled to 0° C. via an ice-water bath. To the viscous solution was added a seed crystal of (S)-methadone hydrochloride to provide a free-flowing slurry. The slurry was allowed to age for 24 h, cooled to 0° C., and the solids were collected via vacuum filtration and dried under reduced pressure at 50° C. for 24 h to provide (S)-6-(dimethylamino)-4,4-diphenyl-3-heptanone hydrochloride ((S)-methadone*HCl) as a white solid (5.20 g, 66% yield). Purity HPLC: 99.6%. Chiral HPLC: one single enantiomer (e.e. >99%) as shown in FIG. 29. HRMS (ESI) m/z: $[M+H]^+$ Required $C_{21}H_{27}NO$ 310.2165; Found: 310.2193. $^1H$ NMR (400 MHz, $DMSO_{d6}$) δ 10.60 (s, 1H), 7.48-7.24 (m, 10H), 3.10 (d, J=13.9 Hz, 1H), 2.90 (p, J=6.9 Hz, 1H), 2.63 (dd, J=22.7, 4.7 Hz, 6H), 2.47-2.35 (m, 1H), 2.31-2.14 (m, 2H), 0.72 (t, J=7.2 Hz, 3H), 0.48 (d, J=6.5 Hz, 3H) ppm, as shown in FIG. 30. $^{13}C$ NMR (400 MHz, $DMSO_{d6}$) δ 210.64, 140.53, 140.07, 129.23, 129.06, 128.75, 128.53, 127.61, 64.57, 59.00, 38.78, 38.31, 38.05, 32.40, 14.72, 9.33 ppm, as shown in FIG. 31.

Example 6: (R)-6-(Dimethylamino)-4,4-Diphenyl-3-Heptanone Hydrochloride ((R)-Methadone*HCl)

Figure 32:
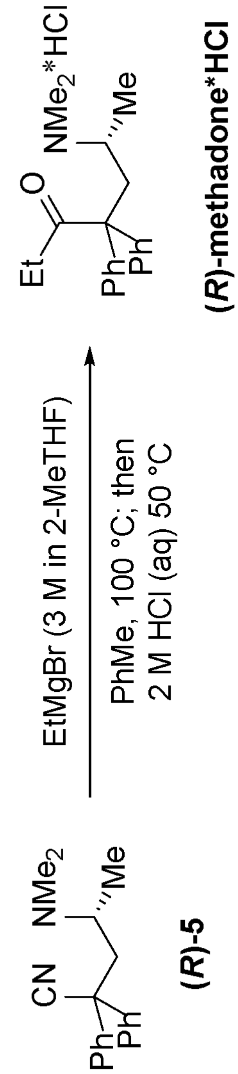
FIG. 32 is a schematic showing the synthesis of (R)-methadone hydrochloride from (R)-4-(dimethylamino)-2,2-diphenylpentanenitrile.

This Example 6 describes a one-step method that was used to prepare (R)-6-(dimethylamino)-4,4-diphenyl-3-heptanone hydrochloride ((R)-methadone*HCl), as shown in FIG. 32. This step was carried out by following literature procedures (see WO 2017/35224 and US2020/277250, incorporated by reference herein in their entireties) with modifications.

Figure 33A:
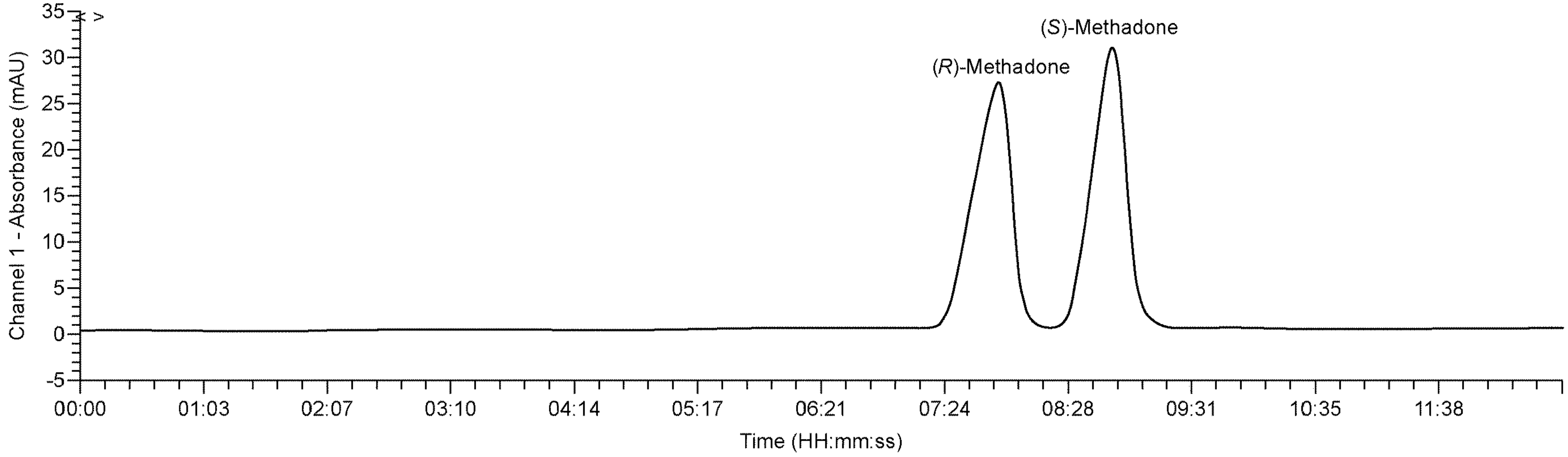
FIG. 33A is a chiral HPLC chromatogram of (R,S)-methadone.
Figure 33B:
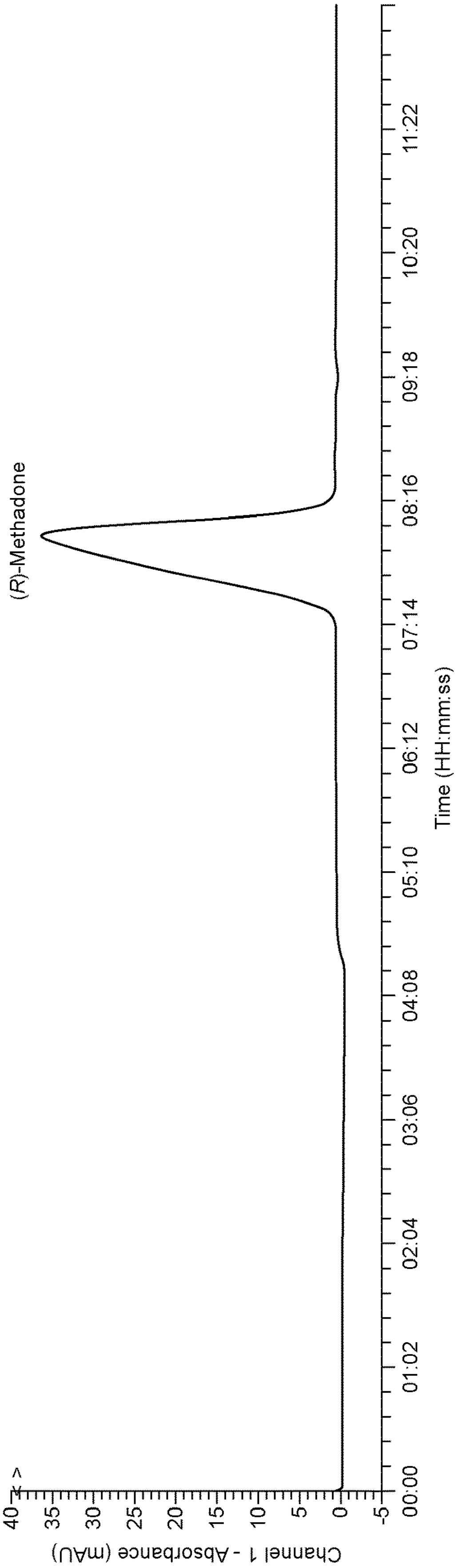
FIG. 33B is a chiral HPLC chromatograms of (R)-methadone.
Figure 34:
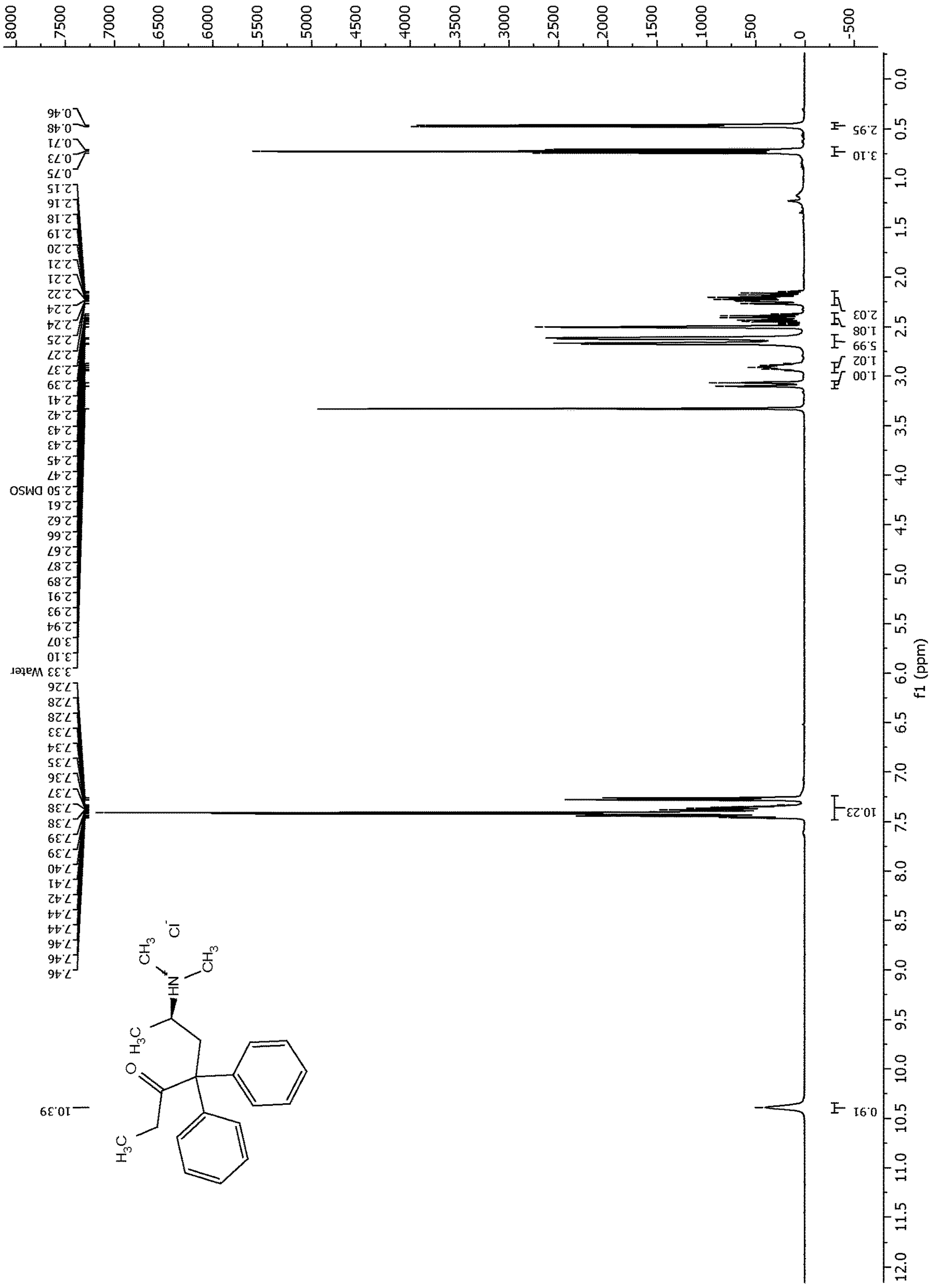
FIG. 34 is a graph showing the $^{1}H$ NMR spectrum of (R)-methadone*HCl.
Figure 35:
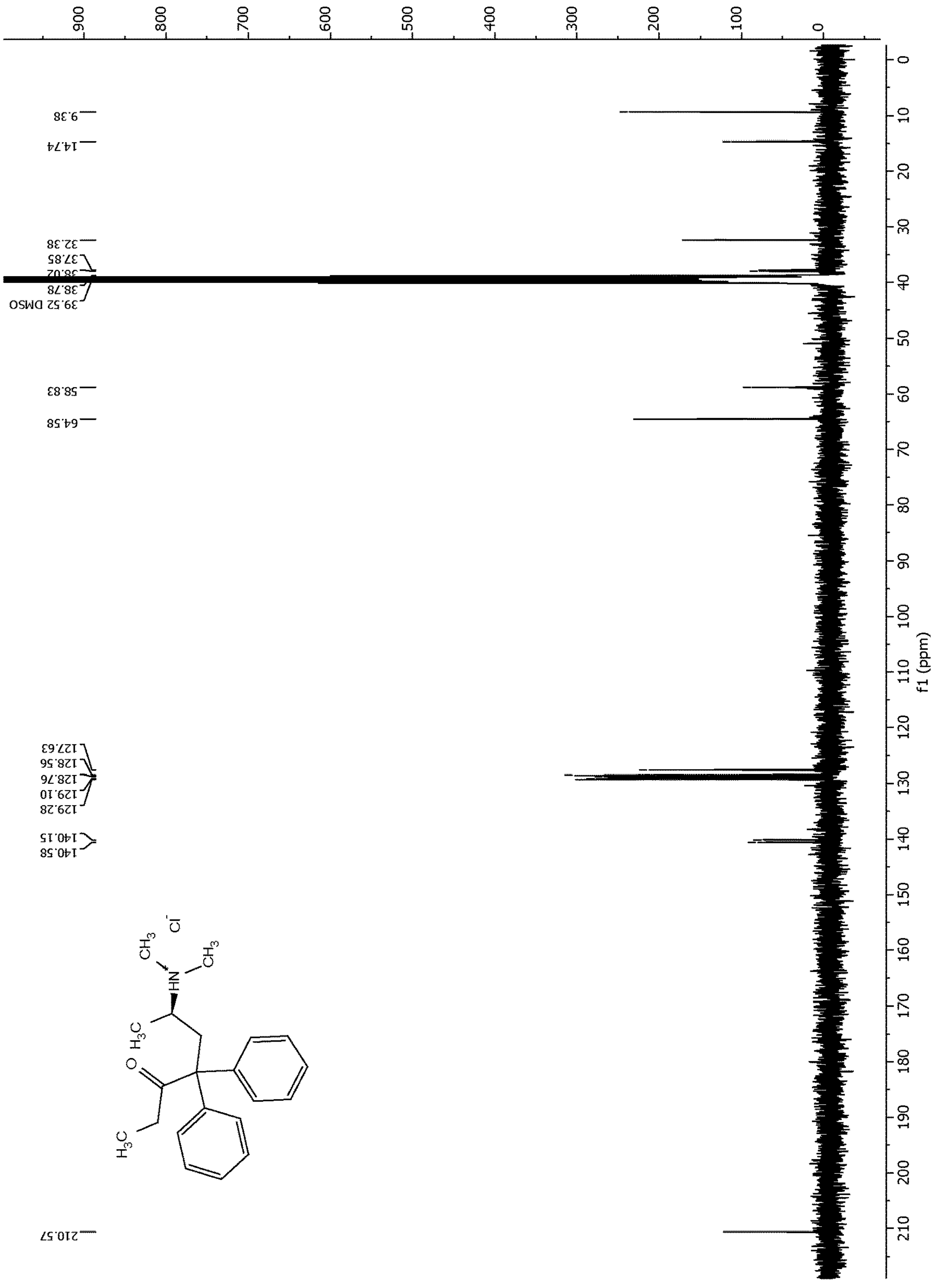
FIG. 35 is a graph showing the $^{13}C$ NMR spectrum of (R)-methadone*HCl.

To a 100 mL two-neck round bottom flask equipped with a thermocouple, magnetic stir bar, and $N_2$ inlet was added (R)-4-(dimethylamino)-2,2-diphenylpentanenitrile ((R)-5) (2.80 g, 10.06 mmol, 1 equiv.). The vessel was purged with $N_2$ for 30 min, diluted with PhMe (28 mL, 10 vol.), and to the resultant solution was added 3 M EtMgBr in 2-MeTHF (5 mL, 15.09 mmol, 1.5 equiv.) dropwise over 30 min. The reaction mixture was then warmed to 100° C. via a heating mantle and allowed to stir for 24 h. Upon consumption of (R)-5 as determined by the HPLC, the solution was cooled to 0° C., and charged with 2 M aqueous HCl (6 mL, 2 vol.). The biphasic mixture was then warmed to 50° C. and allowed to stir vigorously for 24 h. The organic and aqueous fractions were separated, and the aqueous layer was cooled to 0° C. via an ice-water bath. To the viscous solution was added a seed crystal of (R)-methadone hydrochloride to provide a free-flowing slurry. The slurry was allowed to age for 24 h, cooled to 0° C., and the solids were collected via vacuum filtration and dried under reduced pressure at 50° C. for 24 h to provide (R)-6-(dimethylamino)-4,4-diphenyl-3-heptanone hydrochloride ((R)-methadone*HCl) as a white solid (2.44 g, 70% yield). Purity HPLC: 99.5%. Chiral HPLC: one single enantiomer (e.e. >99%) as shown in FIG. 33. HRMS (ESI) m/z: $[M+H]^+$ Required $C_{21}H_{27}NO$ 310.2165; Found: 310.2234. $^1H$ NMR (400 MHz, $DMSO_{d6}$) δ 10.39 (s, 1H), 7.48-7.24 (m, 10H), 3.08 (d, J=13.9 Hz, 1H), 2.91 (p, J=7.0 Hz, 1H), 2.64 (dd, J=21.5, 4.5 Hz, 6H), 2.48-2.36 (m, 1H), 2.29-2.13 (m, 2H), 0.73 (t, J=7.2 Hz, 3H), 0.47 (d, J=6.6 Hz, 3H) ppm, as shown in FIG. 34. $^{13}C$ NMR (400 MHz, $DMSO_{d6}$) δ 210.57, 140.58, 140.15, 129.28, 129.10, 128.76, 128.56, 127.63, 64.58, 58.83, 38.78, 38.02, 37.85, 32.38, 14.74, 9.38 ppm, as shown in FIG. 35.

While the present invention has been disclosed by reference to the details of preferred embodiments of the invention, it is to be understood that the disclosure is intended as an illustrative rather than in a limiting sense, as it is contemplated that modifications will readily occur to those skilled in the art, within the spirit of the invention and the scope of the amended claims.

What is claimed is:

1. A method for preparing(S)-methadone, (R)-methadone or (R,S)-methadone from optically pure ((S)- or (R)-) or racemic N-protected 4-methyl-cyclic sulfamidate or N-protected 2-methylaziridine, the method comprising:

a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration;

a two-step/one-pot deprotection/reductive amination of the N-protected-dinormethadone nitrile to provide (R)-, (S)-, or (R,S)-methadone nitrile; and a reaction of the (R)-, (S)-, or (R,S)-methadone nitrile with an organomagnesium halide reagent to form an ethyl-imine intermediate, followed by imine hydrolysis to provide (R)-, (S)-, or (R,S)-methadone.

2. The method of claim 1, wherein the organomagnesium halide reagent is EtMgX, wherein X is selected from CI, Br, and I.

3. The method of claim 1, wherein the N-protecting group of N-protected 4-methyl-cyclic sulfamidate or N-protected 2-methyl azi ri dine is selected from fluorenylmethyloxycarbonyl (Fmoc), tert-butyloxycarbonyl (Boc), carboxybenzyl (Cbz), acetyl (C(0)CH3), trifluoroacetyl (C(0)CF3), benzyl (Bn), triphenylmethyl (CPh3), and p-toluenesulfonyl (Ts).

4. The method of claim 1, wherein enantiomeric excess (e.e.) is greater than a percentage selected from 90%, 95%, 97%, 99%, 99.5%, and 99.9%.

5. A method for preparing(S)-methadone hydrochloride, (R)-methadone hydrochloride or (R,S)-methadone hydrochloride, the method comprising:

a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration;

a two-step/one-pot deprotection/reductive amination of the N-protected-dinormethadone nitrile to provide (R)-, (S)-, or (R,S)-methadone nitrile; and a reaction of the (R)-, (S)-, or (R,S)-methadone nitrile with an organomagnesium halide reagent to form an ethyl-imine intermediate, followed by hydrochloric acid-mediated imine hydrolysis to provide (R)-, (S)-, or (R,S)-methadone hydrochloride.

6. The method of claim 5, wherein the organomagnesium halide reagent is EtMgX, wherein X is selected from CI, Br, and I.

7. The method of claim 5, wherein the N-protecting group of N-protected 4-methyl-cyclic sulfamidate or N-protected 2-methylaziridine is selected from fluorenylmethyloxycarbonyl (Fmoc), tert-butyloxycarbonyl (Boc), carboxybenzyl (Cbz), acetyl (C(0)CH3), trifluoroacetyl (C(0)CF3), benzyl (Bn), triphenylmethyl (CPh3), and p-toluenesulfonyl (Ts).

8. The method of claim 5, wherein enantiomeric excess (e.e.) is greater than a percentage selected from 90%, 95%, 97%, 99%, 99.5%, and 99.9%.

9. A method for preparing (R)-, (S)-, or (R,S)-methadone nitrile, the method comprising:

a ring opening reaction of optically pure ((S)- or (R)-) or racemic N-protected 4-methyl-cyclic sulfamidate or N-protected 2-methylaziridine with diphenylacetonitrile in the presence of a base to provide ((S)- or (R)-) or racemic N-protected-dinormethadone nitrile with retention of configuration;

a two-step/one-pot deprotection/reductive amination of the N-protected-dinormethadone nitrile to provide (R)-, (S)-, or (R,S)-methadone nitrile.

* * * * *